US009850466B2

(12) United States Patent
Tlsty

(10) Patent No.: US 9,850,466 B2
(45) Date of Patent: Dec. 26, 2017

(54) SOMATIC CELLS WITH INNATE POTENTIAL FOR PLURIPOTENCY

(75) Inventor: Thea D. Tlsty, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 499 days.

(21) Appl. No.: 13/978,947

(22) PCT Filed: Jan. 19, 2012

(86) PCT No.: PCT/US2012/021911
§ 371 (c)(1),
(2), (4) Date: Jan. 7, 2014

(87) PCT Pub. No.: WO2012/100084
PCT Pub. Date: Jul. 26, 2012

(65) Prior Publication Data
US 2014/0120542 A1 May 1, 2014

Related U.S. Application Data

(60) Provisional application No. 61/434,264, filed on Jan. 19, 2011.

(51) Int. Cl.
| | |
|---|---|
| *C12N 5/00* | (2006.01) |
| *C12N 5/10* | (2006.01) |
| *C12N 5/071* | (2010.01) |
| *C12N 5/074* | (2010.01) |
| *C12N 5/0735* | (2010.01) |
| *C12N 5/0775* | (2010.01) |

(52) U.S. Cl.
CPC ......... *C12N 5/0678* (2013.01); *C12N 5/0606* (2013.01); *C12N 5/0607* (2013.01); *C12N 5/0662* (2013.01); *C12N 2506/095* (2013.01)

(58) Field of Classification Search
None
See application file for complete search history.

(56) References Cited

U.S. PATENT DOCUMENTS

| | | | |
|---|---|---|---|
| 2005/0008624 A1* | 1/2005 | Peled | C12N 5/0647 424/93.21 |
| 2007/0148766 A1 | 6/2007 | Yoshimura et al. | |
| 2008/0233610 A1 | 9/2008 | Thomson et al. | |
| 2008/0280362 A1 | 11/2008 | Jaenisch et al. | |
| 2009/0068742 A1 | 3/2009 | Yamanaka | |
| 2009/0180997 A1 | 7/2009 | Pittenger et al. | |
| 2009/0191159 A1 | 7/2009 | Sakurada et al. | |
| 2009/0305413 A1 | 12/2009 | Kang | |

FOREIGN PATENT DOCUMENTS

WO 20070044314 4/2007

OTHER PUBLICATIONS

Barry et al, The SH-3 and SH-4 Antibodies Recognize Distinct Epitopes on CD73 from human Mesenchymal Stem Cells. Biochemical and Biophysical Research Communications. 2001. 289:519-524.*
Pittenger et al., 1999, Science 243: 143-137.*
Delorme et al., 2008, Blood 111: 2631-2635.*
BD Biosciences, available online at https://www.bdbiosciences.com/documents/cd_marker_handbook.pdf, 2010. 47 pages.*
Phelan, Mary C. Techniques for Mammalian Cell Tissue Culture, Current Protocols in Human Genetics, 2006. A.3G.1-A.3G.18.*
Beltrami, et al. "Pluripotency rush! Molecular cues for pluripotency, genetic reprogramming of adult stem cells, and widely multipotent adult cells", Pharmacology & Therapeutics 124 (2009) 23-30.
Brignier, et al. "Embryonic and adult stem cell therapy", J Allergy Clin Immunol, vol. 125, No. 2, S336-S344, 2010.
Leeb, et al. "Promising New Sources for Pluripotent Stem Cells", Stem Cell Rev and Rep, (2010) 6:15-26.
Mosna, et al "Human Bone-Marrow and Adipose Tissue Mesenchymal Stem Cells: A User's Guide", A practical reference for human Bone Marrow and Adipose Tissue Mesenchymal Stem Cells, Stem Cells and Development, Human Bone-Marrow and Adipose Tissue Mesenchymal Stem Cells: A User's Guide, 2010, pp. 1-53.
Jones et al. (2006) "Optimization of a Flow Cytometry-Based Protocol for Detection and Phenotypic Characterization of Multipotent Mesenchymal Stromal Stem Cells from Human Bone Marrow" Cytometry B Clin Cytom 70(6):391-399.
Lee et al. (2004) "Isolation of Multipotent Mesenchymal Stem Cells from Umbilical Cord Blood" Blood 103(5):1669-1675.
Pacini et al. (2010) "Constitutive Expression of Pluripotency-Associated Genes in Mesodermal Progenitor Cells (MPCs)" PlosOne 5(3):1-7.
Roederer et al. (1995) "CD8 Naive T Cell Counts Decrease Progressively in HIV-Infected Adults" J Clin Invest 95:2061-2066.
Bartunek et al. (2007) "Pretreatment of Adult Bone Marrow Mesenchymal Stem Cells with Cardiomyogenic Growth Factors and Repair of the Chronically Infarcted Myocardium" Am J Physiol Heart Circ Physiol 292(2):H1095-H1104.
Debnath et al. (2003) "Morphogenesis and Oncogenesis of MCF-10A Mammary Epithelial Acini Grown in Three-Dimensional Basement Membrane Cultures" Methods 30:256-268.
Dontu et al. (2003) "In Vitro Propagation and Transcriptional Profiling of Human Mammary Stem/Progenitor Cells" Genes Dev 17(10):1253-1270.
GenBank Accession No. AAG13904 "Thy-1 glycoprotein [*Homo sapiens*]" dated Mar. 5, 2001.

(Continued)

*Primary Examiner* — Christopher M Babic
*Assistant Examiner* — Kimberly A Aron
(74) *Attorney, Agent, or Firm* — Shweta Chandra; Carol L. Francis; Bozicevic, Field & Francis LLP

(57) ABSTRACT

Aspects of the present invention are drawn to compositions of somatic cells with innate potential for pluripotency (SCIPP). SCIPP have the capacity to differentiate into functional derivatives of each of the major germ layers (i.e., ectodermal, endodermal and mesodermal). Also provided are methods and kits for identifying and isolating the somatic cells from a subject as well as for employing SCIPP for research or therapeutic purposes.

14 Claims, 35 Drawing Sheets

(56) References Cited

OTHER PUBLICATIONS

GenBank Accession No. AAH65559 "Thy-1 cell surface antigen [*Homo sapiens*]" dated Jul. 15, 2006.
GenBank Accession No. AAH65937 "5'-nucleotidase, ecto (CD73) [*Homo sapiens*]" dated Jul. 15, 2006.
GenBank Accession No. "AI040168 ox42c08.s1 Soares_total_fetus_Nb2HF8_9w *Homo sapiens* cDNA clone IMAGE:1658990 3-, mRNA sequence" dated Jan. 5, 2011.
GenBank Accession No. NP_002517 "5'-nucleotidase precursor [*Homo sapiens*]" dated Jan. 2, 2011.
GenBank Accession No. NP_006279 "thy-1 membrane glycoprotein preproprotein [*Homo sapiens*]" dated Dec. 26, 2010.
GenBank Accession No. P04216, UniProt "RecName: Full=Thy-1 membrane glycoprotein; AltName: Full=CDw90; AltName: Full=Thy-1 antigen; AltName: CD_antigen=CD90; Flags: Precursor" dated Jan. 11, 2011.
Kroon et al. (2008) "Pancreatic Endoderm Derived from Human Embryonic Stem Cells Generates Glucose-Responsive Insulin-Secreting Cells In Vivo" Nat Biotechnol 26(4):443-452.
Levenberg et al. (2002) "Endothelial Cells Derived From Human Embryonic Stem Cells" Proc Natl Acad Sci USA 99(7):4391-4396.
Romanov et al. (2001) "Normal Human Mammary Epithelial Cells Spontaneously Escape Senescence and Acquire Genomic Changes" Nature 409(6820):633-637.
Seki et al. (1985) "The human Thy-1 gene: structure and chromosomal location" Proc Natl Acad Sci USA 82(19):6657-6661.
Bushway, Paul J. et al. (2006) "High-throughput screening for modulators of stem cell differentiation", Elsevier, Acad. Press, 300-316.
Delo, Dawn, et al. (2006): "Amniotic fluid and placental stem cells", Methods in Enzymology, Academic Press, 419:426-438.
Genbacev, et al. (2005) "Serum-free derivation of human embronic stem cell lines on human placental fiboblast feeders", Elsevier Science Inc, 83(5):117-1529.
Mani, Sendurai A. et al. (2008) "The epithelial-msenhymal transition generates cells with properties of sem cells", Cell, Cell Press, 133(4):704-715.
Liao, M.J. et al. (2007) "Enrichment of a Population of Mammary Gland Cells that Form Mammospheres and Have In Vivo Repopulating Activity", Cancer Research, 67(17):8131-8138.
Roy, S. et al. (2013) "Rare somatic cells from human breast tissue exhibit extensive lineage plasticity", Proceedings of the National Academy of Sciences, 110(112):4598-4603.

\* cited by examiner

|  | R1 | R2 | R3 | R4 |
|---|---|---|---|---|
| Avg fraction of total population (n=10) | 5.26 ± 0.54 | 1.88 ± 0.40 | 84.56 ± 1.34 | 8.24 ± 1.33 |
| Avg fraction of total (4%) ALD+ population (n=10) | 40.09 ± 4.43 | 7.96 ± 1.97 | 51.67 ± 4.45 | 0.00 |
| Avg fraction of R population which is ALD+ (n=10) | 30.74 ± 3.92 | 15.75 ± 2.55 | 2.43 ± 0.31 | 0.00 |

Fig.13

| | Parent Mammary Sample 1 | Differentiated Mesoderm (cardiomyogenic) Sample 1 | Parent Mammary Sample 2 | Differentiated Mesoderm (cardiomyogenic) Sample 2 | H7, hESC | K562 (control DNA) |
|---|---|---|---|---|---|---|
| D5S818 | 10,11 | 10,11 | 12 | 12 | 11,13 | 11,12 |
| D13S317 | 10,12 | 10,12 | 8,10 | 8,10 | 11,12,(10)* | 8 |
| D7S820 | 9,12 | 9,12 | 10,11 | 10,11 | 10,11 | 9,11 |
| D16S539 | 11 | 11 | 9 | 9 | 12,13 | 11,12 |
| vWA | 14,18 | 14,18 | 17,20 | 17,20 | 14,15 | 16 |
| TH01 | 6 | 6 | 9,9.3 | 9,9.3 | 6 | 9,3 |
| Amelogenin | X,X | X,X | X,X | X,X | X,X | X,X |
| TPOX | 8 | 8 | 8,9 | 8,9 | 8,11 | 8,9 |
| CSF1PO | 11,12 | 11,12 | 10,12 | 10,12 | 12 | 9,10 |

Fig. 14

Up-Down Regulation (comparing to control group): control group is H9, human ESC

| Symbol | R1-ALD+ | R3-ALD+ | Human MSC | H7, human ESC | R1-ALD- | R3-ALD- |
|---|---|---|---|---|---|---|
| POU5F1/Oct3/4 | -10.4027 | -83.5979 | -189.8771 | 1.5577 | -17.0496 | -77.6867 |
| NANOG | -1.8667 | -53.1278 | -7.8984 | 1.8903 | -6.9145 | -21.2648 |
| SOX2 | -2002.1847 | -59738.2612 | -220559.6336 | -1.1139 | -1619.257 | -120467.0545 |
| KLF4 | 223.0168 | 28.7073 | 6.5708 | 1.0151 | 145.7357 | 16.9763 |
| LIN28 | -475.3196 | -16354.8874 | -73959.2171 | 1.0635 | -1172.5059 | -26385.6967 |
| MYC | 18.0175 | 3.6584 | 1.9752 | 1.1233 | 20.4798 | 2.9695 |
| DNMT3B | -524.7504 | -587.0649 | -620.0635 | -1.3998 | -1882.1999 | -379.1555 |
| TDGF1 | -10376.3437 | -97473.9985 | -147925.7624 | 2.0828 | -3692.1045 | -108329.8784 |
| ZFP42 | -404.7642 | -17465.8542 | -34024.1991 | 2.5127 | -300.9286 | -19411.0624 |
| FOXD3 | -16.8791 | -87.2503 | -25186.4611 | 1.1603 | -27.4987 | -253.8663 |
| TERF1 | -9.8625 | -51.9206 | -35.8607 | -1.3104 | -13.0823 | -45.0427 |
| FGF2 | 4.56 | -2.7123 | -1.0326 | -1.0317 | 2.2038 | -4.1692 |
| GDF3 | -45.9664 | -2275.907 | -1768.1588 | 5.4474 | -322.8052 | -2529.3795 |
| ALPL | -2.5598 | -58.2752 | -5.5297 | 1.8315 | -4.0143 | -55.4878 |
| GPC4 | -34.8886 | -260.8584 | -9.7635 | 1.6672 | -56.7443 | -463.5718 |
| NASP | -2.7637 | -11.3726 | -21.1043 | -1.1115 | -2.8155 | -4.1791 |
| NOG | 5.6681 | -1.8703 | 1.5515 | 2.3787 | 3.3014 | -4.3516 |
| NODAL | -3.4486 | -17.0864 | -308.4969 | 2.8274 | -3.9689 | -25.6223 |
| SFRS18 | 1.1262 | -10.1045 | -4.6716 | 1.5931 | -1.5466 | -13.7997 |
| CCNB1 | -9.0639 | -114.4991 | -14.5063 | -1.0776 | -36.9024 | -84.4751 |
| CECR1 | -15.8923 | -158.115 | -28.9911 | 1.0816 | -6.0828 | -20.3332 |
| ELOVL6 | 1.0698 | -5.7562 | -21.6811 | 1.2554 | -2.6641 | -18.0337 |
| IGF2BP3 | -30.5077 | -427.35 | -795.5703 | 1.1404 | -316.425 | -1721.6162 |
| ACVR1B | 2.2802 | -3.4195 | -3.9217 | 1.7939 | 1.0165 | -4.3537 |
| ACVR2B | -5.624 | -61.4397 | -78.2321 | 1.5664 | -8.1932 | -70.8696 |
| PDPN | 2.2415 | -42857.5894 | -18.041 | 1.0715 | 2.2405 | -56020.1979 |
| TCF4 | -2.3922 | -555.9296 | -2.1029 | 1.003 | -1.8667 | -90.8763 |
| KLF7 | 7.2873 | 1.085 | 2.0631 | 2.0407 | 4.1225 | -1.8154 |
| FZD3 | -2.6122 | -11.4238 | -35.2942 | 1.283 | -6.3956 | -21.2533 |
| DLK1 | -1.815 | -84706.2698 | -1554.57 | 3.0176 | -2.5229 | -94140.1815 |
| EPHA4 | -3.6775 | -2.5249 | -3.4168 | 1.0082 | -11.1589 | -4.7404 |
| GPR177 | -1.7432 | -5.9512 | -1.9934 | 2.2536 | 1.7464 | -3.0973 |
| TBX3 | 10.4306 | 51.6909 | 19.8335 | 6.7959 | 11.7918 | 273.5042 |
| CD24 | 1.6665 | -12.9041 | -2872.537 | -1.056 | -1.6382 | -11.6289 |
| ITGB1/CD29 | 3.7538 | -1.0256 | 4.1717 | 1.6152 | 2.1022 | -1.5154 |
| ITGA6/CD49f | -1.3031 | -4.96 | -8.2544 | -1.0181 | -1.1453 | -4.7376 |
| EPCAM | 1.5712 | 1.0974 | -51507.5205 | -1.1378 | 1.8382 | 1.3068 |
| NT5E | 168.1036 | 2.8506 | 148.0815 | 2.2839 | 115.9066 | 2.4677 |
| PTGS2 | 3064.2014 | 77.9873 | 78.4278 | 2.2393 | 2435.8191 | 112.5123 |
| THY1 | -429.7627 | -384.9486 | 1.8475 | 1.5257 | -465.6125 | -231.7939 |
| BMI1 | 8.1935 | -1.8857 | 2.5938 | -1.0342 | 4.2588 | -3.5666 |
| CD44 | 423.334 | 184.7444 | 72.7072 | 2.2019 | 237.5521 | 311.5995 |
| TP63 | 10.9197 | 1.5061 | 4.699 | -1.0621 | 103.4881 | 3.6988 |
| GAPDH | 1 | 1 | 1 | 1 | 1 | 1 |

Fig. 15

Lineage Negative CD73/CD90 profiles for 10 women (% CELLS)

| Samples | CD73+CD90- | CD73+CD90+ | CD73-CD90- | CD73-CD90+ | Age | Ethnicity |
|---|---|---|---|---|---|---|
| Sample 1 | 4.48 | 0.69 | 90.96 | 3.86 | 38y | Caucasian |
| Sample 2 | 6.3 | 1.61 | 83.24 | 8.65 | 24y | Caucasian |
| Sample 3 | 7.45 | 0.46 | 88.7 | 3.32 | 37y | Caucasian |
| Sample 4 | 5.84 | 0.57 | 81.39 | 12.03 | 49y | Caucasian |
| Sample 5 | 6.05 | 1.27 | 89.16 | 3.46 | 49y | Caucasian |
| Sample 6 | 2.31 | 3.72 | 79.53 | 14.28 | 29y | Unknown |
| Sample 7 | 3.87 | 3.17 | 82.15 | 10.81 | 38y | Caucasian |
| Sample 8 | 3.12 | 1.72 | 83.86 | 11.31 | 46y | African-American |
| Sample 9 | 6.3 | 3.75 | 79.05 | 10.89 | 39y | African-American |
| Sample 10 | 6.83 | 1.85 | 87.51 | 3.81 | 35y | African-American |
| AVERAGE | 5.255 | 1.881 | 84.555 | 8.242 | | |
| SEM | (+/- 0.539) | (+/- 0.397) | (+/- 1.34) | (+/- 1.333) | | |

Fig. 33

43 GENE SIGNATURE

Up-Down Regulation (comparing to control group) control group is H9, human ESC

| Symbol | CD73+CD90- (R1) | CD73+CD90+ (R2) | CD73-CD90- (R3) | CD73-CD90+ (R4) | H7, human ESC | R1 colony on feeder | R1 colony in media | Human MSC |
|---|---|---|---|---|---|---|---|---|
| POU5F1/Oct3/4 | -14.0719 | -32.0788 | -72.2903 | -4477.9229 | 1.5577 | 1.1308 | -1.0139 | -189.8771 |
| NANOG | -1.5801 | -24.2126 | -257.0327 | -767.109 | 1.8903 | -1.1764 | -4.8782 | -7.8984 |
| SOX2 | -1753.6759 | -193736.0625 | -144687.0223 | -160167.1768 | -1.1139 | 1.081 | -4.2192 | -220559.634 |
| KLF4 | 155.6487 | 114.5429 | -4.4011 | -19.9505 | 1.0151 | 3.2317 | 29.9724 | 6.5708 |
| LIN28 | -484.1793 | -2279.9865 | -67027.9102 | -239439.3237 | 1.0635 | -1.0766 | -2422.1913 | -73959.2171 |
| MYC | 28.3485 | 9.4217 | -6.6577 | -32.3242 | 1.1233 | 2.7494 | 1.1993 | 1.9752 |
| DNMT3B | -189.0365 | -1767.1065 | -1153.8413 | -10806.8261 | -1.3998 | -277.5748 | -559.0382 | -620.0635 |
| TDGF1 | -2433.5324 | -176538.0123 | -131843.0807 | -145949.0539 | 2.0828 | 1.0309 | -4.6408 | -147925.762 |
| ZFP42 | -152.7086 | -617.2584 | -23945.4305 | -26507.367 | 2.5127 | 2.6594 | -1.2436 | -34024.1991 |
| FOXD3 | -17.4192 | -40.1402 | -16565.0641 | -18337.3706 | 1.1603 | 1.19 | -2.1319 | -25186.4611 |
| TERF1 | -1.7035 | -8.8613 | -170.4159 | -1573.3264 | -1.3104 | -4.1764 | -3.3034 | -35.8607 |
| FGF2 | 3.5237 | 4.7345 | -49.9076 | -525.6914 | -1.0317 | 1.4117 | 1.1973 | -1.0326 |
| GDF3 | -65.9048 | -142.3725 | -3377.3032 | -3738.643 | 5.4474 | 3.4594 | -8480.2414 | -1768.1588 |
| ALPL | -4.8333 | -12.1231 | -135.7874 | -8509.7862 | 1.8315 | 1.3294 | -80.6607 | -5.5297 |
| GPC4 | -33.2307 | -69.3361 | -344.3033 | -86.2856 | 1.6672 | -104.8376 | -272.3132 | -9.7635 |
| NASP | -2.8415 | -3.8561 | -408.9423 | -13571.0628 | -1.1115 | -2.0181 | -4.9111 | -21.1043 |
| NOG | 2.2613 | -1.787 | -12.0495 | -19.9431 | 2.3287 | 1.5511 | 2.0137 | 1.5515 |
| NODAL | -5.1792 | -12.0491 | -22.2276 | -255.3297 | 2.8274 | 2.286 | 3.6565 | -308.4969 |
| SFRS18 | -1.1178 | -1.4649 | -18.7038 | -1760.3677 | 1.5931 | -5.4718 | -4.262 | -4.6716 |
| CCNB1 | -17.2787 | -44.7756 | -196.9689 | -956.1661 | -1.0776 | -2.7103 | -10.2494 | -14.5063 |
| CECR1 | -14.3003 | -289.933 | -122.9963 | -1554.819 | 1.0816 | -1.392 | -4.4729 | -28.9911 |
| ELOVL6 | 1.5256 | -8.2989 | -50.9893 | -614.9722 | 1.2554 | -1.6872 | -1.3643 | -21.6811 |
| IGF2BP3 | -51.5242 | -110.7085 | -904.7671 | -88279.7062 | 1.1404 | -1.8708 | -1.6788 | -795.5703 |
| ACVR1B | 1.4099 | 1.0302 | -9.174 | -90.0337 | 1.7939 | -1.1266 | -1.3143 | -3.9217 |
| ACVR2B | -3.1488 | -12.2352 | -84.2237 | -2010.583 | 1.5664 | -1.1983 | -1.9352 | -78.2321 |
| PDPN | 1.8235 | 2.5163 | -65920.1848 | -49.4139 | 1.0715 | -1.2143 | -1.107 | -18.041 |
| TCF4 | -2.7199 | -1.1601 | -306.5645 | -500.8639 | 1.003 | -1.0656 | 1.9468 | -2.1029 |
| KLF7 | 9.0779 | 3.8811 | -108.8252 | -714.1375 | 2.0407 | 2.4863 | 2.5047 | 2.0631 |
| FZD3 | -3.5941 | -5.5045 | -27.3012 | -299.6919 | 1.283 | 1.6005 | -3.0759 | -35.2942 |
| DLK1 | 1.3937 | -2.6576 | -117969.7615 | -130591.4196 | 3.0176 | 1.3303 | -449.9853 | -1554.57 |
| EPHA4 | -22.8027 | -13.0844 | -10.7755 | -93.6276 | 1.0082 | 1.4696 | -25.3943 | -3.4168 |
| GPR177 | -1.4934 | -1.7594 | 1.3215 | 2.612 | 2.2536 | 2.2027 | 2.8421 | -1.9934 |
| TBX3 | 70.1724 | 4.0387 | -1.1163 | -6.0979 | 6.7959 | 9.7257 | 209.5631 | 19.8335 |
| CD24 | -1.0858 | -32.6774 | -26.5911 | -21.883 | -1.056 | 1.0416 | -3.2035 | -2872.537 |
| ITGB1/CD29 | 2.5123 | 2.4342 | -2.8067 | -1.0584 | 1.6152 | 2.5575 | 3.1114 | 4.1717 |
| ITGA6/CD49f | 1.1815 | -19.0838 | -5.9053 | -21.7245 | -1.0181 | 1.6386 | -1.2969 | -8.2544 |
| EPCAM | 1.9162 | -5.9174 | -1.1105 | -352.9091 | -1.1378 | -1.4099 | -30.0874 | -51507.5205 |
| NT5E | 61.3825 | 51.5811 | -2.0418 | -3.2351 | 2.2839 | 781.9396 | 877.0896 | 148.0815 |
| PTGS2 | 459.6302 | 2235.3536 | 40.6921 | 30.4194 | 2.2393 | 127.8287 | 23.7615 | 78.4278 |
| THY1 | -822.9647 | -57.9811 | -597.8905 | -1.3926 | 1.5257 | -343144.065 | -1548.8985 | 1.8475 |
| BMI1 | 6.6017 | 5.3605 | -4.499 | -1645.4111 | -1.0342 | 3.519 | 5.6859 | 2.5938 |
| CD44 | 76.8007 | 68.8199 | 101.4613 | 333.5386 | 2.2019 | 60.8748 | 89.9664 | 72.7072 |
| TP63 | 19.6766 | 134.7724 | 7.119 | 4600.312 | -1.0621 | 26.433 | 9.0215 | 4.699 |

Fig. 34

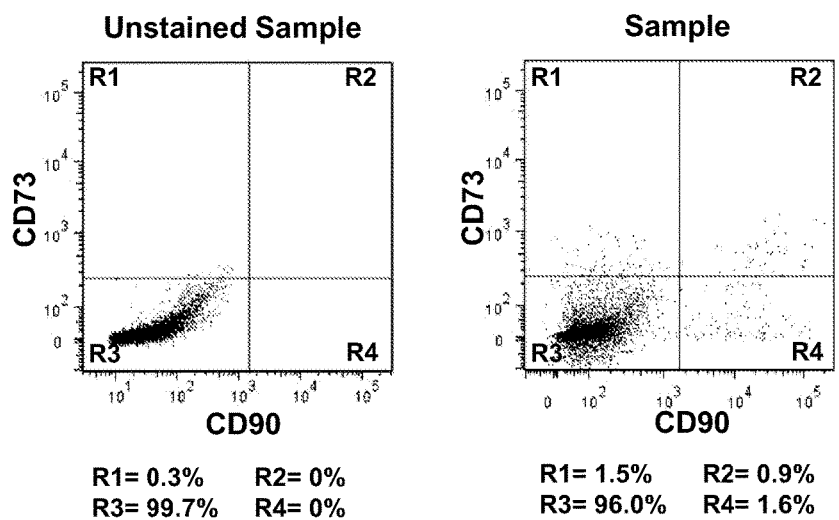
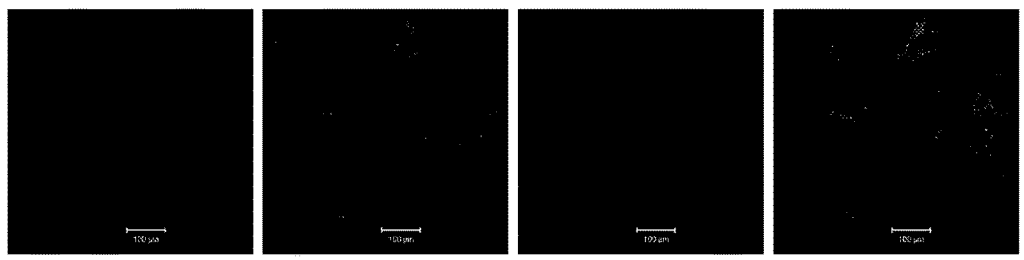
Fig. 35

SEQUENCE LISTING

<160> NUMBER OF SEQ ID NOS: 17

<210> SEQ ID NO 1
<211> LENGTH: 479
<212> TYPE: PRT
<213> ORGANISM: Homo sapiens

<400> SEQUENCE: 1

```
Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
    290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365
```

```
Met Pro Pro Gly Ser Cys Met Pro Glu Glu Pro Lys Pro Arg Gly
    370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
                420                 425                 430

Cys Gly Trp Lys Phe Ala Arg Ser Asp Glu Leu Thr Arg His Tyr Arg
            435                 440                 445

Lys His Thr Gly His Arg Pro Phe Gln Cys Gln Lys Cys Asp Arg Ala
    450                 455                 460

Phe Ser Arg Ser Asp His Leu Ala Leu His Met Lys Arg His Phe
465                 470                 475

<210> SEQ ID NO 2
<211> LENGTH: 454
<212> TYPE: PRT
<213> ORGANISM: Homo sapiens

<400> SEQUENCE: 2

Met Asp Phe Phe Arg Val Val Glu Asn Gln Gln Pro Pro Ala Thr Met
1               5                   10                  15

Pro Leu Asn Val Ser Phe Thr Asn Arg Asn Tyr Asp Leu Asp Tyr Asp
                20                  25                  30

Ser Val Gln Pro Tyr Phe Tyr Cys Asp Glu Glu Glu Asn Phe Tyr Gln
            35                  40                  45

Gln Gln Gln Gln Ser Glu Leu Gln Pro Pro Ala Pro Ser Glu Asp Ile
    50                  55                  60

Trp Lys Lys Phe Glu Leu Leu Pro Thr Pro Pro Leu Ser Pro Ser Arg
65                  70                  75                  80

Arg Ser Gly Leu Cys Ser Pro Ser Tyr Val Ala Val Thr Pro Phe Ser
                85                  90                  95

Leu Arg Gly Asp Asn Asp Gly Gly Gly Gly Ser Phe Ser Thr Ala Asp
                100                 105                 110

Gln Leu Glu Met Val Thr Glu Leu Leu Gly Gly Asp Met Val Asn Gln
            115                 120                 125

Ser Phe Ile Cys Asp Pro Asp Asp Glu Thr Phe Ile Lys Asn Ile Ile
    130                 135                 140

Ile Gln Asp Cys Met Trp Ser Gly Phe Ser Ala Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
                180                 185                 190

Leu Gln Asp Leu Ser Ala Ala Ala Ser Glu Cys Ile Asp Pro Ser Val
            195                 200                 205

Val Phe Pro Tyr Pro Leu Asn Asp Ser Ser Ser Pro Lys Ser Cys Ala
    210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Glu Gln Glu
                260                 265                 270
```

```
Asp Glu Glu Glu Ile Asp Val Ser Val Glu Lys Arg Gln Ala Pro
            275                 280                 285

Gly Lys Arg Ser Glu Ser Gly Ser Pro Ser Ala Gly Gly His Ser Lys
290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
                405                 410                 415

Tyr Ile Leu Ser Val Gln Ala Glu Glu Gln Lys Leu Ile Ser Glu Glu
            420                 425                 430

Asp Leu Leu Arg Lys Arg Arg Glu Gln Leu Lys His Lys Leu Glu Gln
            435                 440                 445

Leu Arg Asn Ser Cys Ala
        450

<210> SEQ ID NO 3
<211> LENGTH: 190
<212> TYPE: PRT
<213> ORGANISM: Homo sapiens

<400> SEQUENCE: 3

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
            20                  25                  30

Leu Leu Gln Lys Trp Val Glu Glu Ala Asp Asn Asn Glu Asn Leu Gln
        35                  40                  45

Glu Ile Cys Lys Ala Glu Thr Leu Val Gln Ala Arg Lys Arg Lys Arg
    50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
            100                 105                 110

Gln Lys Gly Lys Arg Ser Ser Asp Tyr Ala Gln Arg Glu Asp Phe
            115                 120                 125

Glu Ala Ala Gly Ser Pro Phe Ser Gly Gly Pro Val Ser Phe Pro Leu
130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
```

<210> SEQ ID NO 4
<211> LENGTH: 360
<212> TYPE: PRT
<213> ORGANISM: Homo sapiens

<400> SEQUENCE: 4

Met Ala Gly His Leu Ala Ser Asp Phe Ala Phe Ser Pro Pro Pro Gly
1               5                   10                  15

Gly Gly Gly Asp Gly Pro Gly Pro Glu Pro Gly Trp Val Asp Pro
            20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu Ser Gln Asp Ile Lys Ala Leu Gln Lys
130                 135                 140

Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
            195                 200                 205

Glu Glu Ala Asp Asn Asn Glu Asn Leu Gln Glu Ile Cys Lys Ala Glu
            210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
            355                 360

<210> SEQ ID NO 5
<211> LENGTH: 190
<212> TYPE: PRT
<213> ORGANISM: Homo sapiens

<400> SEQUENCE: 5

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
                20                  25                  30

Leu Leu Gln Lys Trp Val Glu Ala Asp Asn Asn Glu Asn Leu Gln
            35                  40                  45

Glu Ile Cys Lys Ala Glu Thr Leu Val Gln Ala Arg Lys Arg Lys Arg
50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
            100                 105                 110

Gln Lys Gly Lys Arg Ser Ser Ser Asp Tyr Ala Gln Arg Glu Asp Phe
        115                 120                 125

Glu Ala Ala Gly Ser Pro Phe Ser Gly Gly Pro Val Ser Phe Pro Leu
130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
            180                 185                 190

<210> SEQ ID NO 6
<211> LENGTH: 305
<212> TYPE: PRT
<213> ORGANISM: Homo sapiens

<400> SEQUENCE: 6

Met Ser Val Asp Pro Ala Cys Pro Gln Ser Leu Pro Cys Phe Glu Ala
1               5                   10                  15

Ser Asp Cys Lys Glu Ser Ser Pro Met Pro Val Ile Cys Gly Pro Glu
                20                  25                  30

Glu Asn Tyr Pro Ser Leu Gln Met Ser Ser Ala Glu Met Pro His Thr
            35                  40                  45

Glu Thr Val Ser Pro Leu Pro Ser Ser Met Asp Leu Leu Ile Gln Asp
50                  55                  60

Ser Pro Asp Ser Ser Thr Ser Pro Lys Gly Lys Gln Pro Thr Ser Ala
65                  70                  75                  80

Glu Lys Ser Val Ala Lys Lys Glu Asp Lys Val Pro Val Lys Lys Gln
                85                  90                  95

Lys Thr Arg Thr Val Phe Ser Ser Thr Gln Leu Cys Val Leu Asn Asp
            100                 105                 110

Arg Phe Gln Arg Gln Lys Tyr Leu Ser Leu Gln Gln Met Gln Glu Leu
        115                 120                 125

Ser Asn Ile Leu Asn Leu Ser Tyr Lys Gln Val Lys Thr Trp Phe Gln
130                 135                 140

Asn Gln Arg Met Lys Ser Lys Arg Trp Gln Lys Asn Asn Trp Pro Lys
145                 150                 155                 160

Asn Ser Asn Gly Val Thr Gln Lys Ala Ser Ala Pro Thr Tyr Pro Ser
                165                 170                 175

Leu Tyr Ser Ser Tyr His Gln Gly Cys Leu Val Asn Pro Thr Gly Asn
            180                 185                 190

Leu Pro Met Trp Ser Asn Gln Thr Trp Asn Asn Ser Thr Trp Ser Asn
        195                 200                 205

Gln Thr Gln Asn Ile Gln Ser Trp Ser Asn His Ser Trp Asn Thr Gln
    210                 215                 220

Thr Trp Cys Thr Gln Ser Trp Asn Asn Gln Ala Trp Asn Ser Pro Phe
225                 230                 235                 240

Tyr Asn Cys Gly Glu Glu Ser Leu Gln Ser Cys Met Gln Phe Gln Pro
                245                 250                 255

Asn Ser Pro Ala Ser Asp Leu Glu Ala Ala Leu Glu Ala Ala Gly Glu
            260                 265                 270

Gly Leu Asn Val Ile Gln Gln Thr Thr Arg Tyr Phe Ser Thr Pro Gln
        275                 280                 285

Thr Met Asp Leu Phe Leu Asn Tyr Ser Met Asn Met Gln Pro Glu Asp
    290                 295                 300

Val
305

<210> SEQ ID NO 7
<211> LENGTH: 80
<212> TYPE: PRT
<213> ORGANISM: Homo sapiens

<400> SEQUENCE: 7

Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
        35                  40                  45

Asn Pro Thr Asn Ala Thr Thr Lys Ala Ala Gly Gly Ala Leu Gln Ser
    50                  55                  60

Thr Ala Ser Leu Phe Val Val Ser Leu Ser Leu Leu His Leu Tyr Ser
65                  70                  75                  80

<210> SEQ ID NO 8
<211> LENGTH: 314
<212> TYPE: PRT
<213> ORGANISM: Homo sapiens

<400> SEQUENCE: 8

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
            85                  90                  95

Pro Asp Cys Asp Glu Ser Gly Leu Phe Lys Ala Lys Gln Cys Asn Gly
            100                 105                 110

Thr Ser Met Cys Trp Cys Val Asn Thr Ala Gly Val Arg Arg Thr Asp
            115                 120                 125

Lys Asp Thr Glu Ile Thr Cys Ser Glu Arg Val Arg Thr Tyr Trp Ile
130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
            165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
            195                 200                 205

Ile Ala Asp Val Ala Tyr Tyr Phe Glu Lys Asp Val Lys Gly Glu Ser
            210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
            245                 250                 255

Pro Glu Phe Ser Met Gln Gly Leu Lys Ala Gly Val Ile Ala Val Ile
            260                 265                 270

Val Val Val Val Ile Ala Val Val Ala Gly Ile Val Val Leu Val Ile
            275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 9
<211> LENGTH: 511
<212> TYPE: PRT
<213> ORGANISM: Homo sapiens

<400> SEQUENCE: 9

Met Leu Val Asp Gly Pro Ser Glu Arg Pro Ala Leu Cys Phe Leu Leu
1               5                   10                  15

Leu Ala Val Ala Met Ser Phe Phe Gly Ser Ala Leu Ser Ile Asp Glu
            20                  25                  30

Thr Arg Ala His Leu Leu Leu Lys Glu Lys Met Met Arg Leu Gly Gly
            35                  40                  45

Arg Leu Val Leu Asn Thr Lys Glu Glu Leu Ala Asn Glu Arg Leu Met
        50                  55                  60

Thr Leu Lys Ile Ala Glu Met Lys Glu Ala Met Arg Thr Leu Ile Phe
65                  70                  75                  80

Pro Pro Ser Met His Phe Phe Gln Ala Lys His Leu Ile Glu Arg Ser
            85                  90                  95

Gln Val Phe Asn Ile Leu Arg Met Met Pro Lys Gly Ala Ala Leu His
            100                 105                 110

Leu His Asp Ile Gly Ile Val Thr Met Asp Trp Leu Val Arg Asn Val
            115                 120                 125

Thr Tyr Arg Pro His Cys His Ile Cys Phe Thr Pro Arg Gly Ile Met
            130                 135                 140

-continued

```
Gln Phe Arg Phe Ala His Pro Thr Pro Arg Pro Ser Glu Lys Cys Ser
145                 150                 155                 160

Lys Trp Ile Leu Leu Glu Asp Tyr Arg Lys Arg Val Gln Asn Val Thr
            165                 170                 175

Glu Phe Asp Asp Ser Leu Leu Arg Asn Phe Thr Leu Val Thr Gln His
        180                 185                 190

Pro Glu Val Ile Tyr Thr Asn Gln Asn Val Val Trp Ser Lys Phe Glu
    195                 200                 205

Thr Ile Phe Phe Thr Ile Ser Gly Leu Ile His Tyr Ala Pro Val Phe
210                 215                 220

Arg Asp Tyr Val Phe Arg Ser Met Gln Glu Phe Tyr Glu Asp Asn Val
225                 230                 235                 240

Leu Tyr Met Glu Ile Arg Ala Arg Leu Leu Pro Val Tyr Glu Leu Ser
            245                 250                 255

Gly Glu His His Asp Glu Glu Trp Ser Val Lys Thr Tyr Gln Glu Val
        260                 265                 270

Ala Gln Lys Phe Val Glu Thr His Pro Glu Phe Ile Gly Ile Lys Ile
    275                 280                 285

Ile Tyr Ser Asp His Arg Ser Lys Asp Val Ala Val Ile Ala Glu Ser
290                 295                 300

Ile Arg Met Ala Met Gly Leu Arg Ile Lys Phe Pro Thr Val Val Ala
305                 310                 315                 320

Gly Phe Asp Leu Val Gly His Glu Asp Thr Gly His Ser Leu His Asp
            325                 330                 335

Tyr Lys Glu Ala Leu Met Ile Pro Ala Lys Asp Gly Val Lys Leu Pro
        340                 345                 350

Tyr Phe Phe His Ala Gly Glu Thr Asp Trp Gln Gly Thr Ser Ile Asp
    355                 360                 365

Arg Asn Ile Leu Asp Ala Leu Met Leu Asn Thr Thr Arg Ile Gly His
370                 375                 380

Gly Phe Ala Leu Ser Lys His Pro Ala Val Arg Thr Tyr Ser Trp Lys
385                 390                 395                 400

Lys Asp Ile Pro Ile Glu Val Cys Pro Ile Ser Asn Gln Val Leu Lys
            405                 410                 415

Leu Val Ser Asp Leu Arg Asn His Pro Val Ala Thr Leu Met Ala Thr
        420                 425                 430

Gly His Pro Met Val Ile Ser Ser Asp Asp Pro Ala Met Phe Gly Ala
    435                 440                 445

Lys Gly Leu Ser Tyr Asp Phe Tyr Glu Val Phe Met Gly Ile Gly Gly
450                 455                 460

Met Lys Ala Asp Leu Arg Thr Leu Lys Gln Leu Ala Met Asn Ser Ile
465                 470                 475                 480

Lys Tyr Ser Thr Leu Leu Glu Ser Glu Lys Asn Thr Phe Met Glu Ile
            485                 490                 495

Trp Lys Lys Arg Trp Asp Lys Phe Ile Ala Asp Val Ala Thr Lys
        500                 505                 510

<210> SEQ ID NO 10
<211> LENGTH: 270
<212> TYPE: PRT
<213> ORGANISM: Homo sapiens

<400> SEQUENCE: 10

Met Asp Ser Leu Glu Trp Asn Trp Ala Leu Val Tyr Glu Leu Ser Gly
```

```
  1               5                   10                  15
Glu His His Asp Glu Glu Trp Ser Val Lys Thr Tyr Gln Glu Val Ala
                20                  25                  30

Gln Lys Phe Val Glu Thr His Pro Glu Phe Ile Gly Ile Lys Ile Ile
                35                  40                  45

Tyr Ser Asp His Arg Ser Lys Asp Val Ala Val Ile Ala Glu Ser Ile
        50                  55                  60

Arg Met Ala Met Gly Leu Arg Ile Lys Phe Pro Thr Val Val Ala Gly
65                  70                  75                  80

Phe Asp Leu Val Gly His Glu Asp Thr Gly His Ser Leu His Asp Tyr
                    85                  90                  95

Lys Glu Ala Leu Met Ile Pro Ala Lys Asp Gly Val Lys Leu Pro Tyr
                100                 105                 110

Phe Phe His Ala Gly Glu Thr Asp Trp Gln Gly Thr Ser Ile Asp Arg
                115                 120                 125

Asn Ile Leu Asp Ala Leu Met Leu Asn Thr Thr Arg Ile Gly His Gly
        130                 135                 140

Phe Ala Leu Ser Lys His Pro Ala Val Arg Thr Tyr Ser Trp Lys Lys
145                 150                 155                 160

Asp Ile Pro Ile Glu Val Cys Pro Ile Ser Asn Gln Val Leu Lys Leu
                165                 170                 175

Val Ser Asp Leu Arg Asn His Pro Val Ala Thr Leu Met Ala Thr Gly
                180                 185                 190

His Pro Met Val Ile Ser Ser Asp Asp Pro Ala Met Phe Gly Ala Lys
                195                 200                 205

Gly Leu Ser Tyr Asp Phe Tyr Glu Val Phe Met Gly Ile Gly Gly Met
        210                 215                 220

Lys Ala Asp Leu Arg Thr Leu Lys Gln Leu Ala Met Asn Ser Ile Lys
225                 230                 235                 240

Tyr Ser Thr Leu Leu Glu Ser Glu Lys Asn Thr Phe Met Glu Ile Trp
                245                 250                 255

Lys Lys Arg Trp Asp Lys Phe Ile Ala Asp Val Ala Thr Lys
                260                 265                 270

<210> SEQ ID NO 11
<211> LENGTH: 845
<212> TYPE: PRT
<213> ORGANISM: Homo sapiens

<400> SEQUENCE: 11

Met Glu Pro Ser Pro Glu Pro Pro Ser Leu Glu Ser Met Lys Gly Asp
1               5                   10                  15

Thr Arg His Leu Asn Gly Glu Glu Asp Ala Gly Gly Arg Glu Asp Ser
                20                  25                  30

Ile Leu Val Asn Gly Ala Cys Ser Asp Gln Ser Ser Asp Ser Pro Pro
        35                  40                  45

Ile Leu Glu Ala Ile Arg Thr Pro Glu Ile Arg Gly Arg Arg Ser Ser
        50                  55                  60

Ser Arg Leu Ser Lys Arg Glu Val Ser Ser Leu Leu Ser Tyr Thr Gln
65                  70                  75                  80

Asp Leu Thr Gly Asp Gly Asp Gly Glu Asp Gly Asp Gly Ser Asp Thr
                    85                  90                  95

Pro Val Met Pro Lys Leu Phe Arg Glu Thr Arg Thr Arg Ser Glu Ser
                100                 105                 110
```

Pro Ala Val Arg Thr Arg Asn Asn Asn Ser Val Ser Ser Arg Glu Arg
            115                 120                 125

His Arg Pro Ser Pro Arg Ser Thr Arg Gly Arg Gln Gly Arg Asn His
        130                 135                 140

Val Asp Glu Ser Pro Val Glu Phe Pro Ala Thr Arg Ser Leu Arg Arg
145                 150                 155                 160

Arg Ala Thr Ala Ser Ala Gly Thr Pro Trp Pro Ser Pro Pro Ser Ser
                165                 170                 175

Tyr Leu Thr Ile Asp Leu Thr Asp Asp Thr Glu Asp Thr His Gly Thr
            180                 185                 190

Pro Gln Ser Ser Ser Thr Pro Tyr Ala Arg Leu Ala Gln Asp Ser Gln
        195                 200                 205

Gln Gly Gly Met Glu Ser Pro Gln Val Glu Ala Asp Ser Gly Asp Gly
    210                 215                 220

Asp Ser Ser Glu Tyr Gln Asp Gly Lys Glu Phe Gly Ile Gly Asp Leu
225                 230                 235                 240

Val Trp Gly Lys Ile Lys Gly Phe Ser Trp Trp Pro Ala Met Val Val
                245                 250                 255

Ser Trp Lys Ala Thr Ser Lys Arg Gln Ala Met Ser Gly Met Arg Trp
            260                 265                 270

Val Gln Trp Phe Gly Asp Gly Lys Phe Ser Glu Val Ser Ala Asp Lys
        275                 280                 285

Leu Val Ala Leu Gly Leu Phe Ser Gln His Phe Asn Leu Ala Thr Phe
    290                 295                 300

Asn Lys Leu Val Ser Tyr Arg Lys Ala Met Tyr His Ala Leu Glu Lys
305                 310                 315                 320

Ala Arg Val Arg Ala Gly Lys Thr Phe Pro Ser Ser Pro Gly Asp Ser
                325                 330                 335

Leu Glu Asp Gln Leu Lys Pro Met Leu Glu Trp Ala His Gly Gly Phe
            340                 345                 350

Lys Pro Thr Gly Ile Glu Gly Leu Lys Pro Asn Asn Thr Gln Pro Glu
        355                 360                 365

Asn Lys Thr Arg Arg Arg Thr Ala Asp Asp Ser Ala Thr Ser Asp Tyr
    370                 375                 380

Cys Pro Ala Pro Lys Arg Leu Lys Thr Asn Cys Tyr Asn Asn Gly Lys
385                 390                 395                 400

Asp Arg Gly Asp Glu Asp Gln Ser Arg Glu Gln Met Ala Ser Asp Val
                405                 410                 415

Ala Asn Asn Lys Ser Ser Leu Glu Asp Gly Cys Leu Ser Cys Gly Arg
            420                 425                 430

Lys Asn Pro Val Ser Phe His Pro Leu Phe Glu Gly Gly Leu Cys Gln
        435                 440                 445

Thr Cys Arg Asp Arg Phe Leu Glu Leu Phe Tyr Met Tyr Asp Asp Asp
    450                 455                 460

Gly Tyr Gln Ser Tyr Cys Thr Val Cys Cys Glu Gly Arg Glu Leu Leu
465                 470                 475                 480

Leu Cys Ser Asn Thr Ser Cys Cys Arg Cys Phe Cys Val Glu Cys Leu
                485                 490                 495

Glu Val Leu Val Gly Thr Gly Thr Ala Ala Glu Ala Lys Leu Gln Glu
            500                 505                 510

Pro Trp Ser Cys Tyr Met Cys Leu Pro Gln Arg Cys His Gly Val Leu
        515                 520                 525

Arg Arg Arg Lys Asp Trp Asn Val Arg Leu Gln Ala Phe Phe Thr Ser

```
            530                 535                 540
Asp Thr Gly Leu Glu Tyr Glu Ala Pro Lys Leu Tyr Pro Ala Ile Pro
545                 550                 555                 560

Ala Ala Arg Arg Arg Pro Ile Arg Val Leu Ser Leu Phe Asp Gly Ile
                565                 570                 575

Ala Thr Gly Tyr Leu Val Leu Lys Glu Leu Gly Ile Lys Val Gly Lys
            580                 585                 590

Tyr Val Ala Ser Glu Val Cys Glu Ser Ile Ala Val Gly Thr Val
        595                 600                 605

Lys His Glu Gly Asn Ile Lys Tyr Val Asn Asp Val Arg Asn Ile Thr
        610                 615                 620

Lys Lys Asn Ile Glu Glu Trp Gly Pro Phe Asp Leu Val Ile Gly Gly
625                 630                 635                 640

Ser Pro Cys Asn Asp Leu Ser Asn Val Asn Pro Ala Arg Lys Gly Leu
                645                 650                 655

Tyr Glu Gly Thr Gly Arg Leu Phe Phe Glu Phe Tyr His Leu Leu Asn
                660                 665                 670

Tyr Ser Arg Pro Lys Glu Gly Asp Asp Arg Pro Phe Phe Trp Met Phe
        675                 680                 685

Glu Asn Val Val Ala Met Lys Val Gly Asp Lys Arg Asp Ile Ser Arg
        690                 695                 700

Phe Leu Glu Cys Asn Pro Val Met Ile Asp Ala Ile Lys Val Ser Ala
705                 710                 715                 720

Ala His Arg Ala Arg Tyr Phe Trp Gly Asn Leu Pro Gly Met Asn Arg
                725                 730                 735

Pro Val Ile Ala Ser Lys Asn Asp Lys Leu Glu Leu Gln Asp Cys Leu
                740                 745                 750

Glu Tyr Asn Arg Ile Ala Lys Leu Lys Lys Val Gln Thr Ile Thr Thr
        755                 760                 765

Lys Ser Asn Ser Ile Lys Gln Gly Lys Asn Gln Leu Phe Pro Val Val
        770                 775                 780

Met Asn Gly Lys Glu Asp Val Leu Trp Cys Thr Glu Leu Glu Arg Ile
785                 790                 795                 800

Phe Gly Phe Pro Val His Tyr Thr Asp Val Ser Asn Met Gly Arg Gly
                805                 810                 815

Ala Arg Gln Lys Leu Leu Gly Arg Ser Trp Ser Val Pro Val Ile Arg
                820                 825                 830

His Leu Phe Ala Pro Leu Lys Asp Tyr Phe Ala Cys Glu
        835                 840                 845

<210> SEQ ID NO 12
<211> LENGTH: 770
<212> TYPE: PRT
<213> ORGANISM: Homo sapiens

<400> SEQUENCE: 12

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
                20                  25                  30

Asp Ser Pro Pro Ile Leu Glu Ala Ile Arg Thr Pro Glu Ile Arg Gly
            35                  40                  45

Arg Arg Ser Ser Ser Arg Leu Ser Lys Arg Glu Val Ser Ser Leu Leu
        50                  55                  60
```

```
Ser Tyr Thr Gln Asp Leu Thr Gly Asp Gly Asp Gly Glu Asp Gly Asp
 65                  70                  75                  80

Gly Ser Asp Thr Pro Val Met Pro Lys Leu Phe Arg Glu Thr Arg Thr
                 85                  90                  95

Arg Ser Glu Ser Pro Ala Val Arg Thr Arg Asn Asn Asn Ser Val Ser
            100                 105                 110

Ser Arg Glu Arg His Arg Pro Ser Pro Arg Ser Thr Arg Gly Arg Gln
        115                 120                 125

Gly Arg Asn His Val Asp Glu Ser Pro Val Glu Phe Pro Ala Thr Arg
    130                 135                 140

Ser Leu Arg Arg Arg Ala Thr Ala Ser Ala Gly Thr Pro Trp Pro Ser
145                 150                 155                 160

Pro Pro Ser Ser Tyr Leu Thr Ile Asp Leu Thr Asp Asp Thr Glu Asp
                165                 170                 175

Thr His Gly Thr Pro Gln Ser Ser Thr Pro Tyr Ala Arg Leu Ala
            180                 185                 190

Gln Asp Ser Gln Gln Gly Gly Met Glu Ser Pro Gln Val Glu Ala Asp
        195                 200                 205

Ser Gly Asp Gly Asp Ser Ser Glu Tyr Gln Asp Gly Lys Glu Phe Gly
    210                 215                 220

Ile Gly Asp Leu Val Trp Gly Lys Ile Lys Gly Phe Ser Trp Trp Pro
225                 230                 235                 240

Ala Met Val Val Ser Trp Lys Ala Thr Ser Lys Arg Gln Ala Met Ser
                245                 250                 255

Gly Met Arg Trp Val Gln Trp Phe Gly Asp Gly Lys Phe Ser Glu Val
            260                 265                 270

Ser Ala Asp Lys Leu Val Ala Leu Gly Leu Phe Ser Gln His Phe Asn
        275                 280                 285

Leu Ala Thr Phe Asn Lys Leu Val Ser Tyr Arg Lys Ala Met Tyr His
    290                 295                 300

Ala Leu Glu Lys Ala Arg Val Arg Ala Gly Lys Thr Phe Pro Ser Ser
305                 310                 315                 320

Pro Gly Asp Ser Leu Glu Asp Gln Leu Lys Pro Met Leu Glu Trp Ala
                325                 330                 335

His Gly Gly Phe Lys Pro Thr Gly Ile Glu Gly Leu Lys Pro Asn Asn
            340                 345                 350

Thr Gln Pro Glu Asn Lys Thr Arg Arg Thr Ala Asp Asp Ser Ala
        355                 360                 365

Thr Ser Asp Tyr Cys Pro Ala Pro Lys Arg Leu Lys Thr Asn Cys Tyr
    370                 375                 380

Asn Asn Gly Lys Asp Arg Gly Asp Glu Asp Gln Ser Arg Glu Gln Met
385                 390                 395                 400

Ala Ser Asp Val Ala Asn Asn Lys Ser Ser Leu Glu Asp Gly Cys Leu
                405                 410                 415

Ser Cys Gly Arg Lys Asn Pro Val Ser Phe His Pro Leu Phe Glu Gly
            420                 425                 430

Gly Leu Cys Gln Thr Cys Arg Asp Arg Phe Leu Glu Leu Phe Tyr Met
        435                 440                 445

Tyr Asp Asp Asp Gly Tyr Gln Ser Tyr Cys Thr Val Cys Cys Glu Gly
    450                 455                 460

Arg Glu Leu Leu Leu Cys Ser Asn Thr Ser Cys Cys Arg Cys Phe Cys
465                 470                 475                 480

Val Glu Cys Leu Glu Val Leu Val Gly Thr Gly Thr Ala Ala Glu Ala
```

```
            485                 490                 495
Lys Leu Gln Glu Pro Trp Ser Cys Tyr Met Cys Leu Pro Gln Arg Cys
            500                 505                 510

His Gly Val Leu Arg Arg Arg Lys Asp Trp Asn Val Arg Leu Gln Ala
            515                 520                 525

Phe Phe Thr Ser Asp Thr Gly Leu Glu Tyr Glu Ala Pro Lys Leu Tyr
    530                 535                 540

Pro Ala Ile Pro Ala Ala Arg Arg Arg Pro Ile Arg Val Leu Ser Leu
545                 550                 555                 560

Phe Asp Gly Ile Ala Thr Gly Tyr Leu Val Leu Lys Glu Leu Gly Ile
                565                 570                 575

Lys Val Gly Lys Tyr Val Ala Ser Glu Val Cys Glu Ser Ile Ala
            580                 585                 590

Val Gly Thr Val Lys His Glu Gly Asn Ile Lys Tyr Val Asn Asp Val
            595                 600                 605

Arg Asn Ile Thr Lys Lys Asn Ile Glu Glu Trp Gly Pro Phe Asp Leu
            610                 615                 620

Val Ile Gly Gly Ser Pro Cys Asn Asp Leu Ser Asn Val Asn Pro Ala
625                 630                 635                 640

Arg Lys Gly Leu Tyr Glu Gly Thr Gly Arg Leu Phe Phe Glu Phe Tyr
                645                 650                 655

His Leu Leu Asn Tyr Ser Arg Pro Lys Glu Gly Asp Asp Arg Pro Phe
            660                 665                 670

Phe Trp Met Phe Glu Asn Val Val Ala Met Lys Val Gly Asp Lys Arg
            675                 680                 685

Asp Ile Ser Arg Phe Leu Glu Cys Asn Pro Val Met Ile Asp Ala Ile
            690                 695                 700

Lys Val Ser Ala Ala His Arg Ala Arg Tyr Phe Trp Gly Asn Leu Pro
705                 710                 715                 720

Gly Met Asn Arg Ile Phe Gly Phe Pro Val His Tyr Thr Asp Val Ser
                725                 730                 735

Asn Met Gly Arg Gly Ala Arg Gln Lys Leu Leu Gly Arg Ser Trp Ser
            740                 745                 750

Val Pro Val Ile Arg His Leu Phe Ala Pro Leu Lys Asp Tyr Phe Ala
    755                 760                 765

Cys Glu
    770

<210> SEQ ID NO 13
<211> LENGTH: 833
<212> TYPE: PRT
<213> ORGANISM: Homo sapiens

<400> SEQUENCE: 13

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
            20                  25                  30

Asp Ser Pro Pro Ile Leu Glu Ala Ile Arg Thr Pro Glu Ile Arg Gly
        35                  40                  45

Arg Arg Ser Ser Ser Arg Leu Ser Lys Arg Glu Val Ser Ser Leu Leu
    50                  55                  60

Ser Tyr Thr Gln Asp Leu Thr Gly Asp Gly Asp Gly Glu Asp Gly Asp
65                  70                  75                  80
```

-continued

```
Gly Ser Asp Thr Pro Val Met Pro Lys Leu Phe Arg Glu Thr Arg Thr
                85                  90                  95
Arg Ser Glu Ser Pro Ala Val Arg Thr Arg Asn Asn Asn Ser Val Ser
            100                 105                 110
Ser Arg Glu Arg His Arg Pro Ser Pro Arg Ser Thr Arg Gly Arg Gln
        115                 120                 125
Gly Arg Asn His Val Asp Glu Ser Pro Val Glu Phe Pro Ala Thr Arg
    130                 135                 140
Ser Leu Arg Arg Arg Ala Thr Ala Ser Ala Gly Thr Pro Trp Pro Ser
145                 150                 155                 160
Pro Pro Ser Ser Tyr Leu Thr Ile Asp Leu Thr Asp Thr Glu Asp
                165                 170                 175
Thr His Gly Thr Pro Gln Ser Ser Thr Pro Tyr Ala Arg Leu Ala
            180                 185                 190
Gln Asp Ser Gln Gln Gly Gly Met Glu Ser Pro Gln Val Glu Ala Asp
        195                 200                 205
Ser Gly Asp Gly Asp Ser Ser Glu Tyr Gln Asp Gly Lys Glu Phe Gly
    210                 215                 220
Ile Gly Asp Leu Val Trp Gly Lys Ile Lys Gly Phe Ser Trp Trp Pro
225                 230                 235                 240
Ala Met Val Val Ser Trp Lys Ala Thr Ser Lys Arg Gln Ala Met Ser
                245                 250                 255
Gly Met Arg Trp Val Gln Trp Phe Gly Asp Gly Lys Phe Ser Glu Val
            260                 265                 270
Ser Ala Asp Lys Leu Val Ala Leu Gly Leu Phe Ser Gln His Phe Asn
        275                 280                 285
Leu Ala Thr Phe Asn Lys Leu Val Ser Tyr Arg Lys Ala Met Tyr His
    290                 295                 300
Ala Leu Glu Lys Ala Arg Val Arg Ala Gly Lys Thr Phe Pro Ser Ser
305                 310                 315                 320
Pro Gly Asp Ser Leu Glu Asp Gln Leu Lys Pro Met Leu Glu Trp Ala
                325                 330                 335
His Gly Gly Phe Lys Pro Thr Gly Ile Glu Gly Leu Lys Pro Asn Asn
            340                 345                 350
Thr Gln Pro Glu Asn Lys Thr Arg Arg Arg Thr Ala Asp Asp Ser Ala
        355                 360                 365
Thr Ser Asp Tyr Cys Pro Ala Pro Lys Arg Leu Lys Thr Asn Cys Tyr
    370                 375                 380
Asn Asn Gly Lys Asp Arg Gly Asp Glu Asp Gln Ser Arg Glu Gln Met
385                 390                 395                 400
Ala Ser Asp Val Ala Asn Asn Lys Ser Ser Leu Glu Asp Gly Cys Leu
                405                 410                 415
Ser Cys Gly Arg Lys Asn Pro Val Ser Phe His Pro Leu Phe Glu Gly
            420                 425                 430
Gly Leu Cys Gln Thr Cys Arg Asp Arg Phe Leu Glu Leu Phe Tyr Met
        435                 440                 445
Tyr Asp Asp Asp Gly Tyr Gln Ser Tyr Cys Thr Val Cys Cys Glu Gly
    450                 455                 460
Arg Glu Leu Leu Leu Cys Ser Asn Thr Ser Cys Cys Arg Cys Phe Cys
465                 470                 475                 480
Val Glu Cys Leu Glu Val Leu Val Gly Thr Gly Thr Ala Ala Glu Ala
                485                 490                 495
Lys Leu Gln Glu Pro Trp Ser Cys Tyr Met Cys Leu Pro Gln Arg Cys
```

```
            500                 505                 510
His Gly Val Leu Arg Arg Lys Asp Trp Asn Val Arg Leu Gln Ala
            515                 520                 525

Phe Phe Thr Ser Asp Thr Gly Leu Glu Tyr Glu Ala Pro Lys Leu Tyr
            530                 535                 540

Pro Ala Ile Pro Ala Ala Arg Arg Pro Ile Arg Val Leu Ser Leu
545                 550                 555                 560

Phe Asp Gly Ile Ala Thr Gly Tyr Leu Val Leu Lys Glu Leu Gly Ile
                    565                 570                 575

Lys Val Gly Lys Tyr Val Ala Ser Glu Val Cys Glu Glu Ser Ile Ala
                580                 585                 590

Val Gly Thr Val Lys His Glu Gly Asn Ile Lys Tyr Val Asn Asp Val
                595                 600                 605

Arg Asn Ile Thr Lys Lys Asn Ile Glu Glu Trp Gly Pro Phe Asp Leu
            610                 615                 620

Val Ile Gly Gly Ser Pro Cys Asn Asp Leu Ser Asn Val Asn Pro Ala
625                 630                 635                 640

Arg Lys Gly Leu Tyr Glu Gly Thr Gly Arg Leu Phe Phe Glu Phe Tyr
                    645                 650                 655

His Leu Leu Asn Tyr Ser Arg Pro Lys Glu Gly Asp Asp Arg Pro Phe
                660                 665                 670

Phe Trp Met Phe Glu Asn Val Val Ala Met Lys Val Gly Asp Lys Arg
            675                 680                 685

Asp Ile Ser Arg Phe Leu Glu Cys Asn Pro Val Met Ile Asp Ala Ile
            690                 695                 700

Lys Val Ser Ala Ala His Arg Ala Arg Tyr Phe Trp Gly Asn Leu Pro
705                 710                 715                 720

Gly Met Asn Arg Pro Val Ile Ala Ser Lys Asp Lys Leu Glu Leu
                    725                 730                 735

Gln Asp Cys Leu Glu Tyr Asn Arg Ile Ala Lys Leu Lys Lys Val Gln
                740                 745                 750

Thr Ile Thr Thr Lys Ser Asn Ser Ile Lys Gln Gly Lys Asn Gln Leu
            755                 760                 765

Phe Pro Val Met Asn Gly Lys Glu Asp Val Leu Trp Cys Thr Glu
770                 775                 780

Leu Glu Arg Ile Phe Gly Phe Pro Val His Tyr Thr Asp Val Ser Asn
785                 790                 795                 800

Met Gly Arg Gly Ala Arg Gln Lys Leu Leu Gly Arg Ser Trp Ser Val
                    805                 810                 815

Pro Val Ile Arg His Leu Phe Ala Pro Leu Lys Asp Tyr Phe Ala Cys
                820                 825                 830

Glu

<210> SEQ ID NO 14
<211> LENGTH: 853
<212> TYPE: PRT
<213> ORGANISM: Homo sapiens

<400> SEQUENCE: 14

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
                20                  25                  30

Asp Ser Pro Pro Ile Leu Glu Ala Ile Arg Thr Pro Glu Ile Arg Gly
```

```
                35                  40                  45
Arg Arg Ser Ser Ser Arg Leu Ser Lys Arg Glu Val Ser Ser Leu Leu
 50                  55                  60

Ser Tyr Thr Gln Asp Leu Thr Gly Asp Gly Asp Gly Glu Asp Gly Asp
 65                  70                  75                  80

Gly Ser Asp Thr Pro Val Met Pro Lys Leu Phe Arg Glu Thr Arg Thr
                     85                  90                  95

Arg Ser Glu Ser Pro Ala Val Arg Thr Arg Asn Asn Asn Ser Val Ser
                100                 105                 110

Ser Arg Glu Arg His Arg Pro Ser Pro Arg Ser Thr Arg Gly Arg Gln
                115                 120                 125

Gly Arg Asn His Val Asp Glu Ser Pro Val Glu Phe Pro Ala Thr Arg
                130                 135                 140

Ser Leu Arg Arg Arg Ala Thr Ala Ser Ala Gly Thr Pro Trp Pro Ser
145                 150                 155                 160

Pro Pro Ser Ser Tyr Leu Thr Ile Asp Leu Thr Asp Asp Thr Glu Asp
                165                 170                 175

Thr His Gly Thr Pro Gln Ser Ser Thr Pro Tyr Ala Arg Leu Ala
                180                 185                 190

Gln Asp Ser Gln Gln Gly Gly Met Glu Ser Pro Gln Val Glu Ala Asp
                195                 200                 205

Ser Gly Asp Gly Asp Ser Ser Glu Tyr Gln Asp Gly Lys Glu Phe Gly
                210                 215                 220

Ile Gly Asp Leu Val Trp Gly Lys Ile Lys Gly Phe Ser Trp Trp Pro
225                 230                 235                 240

Ala Met Val Val Ser Trp Lys Ala Thr Ser Lys Arg Gln Ala Met Ser
                    245                 250                 255

Gly Met Arg Trp Val Gln Trp Phe Gly Asp Gly Lys Phe Ser Glu Val
                260                 265                 270

Ser Ala Asp Lys Leu Val Ala Leu Gly Leu Phe Ser Gln His Phe Asn
                275                 280                 285

Leu Ala Thr Phe Asn Lys Leu Val Ser Tyr Arg Lys Ala Met Tyr His
                290                 295                 300

Ala Leu Glu Lys Ala Arg Val Arg Ala Gly Lys Thr Phe Pro Ser Ser
305                 310                 315                 320

Pro Gly Asp Ser Leu Glu Asp Gln Leu Lys Pro Met Leu Glu Trp Ala
                325                 330                 335

His Gly Gly Phe Lys Pro Thr Gly Ile Glu Gly Leu Lys Pro Asn Asn
                340                 345                 350

Thr Gln Pro Val Val Asn Lys Ser Lys Val Arg Arg Ala Gly Ser Arg
                355                 360                 365

Lys Leu Glu Ser Arg Lys Tyr Glu Asn Lys Thr Arg Arg Thr Ala
                370                 375                 380

Asp Asp Ser Ala Thr Ser Asp Tyr Cys Pro Ala Pro Lys Arg Leu Lys
385                 390                 395                 400

Thr Asn Cys Tyr Asn Asn Gly Lys Asp Arg Gly Asp Glu Asp Gln Ser
                    405                 410                 415

Arg Glu Gln Met Ala Ser Asp Val Ala Asn Asn Lys Ser Ser Leu Glu
                420                 425                 430

Asp Gly Cys Leu Ser Cys Gly Arg Lys Asn Pro Val Ser Phe His Pro
                435                 440                 445

Leu Phe Glu Gly Gly Leu Cys Gln Thr Cys Arg Asp Arg Phe Leu Glu
450                 455                 460
```

Leu Phe Tyr Met Tyr Asp Asp Gly Tyr Gln Ser Tyr Cys Thr Val
465                 470                 475                 480

Cys Cys Glu Gly Arg Glu Leu Leu Cys Ser Asn Thr Ser Cys Cys
            485                 490                 495

Arg Cys Phe Cys Val Glu Cys Leu Glu Val Leu Val Gly Thr Gly Thr
        500                 505                 510

Ala Ala Glu Ala Lys Leu Gln Glu Pro Trp Ser Cys Tyr Met Cys Leu
        515                 520                 525

Pro Gln Arg Cys His Gly Val Leu Arg Arg Lys Asp Trp Asn Val
    530                 535                 540

Arg Leu Gln Ala Phe Phe Thr Ser Asp Thr Gly Leu Glu Tyr Glu Ala
545                 550                 555                 560

Pro Lys Leu Tyr Pro Ala Ile Pro Ala Ala Arg Arg Arg Pro Ile Arg
            565                 570                 575

Val Leu Ser Leu Phe Asp Gly Ile Ala Thr Gly Tyr Leu Val Leu Lys
            580                 585                 590

Glu Leu Gly Ile Lys Val Gly Lys Tyr Val Ala Ser Glu Val Cys Glu
            595                 600                 605

Glu Ser Ile Ala Val Gly Thr Val Lys His Glu Gly Asn Ile Lys Tyr
    610                 615                 620

Val Asn Asp Val Arg Asn Ile Thr Lys Lys Asn Ile Glu Glu Trp Gly
625                 630                 635                 640

Pro Phe Asp Leu Val Ile Gly Gly Ser Pro Cys Asn Asp Leu Ser Asn
            645                 650                 655

Val Asn Pro Ala Arg Lys Gly Leu Tyr Glu Gly Thr Gly Arg Leu Phe
            660                 665                 670

Phe Glu Phe Tyr His Leu Leu Asn Tyr Ser Arg Pro Lys Glu Gly Asp
            675                 680                 685

Asp Arg Pro Phe Phe Trp Met Phe Glu Asn Val Val Ala Met Lys Val
        690                 695                 700

Gly Asp Lys Arg Asp Ile Ser Arg Phe Leu Glu Cys Asn Pro Val Met
705                 710                 715                 720

Ile Asp Ala Ile Lys Val Ser Ala Ala His Arg Ala Arg Tyr Phe Trp
            725                 730                 735

Gly Asn Leu Pro Gly Met Asn Arg Pro Val Ile Ala Ser Lys Asn Asp
            740                 745                 750

Lys Leu Glu Leu Gln Asp Cys Leu Glu Tyr Asn Arg Ile Ala Lys Leu
            755                 760                 765

Lys Lys Val Gln Thr Ile Thr Thr Lys Ser Asn Ser Ile Lys Gln Gly
            770                 775                 780

Lys Asn Gln Leu Phe Pro Val Val Met Asn Gly Lys Glu Asp Val Leu
785                 790                 795                 800

Trp Cys Thr Glu Leu Glu Arg Ile Phe Gly Phe Pro Val His Tyr Thr
            805                 810                 815

Asp Val Ser Asn Met Gly Arg Gly Ala Arg Gln Lys Leu Leu Gly Arg
            820                 825                 830

Ser Trp Ser Val Pro Val Ile Arg His Leu Phe Ala Pro Leu Lys Asp
            835                 840                 845

Tyr Phe Ala Cys Glu
    850

<210> SEQ ID NO 15
<211> LENGTH: 694

```
<212> TYPE: PRT
<213> ORGANISM: Homo sapiens

<400> SEQUENCE: 15

Met Lys Gly Asp Thr Arg His Leu Asn Gly Glu Asp Ala Gly Gly
1               5                   10                  15

Arg Glu Asp Ser Ile Leu Val Asn Gly Ala Cys Ser Asp Gln Ser Ser
            20                  25                  30

Asp Ser Pro Pro Ile Leu Glu Ala Ile Arg Thr Pro Glu Ile Arg Gly
            35                  40                  45

Arg Arg Ser Ser Ser Arg Leu Ser Lys Arg Glu Val Ser Ser Leu Leu
        50                  55                  60

Ser Tyr Thr Gln Ser Leu Arg Arg Ala Thr Ala Ser Ala Gly Thr
65                  70                  75                  80

Pro Trp Pro Ser Pro Ser Ser Tyr Leu Thr Ile Asp Leu Thr Asp
                85                  90                  95

Asp Thr Glu Asp Thr His Gly Thr Pro Gln Ser Ser Thr Pro Tyr
            100                 105                 110

Ala Arg Leu Ala Gln Asp Ser Gln Gln Gly Gly Met Glu Ser Pro Gln
            115                 120                 125

Val Glu Ala Asp Ser Gly Asp Gly Asp Ser Ser Glu Tyr Gln Asp Gly
        130                 135                 140

Lys Glu Phe Gly Ile Gly Asp Leu Val Trp Gly Lys Ile Lys Gly Phe
145                 150                 155                 160

Ser Trp Trp Pro Ala Met Val Val Ser Trp Lys Ala Thr Ser Lys Arg
                165                 170                 175

Gln Ala Met Ser Gly Met Arg Trp Val Gln Trp Phe Gly Asp Gly Lys
            180                 185                 190

Phe Ser Glu Val Ser Ala Asp Lys Leu Val Ala Leu Gly Leu Phe Ser
            195                 200                 205

Gln His Phe Asn Leu Ala Thr Phe Asn Lys Leu Val Ser Tyr Arg Lys
        210                 215                 220

Ala Met Tyr His Ala Leu Glu Lys Ala Arg Val Arg Ala Gly Lys Thr
225                 230                 235                 240

Phe Pro Ser Ser Pro Gly Asp Ser Leu Glu Asp Gln Leu Lys Pro Met
                245                 250                 255

Leu Glu Trp Ala His Gly Gly Phe Lys Pro Thr Gly Ile Glu Gly Leu
            260                 265                 270

Lys Pro Asn Asn Thr Gln Pro Glu Asn Lys Thr Arg Arg Thr Ala
        275                 280                 285

Asp Asp Ser Ala Thr Ser Asp Tyr Cys Pro Ala Pro Lys Arg Leu Lys
        290                 295                 300

Thr Asn Cys Tyr Asn Asn Gly Lys Asp Arg Gly Asp Glu Asp Gln Ser
305                 310                 315                 320

Arg Glu Gln Met Ala Ser Asp Val Ala Asn Asn Lys Ser Ser Leu Glu
            325                 330                 335

Asp Gly Cys Leu Ser Cys Gly Arg Lys Asn Pro Val Ser Phe His Pro
            340                 345                 350

Leu Phe Glu Gly Gly Leu Cys Gln Thr Cys Arg Asp Arg Phe Leu Glu
            355                 360                 365

Leu Phe Tyr Met Tyr Asp Asp Gly Tyr Gln Ser Tyr Cys Thr Val
        370                 375                 380

Cys Cys Glu Gly Arg Glu Leu Leu Leu Cys Ser Asn Thr Ser Cys Cys
385                 390                 395                 400
```

```
Arg Cys Phe Cys Val Glu Cys Leu Glu Val Leu Val Gly Thr Gly Thr
                405                 410                 415

Ala Ala Glu Ala Lys Leu Gln Glu Pro Trp Ser Cys Tyr Met Cys Leu
            420                 425                 430

Pro Gln Arg Cys His Gly Val Leu Arg Arg Lys Asp Trp Asn Val
        435                 440                 445

Arg Leu Gln Ala Phe Phe Thr Ser Asp Thr Gly Leu Glu Tyr Glu Ala
    450                 455                 460

Pro Lys Leu Tyr Pro Ala Ile Pro Ala Ala Arg Arg Pro Ile Arg
465             470                 475                 480

Val Leu Ser Leu Phe Asp Gly Ile Ala Thr Gly Tyr Leu Val Leu Lys
                485                 490                 495

Glu Leu Gly Ile Lys Val Gly Lys Tyr Val Ala Ser Glu Val Cys Glu
                500                 505                 510

Glu Ser Ile Ala Val Gly Thr Val Lys His Glu Gly Asn Ile Lys Tyr
            515                 520                 525

Val Asn Asp Val Arg Asn Ile Thr Lys Lys Asn Ile Glu Glu Trp Gly
        530                 535                 540

Pro Phe Asp Leu Val Ile Gly Gly Ser Pro Cys Asn Asp Leu Ser Asn
545                 550                 555                 560

Val Asn Pro Ala Arg Lys Gly Leu Tyr Glu Gly Thr Gly Arg Leu Phe
                565                 570                 575

Phe Glu Phe Tyr His Leu Leu Asn Tyr Ser Arg Pro Lys Glu Gly Asp
            580                 585                 590

Asp Arg Pro Phe Phe Trp Met Phe Glu Asn Val Val Ala Met Lys Val
        595                 600                 605

Gly Asp Lys Arg Asp Ile Ser Arg Phe Leu Glu Cys Asn Pro Val Met
    610                 615                 620

Ile Asp Ala Ile Lys Val Ser Ala Ala His Arg Ala Arg Tyr Phe Trp
625                 630                 635                 640

Gly Asn Leu Pro Gly Met Asn Arg Ile Phe Gly Phe Pro Val His Tyr
                645                 650                 655

Thr Asp Val Ser Asn Met Gly Arg Gly Ala Arg Gln Lys Leu Leu Gly
            660                 665                 670

Arg Ser Trp Ser Val Pro Val Ile Arg His Leu Phe Ala Pro Leu Lys
        675                 680                 685

Asp Tyr Phe Ala Cys Glu
    690

<210> SEQ ID NO 16
<211> LENGTH: 728
<212> TYPE: PRT
<213> ORGANISM: Homo sapiens

<400> SEQUENCE: 16

Met Lys Gly Asp Thr Arg His Leu Asn Gly Glu Glu Asp Ala Gly Gly
1               5                   10                  15

Arg Glu Asp Ser Ile Leu Val Asn Gly Ala Cys Ser Asp Gln Ser Ser
            20                  25                  30

Asp Ser Pro Pro Ile Leu Glu Ala Ile Arg Thr Pro Glu Ile Arg Gly
        35                  40                  45

Arg Arg Ser Ser Ser Arg Leu Ser Lys Arg Glu Val Ser Ser Leu Leu
    50                  55                  60

Ser Tyr Thr Gln Asp Leu Thr Gly Asp Gly Asp Gly Glu Asp Gly Asp
```

```
            65                  70                  75                  80
Gly Ser Asp Thr Pro Val Met Pro Lys Leu Phe Arg Glu Thr Arg Thr
                85                  90                  95

Arg Ser Glu Ser Pro Ala Ser Leu Arg Arg Arg Ala Thr Ala Ser Ala
            100                 105                 110

Gly Thr Pro Trp Pro Ser Pro Ser Ser Tyr Leu Thr Ile Asp Leu
            115                 120                 125

Thr Asp Asp Thr Glu Asp Thr His Gly Thr Pro Gln Ser Ser Thr
130                 135                 140

Pro Tyr Ala Arg Leu Ala Gln Asp Ser Gln Gln Gly Met Glu Ser
145                 150                 155                 160

Pro Gln Val Glu Ala Asp Ser Gly Asp Gly Asp Ser Glu Tyr Gln
                165                 170                 175

Asp Gly Lys Glu Phe Gly Ile Gly Asp Leu Val Trp Gly Lys Ile Lys
            180                 185                 190

Gly Phe Ser Trp Trp Pro Ala Met Val Val Ser Trp Lys Ala Thr Ser
            195                 200                 205

Lys Arg Gln Ala Met Ser Gly Met Arg Trp Val Gln Trp Phe Gly Asp
210                 215                 220

Gly Lys Phe Ser Glu Val Ser Ala Asp Lys Leu Val Ala Leu Gly Leu
225                 230                 235                 240

Phe Ser Gln His Phe Asn Leu Ala Thr Phe Asn Lys Leu Val Ser Tyr
                245                 250                 255

Arg Lys Ala Met Tyr His Ala Leu Glu Lys Ala Arg Val Arg Ala Gly
                260                 265                 270

Lys Thr Phe Pro Ser Ser Pro Gly Asp Ser Leu Glu Asp Gln Leu Lys
            275                 280                 285

Pro Met Leu Glu Trp Ala His Gly Gly Phe Lys Pro Thr Gly Ile Glu
290                 295                 300

Gly Leu Lys Pro Asn Asn Thr Gln Pro Glu Asn Lys Thr Arg Arg Arg
305                 310                 315                 320

Thr Ala Asp Asp Ser Ala Thr Ser Asp Tyr Cys Pro Ala Pro Lys Arg
                325                 330                 335

Leu Lys Thr Asn Cys Tyr Asn Asn Gly Lys Asp Arg Gly Asp Glu Asp
            340                 345                 350

Gln Ser Arg Glu Gln Met Ala Ser Asp Val Ala Asn Asn Lys Ser Ser
            355                 360                 365

Leu Glu Asp Gly Cys Leu Ser Cys Gly Arg Lys Asn Pro Val Ser Phe
370                 375                 380

His Pro Leu Phe Glu Gly Gly Leu Cys Gln Thr Cys Arg Asp Arg Phe
385                 390                 395                 400

Leu Glu Leu Phe Tyr Met Tyr Asp Asp Gly Tyr Gln Ser Tyr Cys
                405                 410                 415

Thr Val Cys Cys Glu Gly Arg Glu Leu Leu Cys Ser Asn Thr Ser
                420                 425                 430

Cys Cys Arg Cys Phe Cys Val Glu Cys Leu Glu Val Leu Val Gly Thr
            435                 440                 445

Gly Thr Ala Ala Glu Ala Lys Leu Gln Glu Pro Trp Ser Cys Tyr Met
450                 455                 460

Cys Leu Pro Gln Arg Cys His Gly Val Leu Arg Arg Arg Lys Asp Trp
465                 470                 475                 480

Asn Val Arg Leu Gln Ala Phe Phe Thr Ser Asp Thr Gly Leu Glu Tyr
                485                 490                 495
```

Glu Ala Pro Lys Leu Tyr Pro Ala Ile Pro Ala Arg Arg Arg Pro
            500                 505                 510

Ile Arg Val Leu Ser Leu Phe Asp Gly Ile Ala Thr Gly Tyr Leu Val
        515                 520                 525

Leu Lys Glu Leu Gly Ile Lys Val Gly Lys Tyr Val Ala Ser Glu Val
    530                 535                 540

Cys Glu Glu Ser Ile Ala Val Gly Thr Val Lys His Glu Gly Asn Ile
545                 550                 555                 560

Lys Tyr Val Asn Asp Val Arg Asn Ile Thr Lys Lys Asn Ile Glu Glu
                565                 570                 575

Trp Gly Pro Phe Asp Leu Val Ile Gly Gly Ser Pro Cys Asn Asp Leu
            580                 585                 590

Ser Asn Val Asn Pro Ala Arg Lys Gly Leu Tyr Glu Gly Thr Gly Arg
        595                 600                 605

Leu Phe Phe Glu Phe Tyr His Leu Leu Asn Tyr Ser Arg Pro Lys Glu
    610                 615                 620

Gly Asp Asp Arg Pro Phe Phe Trp Met Phe Glu Asn Val Val Ala Met
625                 630                 635                 640

Lys Val Gly Asp Lys Arg Asp Ile Ser Arg Phe Leu Glu Cys Asn Pro
                645                 650                 655

Val Met Ile Asp Ala Ile Lys Val Ser Ala Ala His Arg Ala Arg Tyr
            660                 665                 670

Phe Trp Gly Asn Leu Pro Gly Met Asn Arg Ile Phe Gly Phe Pro Val
        675                 680                 685

His Tyr Thr Asp Val Ser Asn Met Gly Arg Gly Ala Arg Gln Lys Leu
    690                 695                 700

Leu Gly Arg Ser Trp Ser Val Pro Val Ile Arg His Leu Phe Ala Pro
705                 710                 715                 720

Leu Lys Asp Tyr Phe Ala Cys Glu
                725

<210> SEQ ID NO 17
<211> LENGTH: 604
<212> TYPE: PRT
<213> ORGANISM: Homo sapiens

<400> SEQUENCE: 17

Met Leu Ala Arg Ala Leu Leu Leu Cys Ala Val Leu Ala Leu Ser His
1               5                   10                  15

Thr Ala Asn Pro Cys Cys Ser His Pro Cys Gln Asn Arg Gly Val Cys
            20                  25                  30

Met Ser Val Gly Phe Asp Gln Tyr Lys Cys Asp Cys Thr Arg Thr Gly
        35                  40                  45

Phe Tyr Gly Glu Asn Cys Ser Thr Pro Glu Phe Leu Thr Arg Ile Lys
    50                  55                  60

Leu Phe Leu Lys Pro Thr Pro Asn Thr Val His Tyr Ile Leu Thr His
65                  70                  75                  80

Phe Lys Gly Phe Trp Asn Val Val Asn Asn Ile Pro Phe Leu Arg Asn
                85                  90                  95

Ala Ile Met Ser Tyr Val Leu Thr Ser Arg Ser His Leu Ile Asp Ser
            100                 105                 110

Pro Pro Thr Tyr Asn Ala Asp Tyr Gly Tyr Lys Ser Trp Glu Ala Phe
        115                 120                 125

Ser Asn Leu Ser Tyr Tyr Thr Arg Ala Leu Pro Pro Val Pro Asp Asp

```
            130                 135                 140
Cys Pro Thr Pro Leu Gly Val Lys Gly Lys Lys Gln Leu Pro Asp Ser
145                 150                 155                 160

Asn Glu Ile Val Glu Lys Leu Leu Arg Arg Lys Phe Ile Pro Asp
                165                 170                 175

Pro Gln Gly Ser Asn Met Met Phe Ala Phe Ala Gln His Phe Thr
                180                 185                 190

His Gln Phe Phe Lys Thr Asp His Lys Arg Gly Pro Ala Phe Thr Asn
                195                 200                 205

Gly Leu Gly His Gly Val Asp Leu Asn His Ile Tyr Gly Glu Thr Leu
                210                 215                 220

Ala Arg Gln Arg Lys Leu Arg Leu Phe Lys Asp Gly Lys Met Lys Tyr
225                 230                 235                 240

Gln Ile Ile Asp Gly Glu Met Tyr Pro Pro Thr Val Lys Asp Thr Gln
                245                 250                 255

Ala Glu Met Ile Tyr Pro Pro Gln Val Pro Glu His Leu Arg Phe Ala
                260                 265                 270

Val Gly Gln Glu Val Phe Gly Leu Val Pro Gly Leu Met Met Tyr Ala
                275                 280                 285

Thr Ile Trp Leu Arg Glu His Asn Arg Val Cys Asp Val Leu Lys Gln
290                 295                 300

Glu His Pro Glu Trp Gly Asp Glu Gln Leu Phe Gln Thr Ser Arg Leu
305                 310                 315                 320

Ile Leu Ile Gly Glu Thr Ile Lys Ile Val Ile Glu Asp Tyr Val Gln
                325                 330                 335

His Leu Ser Gly Tyr His Phe Lys Leu Lys Phe Asp Pro Glu Leu Leu
                340                 345                 350

Phe Asn Lys Gln Phe Gln Tyr Gln Asn Arg Ile Ala Ala Glu Phe Asn
                355                 360                 365

Thr Leu Tyr His Trp His Pro Leu Leu Pro Asp Thr Phe Gln Ile His
                370                 375                 380

Asp Gln Lys Tyr Asn Tyr Gln Gln Phe Ile Tyr Asn Asn Ser Ile Leu
385                 390                 395                 400

Leu Glu His Gly Ile Thr Gln Phe Val Glu Ser Phe Thr Arg Gln Ile
                405                 410                 415

Ala Gly Arg Val Ala Gly Gly Arg Asn Val Pro Pro Ala Val Gln Lys
                420                 425                 430

Val Ser Gln Ala Ser Ile Asp Gln Ser Arg Gln Met Lys Tyr Gln Ser
                435                 440                 445

Phe Asn Glu Tyr Arg Lys Arg Phe Met Leu Lys Pro Tyr Glu Ser Phe
450                 455                 460

Glu Glu Leu Thr Gly Glu Lys Glu Met Ser Ala Glu Leu Glu Ala Leu
465                 470                 475                 480

Tyr Gly Asp Ile Asp Ala Val Glu Leu Tyr Pro Ala Leu Leu Val Glu
                485                 490                 495

Lys Pro Arg Pro Asp Ala Ile Phe Gly Glu Thr Met Val Glu Val Gly
                500                 505                 510

Ala Pro Phe Ser Leu Lys Gly Leu Met Gly Asn Val Ile Cys Ser Pro
                515                 520                 525

Ala Tyr Trp Lys Pro Ser Thr Phe Gly Gly Glu Val Gly Phe Gln Ile
                530                 535                 540

Ile Asn Thr Ala Ser Ile Gln Ser Leu Ile Cys Asn Asn Val Lys Gly
545                 550                 555                 560
```

```
Cys Pro Phe Thr Ser Phe Ser Val Pro Asp Pro Glu Leu Ile Lys Thr
                565                 570                 575

Val Thr Ile Asn Ala Ser Ser Ser Arg Ser Gly Leu Asp Asp Ile Asn
            580                 585                 590

Pro Thr Val Leu Leu Lys Glu Arg Ser Thr Glu Leu
        595                 600
```

US 9,850,466 B2

SOMATIC CELLS WITH INNATE POTENTIAL FOR PLURIPOTENCY

CROSS-REFERENCE

This application claims the benefit of U.S. Provisional Patent Application No. 61/434,264, filed Jan. 19, 2011, which application is incorporated herein by reference in its entirety.

GOVERNMENT RIGHTS

This invention was made with government support under grant R01 CA097214 awarded by the National Institute of Health (NCI). The government has certain rights in this invention.

INTRODUCTION

Understanding stem cell biology is important for several aspects of biomedical research. In regenerative medicine, stem cells hold the promise of repairing or replacing defective tissues. In disease states such as cancer, stem cell properties have been implicated in critical steps of malignant transformation.

Currently, regenerative medicine is putting the majority of effort into working with embryonic stem cells or induced pluripotent stem cells. Each has its drawbacks. Embryonic stem cells raise ethical concerns and are difficult to obtain. Induced pluripotent stem cells are generated at a very low frequency by a process that introduces foreign genes into human cells. This approach is very difficult and, as is, cannot be used with FDA approval.

Finding new sources of stem cells that are relatively plentiful, can be expanded, and can be obtained without the same ethical concerns associated with embryonic stem cells is an important goal for advancing the field of regenerative medicine.

SUMMARY

Aspects of the present invention are drawn to compositions of Somatic Cells with Innate Potential for Pluripotency (SCIPPs; also referred to herein as single endogenous Pluripotent Somatic (ePS) cells), that have the potential to differentiate into functional derivatives of each of the major germ layers (i.e., ectodermal, endodermal and mesodermal). Also provided are methods and kits for identifying and isolating the somatic stem cells from a subject as well as methods for their genetic modification and use in tissue regeneration.

BRIEF DESCRIPTION OF THE DRAWINGS

FIG. 13: Table showing distribution of R1-R4 subsets expressing or not ALDEFLUOR in the mammary epithelium. Summary of the average distribution of total Lin− population in R1-R4 subsets; average distribution of R1-R4 subsets in total ALD+ population and average distribution of ALD+ population in R1-R4 subsets. Data are represented as percentages (means ±SEM) from 10 individual samples.

FIG. 14: Short Tandem Repeat (STR) analysis. Genomic DNA was extracted from parental mammary cells dissociated from reduction mammoplasty organoids and beating cardiomyogenic cultures derived from the corresponding parental $CD73^+CD90^-$ (R1) cell population. Analysis was conducted for two individual tissue samples (samples 1 and 2) with sample 2 being analyzed from two different independent differentiation experiments. DNA samples from H7 ESCs at passage 56 and K562 cells were included as internal controls for the genotyping reaction. Loci, including D5S818, D13S317, D7S820, D16S539, vWA, TH01, TPDX, CSF1P0 and the sex-chromosome marker amelogenin, were analyzed using the PowerPlex 1.2 or CellID genotyping kits (Promega). Allelic assignment of all 9 loci analyzed was identical between each parental breast cell population and its corresponding mesodermally-differentiated (cardiomyogenic) R1 derivative in all cases but differed between donors and from that of H7 and K562 at several loci.

FIG. 15: Fold regulation of genes analyzed between R1-ALD+, R1-ALD− and R4 epithelial subsets, H7 and H9, human ESCs. All gene expression changes were normalized to H9, hESCs. Analysis was performed with software provided by RT² Profiler PCR Array (Qiagen, Md., U.S.A.) support online.

FIG. 33: Table showing CD73 and CD90 distribution profiles for 10 disease-free women. Percentages of lineage negative cells expressing CD73 and CD90 in various combinations from 10 reduction mammoplasty samples. Age and ethnicity of tissue donors are provided.

FIG. 34: Relative expression of pluripotency, stress response and reprogramming genes in R1-R4 subpopulations, H7 and H9 hESCs and human MSCs. Custom qPCR-array (Qiagen) was performed on H7 hESCs (n=1), H9 hESCs (n=1), human MSCs (n=1), R1-R4 cells isolated from four tissue donors (n=4), single cell-derived R1 colonies grown on feeder layers (n=3), single cell-derived R1 clones grown under expansion conditions (n=3). Each sample was probed as technical duplicates in two different experiments. Analysis was performed with the RT² Profiler PCR Array online software (Qiagen, Md., U.S.A.). Averaged gene expression levels relative to those in H9 hESCs with p-values are provided.

FIG. 35, Panels A-B: (A) Unstained single cell isolates from human pancreas showing gate set up according to cell surface markers CD73 and CD90. Stained single cell isolates from human pancreas showing distribution of R1-R4 cell populations in Lineage negative fraction. (B) In vitro mammary lineage differentiation of R1 cells from Panel A. α-6-integrin =Myoepithelial cell marker; MUC1=luminal cell marker. Scale=100 μm.

DETAILED DESCRIPTION OF THE INVENTION

Figure 1:
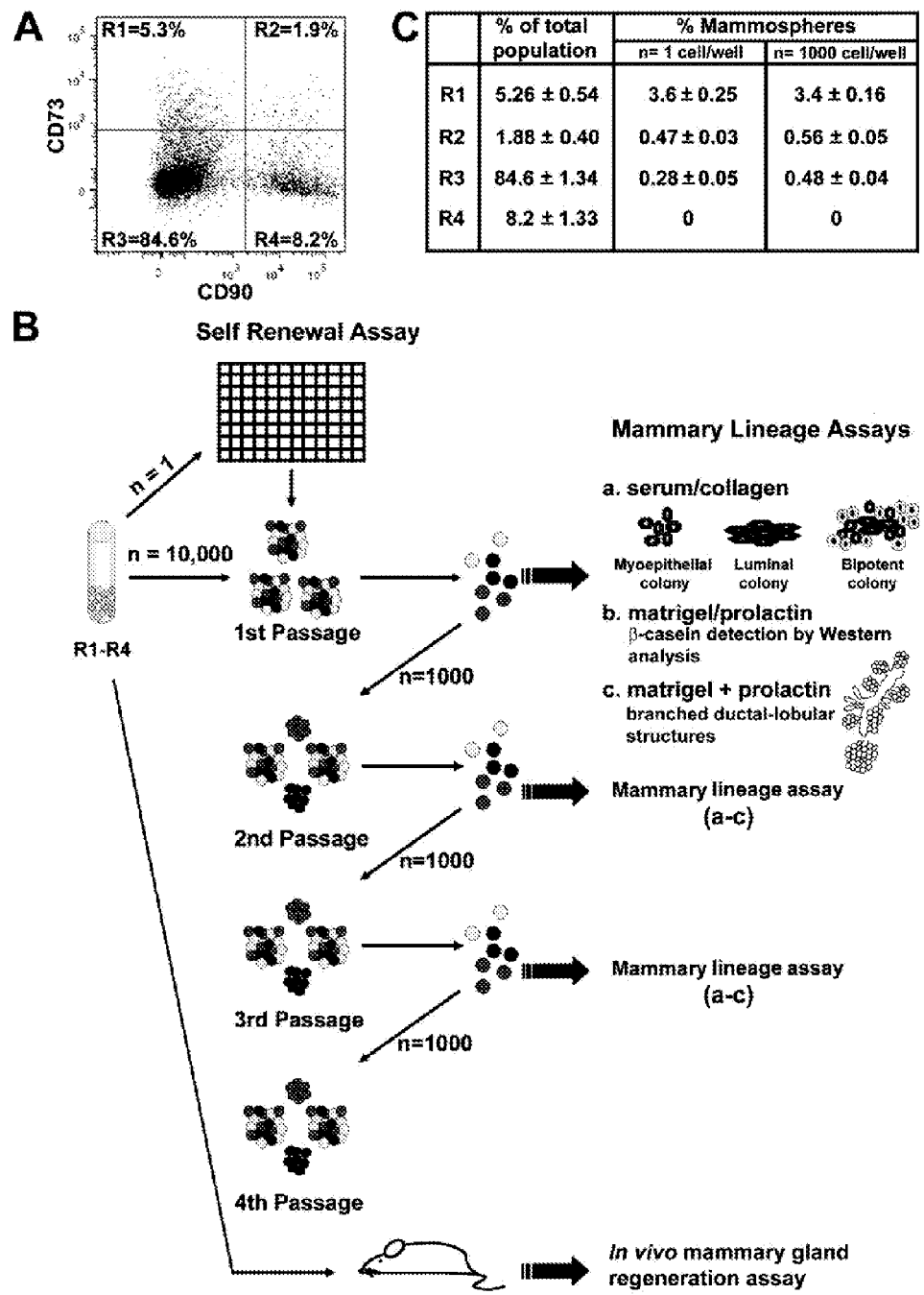
FIG. 1, Panels A-C: Isolation and assessment of cell properties. (A) Representative scatter plot of R1-R4 subpopulations from a disease-free reduction mammoplasty. Inset: average values for each subpopulation from ten samples. See FIG. 33 for individual values. (B) Experimental design for assessing self-renewal and differentiation potentials of sorted R1-R4 subpopulations. (C) R1-R4 subpopulations expressed as average percentages±SEM of the total epithelial population. Mammospheres formed from 1 cell or 1,000 cells of the R1-R4 subpopulations, expressed as averaged %±SEM (n=10).

A substantially enriched mammalian Somatic Cells with an Innate Potential for Pluripotency (SCIPP) is provided. The SCIPPs are useful in generating differentiated cells of ectodermal, endodermal and mesodermal lineages, either in vitro or in vivo. The SCIPPs are useful in transplantation, for experimental evaluation, and as a source of lineage and cell specific products.

In some embodiments, the cells are defined as being lineage marker negative (Lin⁻), CD73⁺, and CD90⁻. The determination of Lin– cells can be done in any convenient manner, including employing lineage marker-specific agents (e.g., antibodies) that bind to and thus identify cells as belonging to a specific cell lineage (e.g., blood cell lineage, e.g., macrophage, lymphocyte, etc.). In certain embodiments, the lineage panel may include binding agents for CD2, CD3, CD16, CD31, CD45, CD64 and/or CD140b. Other lineage markers can also be used in determining Lin– cells.

As detailed below, SCIPP can develop into functional differentiated cell types, including neurons and cardiomyocytes, and thus may be used to treat a variety of injury, trauma or disease states where tissue regeneration or replacement would provide a benefit (e.g., Parkinsons, Alzheimers, diabetes, osteoarthritis, wound repair, recovery after chemotherapy, aging, and the like).

Since stem cell functions are also important in several disease states (such as cancer) these cells also have the potential to be used for therapeutic screens and development of agents and biomarkers for prevention and intervention into several disease processes. SCIPP also find use as a model for studying malignant transformation as well as stochastic switching of cells, e.g., from a stable phenotypic state to a plastic state.

Systems and kits for isolating SCIPP from a subject are also provided. In addition, aspects of the invention are drawn to services for isolating and providing SCIPP for research and therapeutic purposes to an end user.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Definitions

The terms "individual," "subject," "host," and "patient," used interchangeably herein and refer to any mammalian subject that is either the source of tissue for isolating or identifying cells as described herein and/or for whom diagnosis, treatment, or therapy is desired, particularly humans.

A "gene product" is a biopolymeric product that is expressed or produced by a gene, such as a peptide or protein. A gene product may be, for example, an unspliced RNA, an mRNA, a splice variant mRNA, a polypeptide, a post-translationally modified polypeptide, a splice variant polypeptide etc. Also encompassed by this term are biopolymeric products that are made using an RNA gene product as a template (i.e., cDNA of the RNA). A gene product may be made enzymatically, recombinantly, chemically, or within a cell to which the gene is native. In many embodiments, if the gene product is proteinaceous, it exhibits a biological activity. In many embodiments, if the gene product is a nucleic acid, it can be translated into a proteinaceous gene product that exhibits a biological activity.

The terms "polypeptide" and "protein," used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like.

The term "polynucleotide" refers to polymeric forms of nucleotides of any length, either ribonucleotides or deoxyribonucleotides, including, but not limited to: single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. A polynucleotide may comprise modified nucleotides, such as methylated nucleotides and nucleotide analogs as well as one or more non-nucleotide components. The term "polynucleotide" also encompasses peptidic nucleic acids (PNAs; Pooga et al Curr Cancer Drug Targets. (2001) 1:231-9).

The term "specific binding" refers to the ability of an affinity reagent to preferentially bind to a particular target molecule that is present in a homogeneous mixture of different target molecules (e.g., a specific protein present on the surface of a cell).

Specific binding agents (also referred to as "affinity reagents") include, e.g., antibodies, antigen-binding fragments of an antibody; an epitope-binding fragment of an antibody; or other protein that bind specifically to an epitope on a target molecule, e.g., a polypeptide. Specific binding agents also include non-antibody reagents that exhibit specific binding to a target molecule.

The term "antibody", "antibody protein", "antibody reagent" and the like is used herein to refer to an affinity reagent that has at least an epitope binding domain of an antibody. These terms are well understood by those in the field, and refer to a protein containing one or more polypeptides that specifically binds an antigen. Types of antibodies include, but are not limited to: antibody isotypes, monoclonal antibodies and antigen-binding fragments thereof (e.g., Fab, Fv, scFv, and Fd fragments, chimeric antibodies, humanized antibodies, single-chain antibodies, etc.), artificial antibodies (e.g., antibodies and antibody fragments produced and selected in vitro). In some embodiments, an antibody reagent is immobilized on an insoluble, or solid, support (e.g., plate, bead, membrane, etc.). In some embodiments, a panel of antibodies is provided, where a panel of antibodies is two or more different antibodies, each specific for a different polypeptide that comprises an SCIPP signature. The antibody reagents bind specifically to a selected target polypeptide or collection of selected target polypeptides.

In some embodiments, an antibody reagent is directly or indirectly detectably labeled. Direct labels include radioisotopes; enzymes having detectable products (e.g., luciferase, β-galactosidase, etc.); fluorescent labels (e.g., fluorescein isothiocyanate, rhodamine, phycoerythrin, etc.); fluorescence emitting metals; chemiluminescent compounds, e.g., luminol, isoluminol, acridinium salts, etc; bioluminescent compounds, e.g., luciferin, fluorescent proteins (e.g., green fluorescent protein), etc. Other suitable detectable labels include fluorescent dyes, e.g., Fluorescein, Rhodamine, Texas Red, Cy2, Cy3, Cy5, Lucifer Yellow, Alexa dye family, BOD1PY, boron dipyrromethene difluoride, Oregon Green, Phycoerythrin, Phycobiliproteins, etc. Indirect labels include second antibodies specific for an antibody reagent, wherein the second antibody is labeled as described above; and members of specific binding pairs, e.g., biotin-avidin, and the like.

The term "binds specifically," in the context of a specific binding reagent, e.g., in the context of antibody binding, refers to high avidity and/or high affinity binding to a specific polypeptide i.e., epitope of a polypeptide, e.g., a cell surface expressed polypeptide (e.g., CD73, CD90, etc.). For example, antibody binding to an epitope on a specific a target protein (or fragment thereof) is stronger than binding of the same antibody to any other epitope, particularly those which may be present in the same sample. Specific binding reagents, e.g., antibodies, that bind specifically to a polypeptide may be capable of binding other polypeptides at a weak, yet detectable, level (e.g., 10% or less of the binding shown to the polypeptide of interest). Such weak binding, or background binding, is readily discernible from the specific antibody binding to a target polypeptide, e.g. by use of appropriate controls.

A composition (e.g. a polynucleotide, polypeptide, antibody, or cell composition) that is "isolated" or "in substantially isolated form" (sometimes referred to as an "enriched" or "purified" sample) refers to a composition that is in an environment different from that in which the composition naturally occurs or in which it developed. For example, a cell that is in substantially isolated form is outside of, or removed from, the site in the host in which the cell naturally developed. A composition which is in substantially isolated form is usually substantially purified or enriched.

As used herein, "subject," "host," "patient," and "individual" are used interchangeably to refer to a mammal, e.g., a human, a non-human primate, ungulates, canines, felines, equines, and the like.

The term "assessing" includes any form of measurement, and includes determining if an element is present or not. The terms "determining", "measuring", "evaluating", "assessing" and "assaying" are used interchangeably and include quantitative and qualitative determinations.

Assessing may be relative or absolute. "Assessing the presence of" includes determining the amount of something present, and/or determining whether it is present or absent. As used herein, the terms "determining," "measuring," "assessing," and "assaying" are used interchangeably and include both quantitative and qualitative determinations.

CD73 (also referred to as ecto 5'-nucleotidase) is a membrane-bound enzyme that catalyzes the conversion of AMP to bioactive adenosine at neutral pH; and also has functions independent of its enzyme activity. CD73 is expressed on various cells include endothelial cells, pericytes, follicular dendritic cells, and subsets of T cells as well as others Amino acid sequences of human CD73 are known, and are presented in, e.g., GenBank Accession Nos. AAH65937, NP_002517, and AI40168.

CD90, also known as Thy-1, is a 25-37 kD, glycosylphosphatidylinositol-anchored, cell surface glycoprotein found on many cell types. Amino acid sequences of human CD90 are known, and are presented in, e.g., GenBank Accession Nos. P04216, AAG13904, AAH65559, and NP_006279. See also, Seki et al. (1985) Proc. Natl. Acad. ScL U.S.A. 82:6657-6661.

It will be understood by those of skill in the art that the expression levels for cell surface markers (e.g., CD antigens) as described herein reflect detectable amounts of the marker protein on the cell surface. Thus, a cell that is "negative" for staining (e.g., the level of binding of a marker-specific antibody is not detectably different from an isotype matched control) may still express minor amounts of the marker. And while it is commonplace in the art to refer to cells as "positive" or "negative" for a particular marker, actual expression levels is a quantitative trait. The number of molecules on the cell surface can vary by several logs, yet still be characterized as "positive".

In some embodiments, the marker-specific staining intensity of cells can be monitored by flow cytometry, e.g., using fluorescently labeled antibodies as is known in the art. In flow cytometry, lasers are employed to detect the quantitative levels of a fluorochrome (e.g., attached to a marker-specific antibody) is associated with a single cell. The detected level of fluorochrome is proportional to the amount of cell surface marker bound by the specific reagent (e.g. labeled antibodies). Flow cytometry can be used to simultaneously detect the levels of multiple different fluorochromes, and thus can detect the level of binding of multiple differentially labeled marker-specific reagents associated (or bound to) a single cell (e.g., 2, 3, 4, 5, 6, 7, 8, 9, or 10 or more different fluorochromes/markers). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining for each desired parameter (e.g., fluorochrome, light scatted, etc.). These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but not as intense as the most brightly staining cells normally found in the population. An alternative control may utilize a substrate having a defined density of marker on its surface, for example a fabricated bead or cell line, which provides the positive control for intensity.

The gene expression level of certain genes is disclosed herein (see, e.g., FIG. 15, FIG. 34). The identity of the genes may be found by searching the Entrez PubMed database [www(dot)ncbi(dot)nlm(dot)nih(dot)gov/sites/entrez?cmd=Pager&db=pubmed] using the "Gene" search. Certain representative GeneIDs as obtained from PubMed are provided below (all are for human):
KLF4 (Kruppel-like factor 4): GeneID 9314 (SEQ ID NO: 1)
cMYC (v-myc myelocytomatosis viral oncogene homolog (avian)): GeneID 4609 (SEQ ID NO: 2)
OCT4 (POU5F1): GeneID 5460 (SEQ ID NOs: 3-5)
NANOG (Nanog homeobox): GeneID 79923 (SEQ ID NO: 6)
CD24: GeneID 100133941 (SEQ ID NO: 7)
15 EPCAM (epithelial cell adhesion molecule): GeneID 4072 (SEQ ID NO: 8)
CECR1 (cat eye syndrome chromosome region, candidate 1): GeneID 51816 (SEQ ID NOs: 9-10)
DNMT3B (DNA (cytosine-5-)-methyltransferase 3 beta): GeneID 1789 (SEQ ID NOs: 11-16)
PTGS2 (prostaglandin-endoperoxide synthase 2): GeneID 5743 (SEQ ID NO: 17).

Markers of Somatic Cells with an Innate Potential for Pluripotency (SCIPP)

Somatic Cells with an Innate Potential for Pluripotency are provided, herein termed SCIPP. SCIPPs may also be referred to herein as endogenous Pluripotent Somatic (ePS) cells. The terms "Somatic Cells with an Innate Potential for Pluripotency," "SCIPP", "endogenous Pluripotent Somatic cell," and "ePS" may be used interchangeably herein. The SCIPP population is useful in any of a variety of research and therapeutic purposes, e.g., transplantation, tissue regeneration (e.g., for the replacement or repair of damaged cells/tissues of a subject), in vitro development assays, drug screening, experimental models of cellular differentiation and interaction; screening in vitro assays to define growth and differentiation factors, and to characterize genes involved in development of particular lineages, and the like. The native cells may be used for these purposes, or they may be genetically modified to provide altered capabilities.

In some embodiments, SCIPPs can be enriched from a complex mixture of cells by using reagents that specifically recognize markers present on the cell surface. The SCIPP express detectable levels of, or are "positive for", the marker CD73, and are selected for a lack of expression of, or are "negative" for, Thy-1 (CD90). The SCIPP cells further have the phenotype of lacking expression of lineage specific markers. For staining purposes a cocktail of binding reagents, herein designated "Lin", may be used. The Lin panel will comprise binding reagents, e.g. antibodies and functional binding fragments thereof, ligands, peptidomimetics, etc., that recognize two or more lineage markers. Markers suitable for use in a Lin panel are typically expressed on mature cells, but are not present on multiple lineages, or on stem and progenitor cells. Lineage panel markers include, but are not limited to: CD2, CD3, CD16, CD31, CD45, CD64, CD140b, and any combination thereof.

SCIPPs may be further characterized based on their pattern of gene expression. FIGS. 15 and 34 show fold regulation of certain genes analyzed in an SCIPP cell populations (R1-ALD+ and R1-ALD− in FIG. 15; R1 in FIG. 34) and other non-SCIPP subsets (R3-ALD+, R3-ALD−, human MSC, and human ES cell line H7). Gene expression in human ES cell line H9 is used as the control for determining whether a gene demonstrates increased/decreased expression in each cell population in FIGS. 15 and 34. SCIPPs may have a gene expression pattern that is similar to the expression any 1 or more genes, 2 or more genes, 3 or more genes, 5 or more genes, 10 or more genes, 20 or more genes, or up to all of the genes as shown in FIG. 15 or 34. Applicants stress that the gene expression pattern of SCIPPs according to aspects of the invention, which are, for brevity, described in FIG. 15 or 34, include all gene expression combinations described in the tables and thus are disclosed just as if each and every gene expression combination was individually and explicitly disclosed.

For example, SCIPPs as described herein may express genes that are involved in maintaining pluripotency and/or employed for reprogramming differentiated cells to pluripotency (for exemplary descriptions of pluripotency and reprogramming factors, see US patent application publications: US20090068742 (Yamanaka et al.); US20090191159 (Sakurada et al.); US20080233610 (Thomson et al.); and US20080280362 (Jaenish et al.); each of which is incorporated herein by reference in their entirety). Genes in this category that are expressed in SCIPPs include: KLF4, MYC, OCT4, NANOG, CD24 and any combination thereof. SCIPPs may express certain epigenetic plasticity markers (e.g., CECR1, DNMT3B, or both), stress markers (e.g., PTGS2/COX2), cell adhesion molecules (e.g., EPCAM), or any combination thereof. As shown in FIG. 15 and FIG. 34, the expression levels of each of the genes KLF4, MYC, and PTGS2 is increased in SCIPPs (R1-ALD+ and R1-ALD−) as compared to the gene expression levels observed in either ESCs or MSCs. The expression levels of each of the genes POU5F1(OCT3/4), NANOG, CD24 and EPCAM in SCIPPs is increased as compared to MSCs and at a level similar to that detected in ESCs. The expression levels of each of the genes CECR1 and DNMT3B in SCIPPs is decreased as compared to ESCs and at a level similar to that detected in MSCs.

Thus, in certain embodiments, SCIPPs express increased levels of any one or more of the genes KLF4, MYC, and PTGS2 as compared to either ESCs or MSCs. In certain embodiments, SCIPPs express any one or more of the genes POU5F1/OCT3/4, NANOG, CD24 and EPCAM at increased levels as compared to MSCs and at levels similar to that detected in ESCs. In certain embodiments, SCIPPs express any one or both of the genes CECR1 and DNMT3B at decreased levels as compared to ESCs and at levels similar to that detected in MSCs.

In certain embodiments, a population of SCIPPs contains both ALD+ and ALD− cells.

When present in a subject, SCIPP express epithelial markers and are not readily discernable from other cells in the steady state. Under certain conditions, however, SCIPP begin to express increased levels of certain pluripotency genes, e.g., OCT4, NANOG, SOX and the like. Such conditions include tissue damage (e.g., under wound healing conditions) presence of activin A and when dsDNA breaks occur.

While SCIPP may be expanded in culture, they are not immortal, i.e., they have a limited growth potential. This feature, which is in contrast to other stem cells, e.g., ES cells, provide for an advantage when employing the cells or derivatives thereof as therapeutic agents for tissue regeneration or repair. Specifically, SCIPP have reduced potential for unregulated growth in a subject.

SCIPPs may be further characterized based on their ability to grow on certain substrates or in certain media formulations. SCIPP display unique growth characteristics in in vitro culture. For example, SCIPP can be expanded on placental fibroblast feeder cells as well as in ATALA media (see Examples section below). This unique growth property allows for SCIPP to be selectively propagated from somatic tissue, thus allowing for a robust method for producing highly enriched cultures of SCIPP, even without the use of pre-culture sorting based on the expression of CD73, CD90 and/or lineage markers.

Based on initial studies with human breast tissue, approximately 5% of ductal epithelial cells (R1 as designated below and in the Figures) typically fall within the CD73+/CD90− subset of cells. Of this 5% of CD73+/CD90− subset of ductal epithelial cells, approximately 3% represent SCIPP cells in a typical disease-free individual. This is based on an analysis of the growth and developmental characteristics of the CD73+/CD90− subset. For example, approximately 3% of the CD73+/CD90− cells will (1) form mammospheres or neurospheres in culture and (2) grow colonies that are pluripotent (e.g, on placental feeders or in ATALA culture conditions).

Methods of Isolation/Enrichment of SCIPP

Methods of isolation/enrichment of SCIPP are provided. An isolated/enriched SCIPP sample may include a single cell of the SCIPP phenotype or may comprise a population of cells, where the population of cells contain 1% or more SCIPPs of the selected phenotype, including 2% or more, 3% or more, 4% or more, 5% or more, 6% or more, 7% or more, 8% or more, 9% or more, 10% or more, 15% or more, 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 95% or more, up to and including 100% of the cells, and can be, for example, a population of cells that contain from 1% to 100%, 5% to 100%, 8% to 100%, 10% to 100%, 15% to 100%, SCIPPs of the selected phenotype.

As noted above, SCIPP can be separated from other cells in a cell sample from a subject on the basis of either specific markers, which are identified with affinity reagents, e.g. monoclonal antibodies, and/or by differential culturing techniques, e.g., by culturing a cell sample from a subject on placental fibroblast feeder cells or in ATALA media. Thus, as detailed below, an isolation method may include enriching a population of subject-derived cells for CD73+/CD90−/Lin− cells followed by culturing the cells under SCIPP growth promoting conditions. In other embodiments, a subject derived cell sample may be subjected to SCIPP growth promoting conditions without first enriching for CD73+/CD90−/Lin− cells. It is noted that any combination of enrichment/differential growth may be employed to obtain the SCIPP as detailed herein. Moreover, enrichment for only one of CD73+, CD90−, or Lin− cells may be used (as opposed to all three).

Ex vivo and in vitro cell populations useful as a source of SCIPP cells may include freshly harvested or frozen cells from any of a variety of somatic tissues, e.g., mammary tissue, pancreatic tissue, etc., where in certain embodiments the tissues are "normal" (i.e., not neoplastic, not containing tumor cells, etc.) or "disease-free." By "disease free" is meant that the tissue is asymptomatic or substantially asymptomatic for cancer, or the subject from whom the tissue was obtained is asymptomatic for cancer or in clinical remission. By "remission" or "clinical remission," which may be used synonymously, it is meant that the clinical signs, radiological signs, and symptoms of cancer have been significantly diminished or have disappeared entirely based on clinical diagnostics, although cancerous cells can still exist in the body. Thus, it is contemplated that remission encompasses partial and complete remission. The terms "normal" and "disease-free" may be used interchangeably herein. In certain embodiments, the source of SCIPP is disease-free or normal breast tissue, e.g., as obtained from reduction mammoplasty. The progenitor cells may be obtained from any mammalian species, e.g. human, equine, bovine, porcine, canine, feline, rodent, e.g. mice, rats, hamster, primate, etc. The tissue may be obtained by biopsy from a live donor, or obtained from a dead or dying donor within about 96 hours of death, or freshly frozen tissue, tissue frozen within up to 72 hours of death and maintained at below about −20° C., usually at about liquid nitrogen temperature (−180° C.) indefinitely.

The subject cells are separated from a complex mixture of cells by techniques that enrich for cells that express certain cell surface markers, while lacking certain cell specific markers. For example, methods for producing a sample enriched for SCIPP include the contacting a cell sample (e.g., a somatic cell sample) with an affinity reagent specific for CD73 and an affinity reagent specific for CD90, and then selecting for cells that are CD73 positive and CD90 negative. In some embodiments, the cell sample is also selected for cells that are lineage marker (Lin) negative (as described above; e.g., contacting the sample with affinity reagents specific for the Lin markers, and selecting for cells that are Lin negative; the cells may concurrently or subsequently be selected for cells that are $CD73^+CD90^-$). As such, selection may be made for all markers simultaneously, or for any suitable sequential process, e.g. performing a negative selection, e.g., for one or more of Lin markers and/or CD90, followed by a positive selection for CD73.

The subject cells may further be isolated based on the expression level of one or more genes as described above (and shown in FIGS. 15 and 34).

For isolation of cells from tissue, appropriate mechanical and/or enzymatic processing steps may be used and the cells placed in a suitable solution for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. Enzymes for cell isolation may include any one or more of collagenase, hyaluronidase, trypsin, dispase-DNAse I, and the like. Exemplary tissue processing steps are described in the Examples section below.

Separation of the subject cell populations may employ affinity separation to provide a substantially enriched population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the selected cells.

In certain embodiments, affinity reagents employed may be specific receptors or ligands for the cell surface molecules indicated above. In addition to antibody reagents, peptide-MHC antigen and T cell receptor pairs may be used; peptide ligands and receptor; effector and receptor molecules, phage display fragments and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of particular interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Any convenient fluorochrome may be employed, and include those mentioned above and in the Examples section below, e.g., phycobiliproteins, e.g. phycoerythrin and allophycocyanins, fluorescein and Texas red. Frequently each different marker-specific antibody is labeled with a different, differentially detexctable fluorochrome to permit independent sorting for each marker. However, where multiple different markers are to be used as negative selection markers, each different marker-specific antibody may be labeled with the same fluorochrome (e.g., all lineage marker-specific antibodies may be labeled with the same fluorochrome).

The antibodies are added to a suspension of cells, and incubated for a period of time sufficient to bind the available cell surface antigens (e.g., from 5 minutes to 1 hour; although this time can be variable and will depend on the desires of the user and the antibodies employed). It is generally desirable to have a sufficient concentration of antibodies in the reaction mixture such that the efficiency of the separation is not limited by lack of antibody. The appropriate concentration can be determined by titration. If the cells are to be cultured, grown, amplified or transplanted in subsequent steps (i.e., after the enrichment process), the medium in which the cells are separated will be any medium that maintains the viability of the cells. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc. However, if the enriched SCIPP are to be employed in assays that do not require culture and growth (e.g., to be used immediately in gene expression analyses, e.g., microarray assays), the cells may be placed in media that does not necessarily maintain viability.

In certain embodiments, the separated cells may be collected in any appropriate medium that maintains the viability and pluripotency of the cells. Various media are commercially available and may be used according to the nature of the cells, including dMEM, HBSS, dPBS, RPMI, Iscove's medium, etc., frequently supplemented with fetal calf serum.

As noted above, cells from a subject may be cultured (either with or without cell surface marker enrichment) under SCIPP selection conditions, where the SCIPP culture conditions maintains the pluripotency of the SCIPP present in the sample while expanding the cells without significant differentiation into lineage-restricted cells.

Compositions enriched for SCIPP are achieved in this manner. The SCIPP-enriched cell population can contain anywhere from 1% or more SCIPP cells, including populations of cells containing 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% or more SCIPP cells (as noted above), and in some embodiments be 95% or more of the cell composition. As note above, SCIPP are identified by their surface phenotype as well as by their ability to maintain pluripotency while expanding under specific culture conditions. In addition, SCIPP develop, under appropriate in vitro or in vivo conditions, to ectodermal, endodermal and mesodermal lineages. The enriched cell population may be used immediately, or may be frozen at liquid nitrogen temperatures and stored for long periods of time, being thawed and capable of being reused. For example, the cells may be stored in 10% DMSO, 50% FCS, 40% RPMI 1640 medium.

IN VITRO Culture and Genetic Manipulation

The enriched cell population may be grown in vitro under various culture conditions. Culture medium may be liquid or semi-solid, e.g. containing agar, methylcellulose, etc. The cell population may be conveniently suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin.

The culture may contain growth factors to which the cells are responsive. Growth factors, as defined herein, are molecules capable of promoting survival, growth and/or differentiation of cells, either in culture or in the intact tissue, e.g., through specific effects on a transmembrane receptor. Growth factors include polypeptides and non polypeptide factors. In addition to, or instead of growth factors, the subject cells may be grown in a co-culture with stromal or feeder layer cells.

The subject cultured cells may be used in a wide variety of ways. For example, the nutrient medium, which is a conditioned medium, may be isolated at various stages and the components analyzed. Separation can be achieved with HPLC, reversed phase HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions.

The SCIPP may be genetically altered or modified. For example, genes may be introduced into the SCIPP cells or genes may be deleted/inactivated for a variety of purposes, e.g., to replace genes having a loss of function mutation, to block the expression of deleterious genes, or to express genes for use as markers or reporter genes, etc. Thus, any suitable vector may be introduced into the SCIPP, including gene expression vectors; gene targeting vectors (e.g., those used in homologous recombination-based methods in ES cells, e.g., as employed in generating gene knockout cell lines and animals); vectors that express antisense mRNA, small interfering RNAs (siRNAs), ribozymes, or the like, thereby blocking expression of a gene; etc. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection, microinjection and the like. The particular manner in which the DNA is introduced is not critical to the practice of the invention.

Many vectors useful for transferring exogenous genes into target mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. Commonly used retroviral vectors are "defective", i.e. unable to produce viral proteins required for productive infection, and thus replication of the vector requires growth in a packaging cell line. Lentiviral vectors such as those based on HIV or FIV gag sequences can be used to transfect non-dividing cells.

The vectors used to genetically alter an SCIPP or cell/tissue derived therefrom may include genes that must later be removed, e.g. using a recombinase system such as Cre/Lox, or the cells that express them destroyed, e.g. by including genes that allow selective toxicity such as herpesvirus TK, bcl-xs, etc.

Vectors employed to express genes in SCIPP will include suitable promoters operably linked to the genes of interest in the vectors, where by "suitable promoter" is meant that the promoter is activated as desired by the user, e.g., in a in a desired target cell type and/or at a desired time, either in the transfected cell (the SCIPP), or progeny thereof. Promoters may be constitutively active, conditionally active, inducible or repressible as known in the art.

To prove that one has genetically modified progenitor cells, various techniques may be employed. The genome of the cells may be restricted and used with or without amplification. The polymerase chain reaction; gel electrophoresis; restriction analysis; Southern, Northern, and Western blots; sequencing; or the like, may all be employed. The cells may be grown under various conditions to ensure that the cells are capable of maturation to a desired cell lineages while expressing the introduced DNA as desired by the user.

Use of SCIPP in Treatments and Therapies

SCIPP cells, including cells or tissues derived therefrom, alone or in combination with proliferation factors, lineage-commitment factors, or genes, RNAs or proteins of interest, may be used in a number of treatment modalities for subjects having cell/tissue damage. Exemplary treatments/therapies include cell or tissue transplants, congenital malformations, elective surgeries, diseases, and genetic disorders. The SCIPP, or cells/tissues derived therefrom, employed in treatments may be autologous (from the subject) or allogeneic (from a donor).

The SCIPP cells or cells/tissues derived therefrom may be administered in any physiologically acceptable medium to a site in the subject in need of tissue/cell regeneration. The cells may be introduced by any convenient method, including injection, surgical means, or the like. The SCIPP or cells/tissues derived therefrom may be frozen at liquid nitrogen temperatures and stored for long periods of time, being capable of use on thawing. Once thawed, the cells may be used directly or expanded by use of growth factors and/or stromal cells appropriate for proliferation and/or differentiation as desired.

Treatment methods include providing SCIPPs directly for transplantation whereupon the tissue can be regenerated in vivo, recreate the missing tissue in vitro from SCIPP and then transplanting the tissue, or providing sufficient numbers of SCIPP suitable for transfection or transformation for ex vivo or in vivo gene therapy. Thus, the present invention includes a number of therapeutic methods, including: transplantation of SCIPPs of the present invention; transplantation of lineage-committed populations of cells derived from SCIPPs; transplantation of tissues and organs derived from SCIPPs; etc. Such methods can be employed for treatment or alleviation of conditions, diseases, disorders, cellular debilitations or deficiencies which would benefit from such therapy.

The SCIPP cells used in such treatment modalities may be propagated continuously in culture, using culture conditions that promote proliferation without promoting differentiation, using methods known in the art as useful for promoting proliferation without promoting differentiation of hESC and/or induced pluripotent stem cells (iPSCs). SCIPP cells may be used in such treatment modalities after such cells have been differentiated. SCIPP cells may be differentiated using methods known in the art as useful for differentiating stem cells (e.g hESCs and/or iPSCs) in a growth environment that enriches for cells with the desired lineage, and the guidance provided herein.

As described herein, SCIPP of the present invention have the capacity to differentiate into cells of any of the ectodermal, mesodermal, and endodermal lineage. Thus, the SCIPP of the present invention may be utilized in transplantation, cell replacement therapy, tissue regeneration, gene therapy, organ tissue replacement or regeneration and cell therapies wherein cells, tissues, organs of mesodermal, ectodermal and/or endodermal origin are derived in vivo, ex vivo or in vitro. Exemplary endoderm cell lineages include epithelial linings of the respiratory passages and gastrointestinal tract, the pharynx, esophagus, stomach, intestine and many associated glands, including salivary glands, liver, pancreas and lungs. Exemplary mesoderm cell lineages include smooth muscular coats, connective tissues, and vessels associated with tissues and organs and for replacement/therapy of the cardiovascular system, heart, cardiac muscle, cardiac vessels, other vessels, blood cells, bone marrow, the skeleton, striated muscles, and the reproductive and excretory organs. Exemplary ectoderm cell lineages include epidermis (epidermal layer of the skin), the sense organs, and the entire nervous system, including brain, spinal cord, and all the outlying components of the nervous system. A significant benefit of the SCIPP of the present invention is their potential for self-regeneration prior to commitment to any particular tissue lineage (ectodermal, endodermal or mesodermal) and then further proliferation once committed. These proliferative and differentiative attributes are very important and useful when limited amounts of appropriate cells and tissue are available for transplantation.

SCIPP possess qualities that make these cells useful in therapies that maintain or increase the functional capacity and/or longevity of lost, damaged, or diseased tissues. These qualities include, but are not limited to: the potential to be isolated and sorted, significant proliferation capabilities while retaining pluripotentcy, and ability to be manipulated to commit to multiple separate tissue lineages.

In certain embodiments, the SCIPP used for therapy, e.g., transplantation into a host, contains an exogenous gene (as described above). For example, by transfecting the pluripotent embryonic-like stem cells of the present invention with a vector comprising DNA or RNA which expresses a protein or gene of interest.

In certain embodiments, a therapeutic method referred to herein could include administration of SCIPPs and/or cells, tissues or organs derived therefrom in pharmaceutical compositions that comprise proliferation factors, lineage-commitment/differentiation factors, drugs or other therapeutic compounds, and the like.

In certain embodiments, the cells, tissues, or organs derived from SCIPP cells may have the same genome as the SCIPP cells from which they are derived. This means that over and above any karyotype changes, the chromosomal DNA will be at least 90% identical between the SCIPP cell and the cells or tissues derived therefrom. Cells or tissues that have been treated by recombinant methods to introduce a transgene or knock out an endogenous gene are still considered to have the same genome as the SCIPP cells from which they are derived, since all non-manipulated genetic elements are preserved. SCIPP cells and cells or tissues derived therefrom can be identified as having the same genome by standard genetic fingerprinting techniques. Possession of the same genome can also be inferred if the cells or tissues are obtained from the undifferentiated SCIPP cells through the course of normal mitotic division.

Screening Methods

The subject cells are useful for in vitro assays and screening to detect factors that promote differentiation or development of cells to particular lineages or differentiated cell lineages or types, e.g., neuronal cells, cardiomycoytes, mammary gland cells, etc. A wide variety of assays may be used for this purpose, including immunoassays for protein binding; determination of cell growth, differentiation and functional activity (both in vivo and in vitro); assessment of cellular morphology; and the like.

In exemplary embodiments, screening methods include combining a candidate differentiation factor with a population of Somatic Cells with an Innate Potential for Pluripotency (SCIPP) (e.g., a population containing at least 50% CD73+/CD90−/Lin−; as detailed above) and monitoring the effect of the candidate differentiation factor on the formation of differentiated cells from the SCIPP. The monitoring step can include any convenient assay or combination of assays, many of which are known in the art, including gene expression assays (either protein or nucleic acid expression), in vitro and in vivo developmental assays, functional cellular assays, etc. Monitoring may also include performing comparisons with control cell populations upon which the candidate factor(s) employed have known activities (either positive or negative controls, as are commonly used in the art). Thus, no limitation with regard to the screening assays is intended.

For nucleic acid based gene expression assays, any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A+ mRNA. One of skill in the art can readily use these methods to determine differences in the size or amount of mRNA transcripts between two samples. For example, the level of particular mRNAs in SCIPP is compared with the expression of the mRNAs in a reference sample, e.g. and MSC, an ES, a differentiated cell type, and/or a neoplastic or cancer cell (e.g., a breast tumor cell).

In certain embodiments, gene expression can be assayed for by detecting the level of a protein or polypeptide in the cell or secreted therefrom. For example, detection can utilize staining of cells with labeled antibodies, performed in accordance with conventional methods. Cells can be permeabilized to stain cytoplasmic proteins. In general, antibodies that specifically bind a differentially expressed polypeptide of the invention are added to a sample, and incubated for a period of time sufficient to allow binding to the epitope. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.) The absence or presence of antibody binding can be determined by various methods, including flow cytometry of dissociated cells, microscopy, radiography, scintillation counting, etc. Any suitable alternative methods for qualitative or quantitative detection of levels or amounts of differentially expressed polypeptide can be used, for example ELISA, western blot, immunoprecipitation, radioimmunoassay, etc.

Functional assays for monitoring the effect of a candidate differentiation factor may also include employing animal models (e.g., rodents, felines, canines, primates, etc.). Such animal models, including those in which the animal host is immuno-compromised or impaired (e.g., NOD/SCID mice) have proven valuable systems for determining developmental potential of cells, including for determining the effect of a potential differentiating factor on cells (either applied in vitro or in vivo). Exemplary assays that find us in screening assays are also described in the Examples section below.

Kits, Systems and Services

Also provided by the subject invention are kits and systems for practicing the subject methods, as described above. For example, kits containing reagents and components configured to isolate SCIPP from a subject (or a tissue/cell sample obtained from a subject), e.g., a human subject, are provided. The various components of the kits may be present in separate containers or certain compatible components may be precombined into a single container, as desired. The reagents may include one or more, solvents, tissue/sample harvesting and preparation reagents, buffers, enzymatic reagents, specific binding agents, standards or control reagents, e.g., isotype control antibodies, culture media, etc. As such, the kits may include one or more containers such as vials or bottles, with each container containing a separate component for carrying out a sample processing or preparing step and/or for carrying out one or more steps for isolating SCIPP from a subject.

In addition to above-mentioned components, the subject kits typically further include instructions for using the components of the kit to practice the subject methods, e.g., to isolate SCIPP from a subject (or a tissue/cell sample obtained from a subject). The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

As noted above, kits may be provided where the kit will include staining reagents that are sufficient to differentially identify/isolate the SCIPP cells described herein. A combination of interest may include one or more reagents specific for a marker or combination of markers of the present invention, and may further include antibodies specific for a lineage panel (as described above, e.g., CD2, CD3, CD16, CD31, CD45, CD64 and CD140b), CD73, and CD90. In certain embodiments, the staining reagents are antibodies, where in some kits the antibodies are detectably labeled (e.g., differentially labeled with fluorescent labels, as described above).

In some embodiments, a subject kit includes reagents for use in detecting a polynucleotide gene expression product, e.g., an mRNA, present in an SCIPP. For example, a kit may include PCR primer pairs, one or more nucleic acid probes, or both, where the primer pairs and probes are specific for a gene expressed in SCIPP (see, e.g., the genes listed in FIG. 15 and described above). For example, PCR primer pairs for any one or more of the genes KLF4, MYC, PTGS2, OCT4, NANOG, CD24, EPCAM, CECR1, and DNMT3B (or any combination thereof) may be included in a subject kit. The nucleic acids will in some embodiments be present in a suitable storage medium, e.g., buffered solution, typically in a suitable container. The kit includes the primers and/or probes, and may further include a buffer; reagents (e.g., for polymerase chain reaction (e.g., deoxynucleotide triphosphates (dATP, dTTP, dCTP, and dGTP), a thermostable DNA polymerase, a buffer suitable for polymerase chain reaction, a solution containing Mg2+ ions (e.g., $MgCl_2$), and other components well known to those skilled in the art for carrying out a polymerase chain reaction)). The kit may further include reagents necessary for extraction of DNA (or mRNA) from a biological sample. The kit may further include reagents necessary for reverse transcription of an mRNA, to make a cDNA copy of the mRNA. A kit will in some embodiments provide a standard for normalization of a level of a target polynucleotide to a standard, e.g., a level of a glucose-6-phosphate dehydrogenase polynucleotide (e.g, a G6PDH mRNA or cDNA copy of a G6PDH mRNA).

In certain embodiments, a kit may include isolated, viable SCIPP to a user for research or therapeutic purposes. In some of these embodiments, services for isolating SCIPP from a subject (either of the user's choosing or the service provider' choosing) are provided, where the isolated SCIPP are delivered to the user, e.g., for research or therapeutic purposes. Such services can include quality control assessment, e.g., cell purity, cell typing (e.g., HLA typing, genetic typing, etc.), pathogen assessment, and the like. The SCIPP provided may be freshly isolate or expanded in culture. Cells or tissues derived from the SCIPP, e.g., differentiated cells, lineage-specific progenitors, etc., may also be provided.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Materials and Methods

The following are general materials and protocols used in Examples below.

Dissociation of Breast Epithelium

Breast tissues were obtained from disease-free women undergoing reduction mammoplasty in accordance with an institutionally approved IRB protocol. Tissue was dissociated mechanically and enzymatically, as previously described by S. R. Romanov et al., Nature 409, 633 (2001); the disclosure of which is incorporated herein by reference. Briefly, tissue was minced and dissociated in RPMI 1640 with L-glutamine and 25 mm HEPES (Fisher, Cat #MT10041CV) supplemented with 10% fetal bovine serum (JR Scientific, Inc, Cat #43603), 100 units/ml penicillin, 100 µg/ml streptomycin SO4, 0.25 µg/ml fungizone, gentamycin (Lonza, Cat #CC4081G), 0.88 mg/ml collagenase (Worthington, Cat #CLS-2) and 0.40 mg/ml hyaluronidase (Sigma, Cat #H3506-SG) at 37° C. for 16 h. The cell suspension was centrifuged at 1400 rpm for 10 min followed by a wash with RPMI 1640/10% FBS. Clusters enriched in epithelial cells (referred to as organoids) were recovered after serial filtration through a 150-µm nylon mesh (Fisher, Cat #NC9445658), and a 40-µm nylon mesh (Fisher, Cat #NC9860187). The final filtrate contained the mammary stromal cells, consisting primarily of fibroblasts and endothelial cells. Following centrifugation at 1200 rpm for 5 min, the epithelial organoids and filtrate were frozen for long-term storage. To generate single cell suspension, epithelial organoids were further digested for 5 min in 0.5 g/L trypsin-0.2 g/L EDTA-0.58 g/L $NaHCO_3$ and 1 min in dispase-DNAse I (StemCell technologies, Cat #7913 and Cat #7900 respectively) then filtered through a 40-µm cell strainer (Fisher, Cat #087711).

Figure 22:
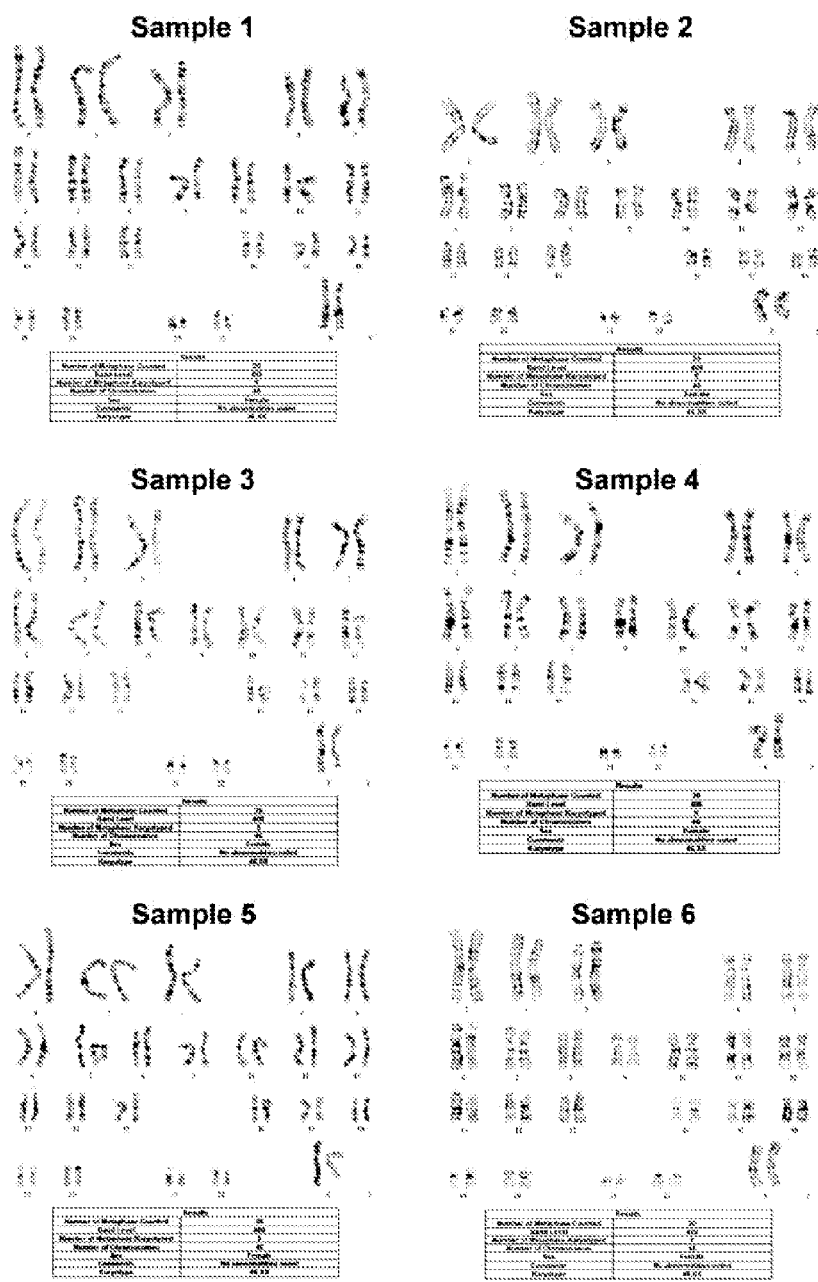
FIG. 22: Karyotypic Analysis of reduction mammoplasty samples. Representative karyotypic analyses of six individual reduction mammoplasty samples used in this study exhibit consistent diploid 46,XX (normal) status.

The following pertains to materials and protocols used in Examples 9-14 below. Mycoplasma testing was performed by PCR analysis at Bionique Testing Laboratories Inc. (Saranac Lake, N.Y.). Karyotyping of cells obtained from the filtrate fraction or from R1 cell cultures was performed on metaphase spreads at Molecular Diagnostic Services Inc. (San Diego, Calif.). All samples analyzed yielded a diploid 46,XX karyotype (see FIG. 22 and FIG. 20, Panels A-E).

Flow Cytometry Staining and ALDEFLUOR Assay for Cell Sorting

The following describes materials and protocols used in Examples 1-8 below.

The single cell suspension obtained as described above was stained for cell sorting with two human-specific primary antibodies, anti-CD73 labeled with PE (BD Biosciences, Cat #550257) and anti-CD90 labeled with APC (BD Biosciences, Cat #559869), and biotinylated antibodies for lineage markers, anti-CD2, CD3, CD16, CD64 (BD Biosciences, Cat #s 555325, 555338, 555405 and 555526), CD31 (Invitrogen, Cat #MHCD3115), CD45, CD140b (BioLegend, Cat #s 304003 and 323604) to specifically remove hematopoietic, endothelial and leukocyte lineage cells (Lin+ cells). Sequential incubation with primary antibodies was performed for 20 min at room temperature in PBS with 1% bovine serum albumin (BSA), followed by washing in PBS with 1% BSA. Biotinylated primary antibodies were revealed with an antihuman secondary antibody labeled with streptavidin-Pacific Blue conjugate (Invitrogen, Cat #S11222).

After incubation, cells were washed once in PBS with 1% BSA and processed using the ALDEFLUOR kit (StemCell Technologies, Cat #1700) in order to isolate the subpopulation with a high ALDH enzymatic activity. Cells obtained above were suspended in ALDEFLUOR assay buffer containing ALDH substrate (BAAA, 1 µmol/l per 1×106 cells) and incubated for 30 min at 37° C. An aliquot treated with 50 mmol/l diethylaminobenzaldehyde (DEAB), a specific ALDH inhibitor, was used as negative control. Cell sorting was performed using a FACSAria II cell sorter (BD Biosciences).

Flow Cytometry Staining and Cell Sorting

The following describes materials and protocols used in Examples 9-14 below.

The single cell suspension obtained as described above was stained for cell sorting with two human-specific primary antibodies, anti-CD73 labeled with PE (BD Biosciences) and anti-CD90 labeled with APC (BD Biosciences) and biotinylated antibodies for lineage markers, anti-CD3, CD16, CD64 (BD Biosciences), CD31 (Invitrogen), CD45, CD140b (BioLegend) to specifically remove hematopoietic, endothelial and leukocyte lineage cells. Sequential incubation with primary antibodies was performed for 20 min at room temperature in PBS with 1% bovine serum albumin (BSA), followed by washing in PBS with 1% BSA. Biotinylated primary antibodies were revealed with an antihuman secondary antibody labeled with streptavidin-Pacific Blue conjugate (Invitrogen). After incubation, cells were washed once in PBS with 1% BSA and cell sorting was performed using a FACSAria II cell sorter (BD Biosciences).

Mammosphere Culture

Mammosphere culture was performed as previously described by G. Dontu et al., *Genes Dev* 17, 1253 (2003); the disclosure of which is incorporated herein by reference. Single cells were plated in ultra-low attachment plates (Corning) at a density of 10,000 viable cells/ml in primary culture and 1000 cells/ml in subsequent passages. For mammosphere culture, cells were grown in a serum-free mammary epithelial basal medium (MEBM) (Lonza), supplemented with B27 (Invitrogen, Cat #17504044), 20 ng/ml bFGF (Lonza), 20 ng/ml bFGF (Sigma, Cat #F0291-25UG), and 4 µg/ml heparin (Sigma, Cat #H1027). Mammospheres were collected by gentle centrifugation (700 rpm) after 7-10 days and dissociated enzymatically for 5-10 min in 0.5 g/L trypsin-0.2 g/L EDTA-0.58 g/L NaHCO$_3$. Dissociated cells were passed through a 40-µm sieve, stained with 0.4% Trypan Blue solution (Sigma, Cat #T8154) to assess cell viability and analyzed microscopically to confirm complete cell dissociation.

Differentiation Culture Conditions

Single cell suspensions obtained from dissociated mammospheres as described above were plated on collagen-coated glass coverslips or cell culture plates at a density of 2000 viable cells/10 cm diameter dish. Cells were grown in Ham's F-12 medium with 5% FBS, 5 µg/ml insulin (Lonza), 1 µg/ml hydrocortisone (Lonza), 10 µg/ml cholera toxin (Sigma, Cat #C8052-2MG), 10 ng/ml bFGF (Lonza), and gentamycin (Lonza, Cat #CC4081G). After 5 days, a layer of Matrigel (BD Biosciences, Cat #356230) was added along with 1 µg/ml prolactin (Sigma, Cat #L4021-50UG) in the case of assays for alveolar differentiation. Cells were fixed and collected for immunostaining after 12 days. 3D cultures were performed as previously described by J. Debnath, et al., *Methods* 30, 256 (2003); the disclosure of which is incorporated herein by reference. Briefly, single cells resuspended in the above growth medium were seeded at colonogenic density on a 1-2 mm thick solidified layer of growth factor reduced Matrigel (BD Biosciences, Cat #356230). Acinar and branched-acinar structures forming in Matrigel were photographed and Western blot analysis performed after 14 days.

Immunostaining and Immunoblotting

In order to assess the lineage composition of the colonies, cells grown on coverslips were fixed for 20 min at room temperature in PBS+2% paraformaldehyde (PFA) then stained with primary anti-CD49f coupled to FITC (BD Biosciences, Cat #555735) and anti-MUC-1 (Millipore, Cat #05-652) used as myoepithelial and luminal epithelial markers respectively. A secondary antibody labeled with Alexa-Fluor 568 (Invitrogen, Cat #A-11031) was used to detect binding of anti-MUC-1. Nuclei were counterstained and mounted with DAPI/antifade (Invitrogen, Cat #P36935). Coverslips were examined with a fluorescent microscope (Zeiss LSM 510 NLO) with a 20× objective. Lineage composition was also assayed after cell trypsinization from coverslips and fixation for 20 min at room temperature in 2% PFA solution in PBS. Samples were stained with the anti-CD49f-FITC and MUC-1 primary antibodies described above for 20 min at room temperature in PBS with 1% BSA followed by an incubation with a secondary goat-anti-mouse-IgG1 antibody labeled with Tricolor (Invitrogen, Cat #M32006). After incubation, cells were washed once with PBS with 1% BSA. Flow cytometry analysis, using a BD LSRII flow cytometer (BD Biosciences), enabled the distribution of different mammary epithelial cell types (%) to be determined from mammosphere-derived cells in subsequent passages: R1-ALD+(passages 1-3): myoepithelial (MUC-1−/CD49f+): 11.43±0.48, 1.02±0.18 and 1.42±0.19; luminal (MUC-1+/CD49f−): 60.22±1.57, 62.57±1 and 23.62±0.91; bipotent (MUC-1+/CD49f+): 20.32±0.63, 31.81±0.76 and 65.54±1.08; R2-ALD+ (passages 1-2): myoepithelial: 15.45±0.94 and 20.34±0.94; luminal: 81.23±0.49 and 75.99±0.57; bipotent: 0.26±0.07 and 0.11±0.07; R3-ALD+ (passages 1-2): myoepithelial: 0.07±0.02 and 0.04±0.07; luminal: 94.92±0.57 and 96.6±0.69; bipotent: 4.01±0.69 and 2.32±0.18. The R1-R3 ALD− sorted cells yielded only luminal cells: R1-ALD−: 96.4±0.57, R2-ALD−: 96.8±0.94 and R3-ALD−: 97.77±0.49). Data are expressed as Mean±SEM (n=5). Differentiation towards the alveolar lineage was assessed in lysates of cells that had been layered with Matrigel and prolactin. Briefly, cells were pelleted at 1500 rpm for 3 min at 4° C. and washed once in icecold wash buffer (25 mM Tris, pH 7.5, 250 mM sucrose, 2.5 mM MgCl2, 10 mM benzamidine, 10 mM NAF, 1 mM sodium vanadate, 10 µg/ml leupeptin, 10 µg/ml aprotinin, 1 µg/ml pepstatin and 1 mM PMSF). Pellet was resuspunded in lysis buffer (20 mM HEPES-KOH, pH 7.5, 10 mM KCl, 1.5 mM MgCl2, 1 mM EDTA, 1 mM EGTA, 250 mM sucrose, 1 mM sodium vanadate, 1 mM DTT, 25 µg/ml leupeptin, 25 µg/ml aprotinin, 2.5 µg/ml pepstatin, 1 mM PMSF, 10 mM benzamidine and 20 mM NaF), Protein concentration of Dounce homogenized cell extracts was determined with bicinchoninic acid (Pierce Biotechnology, Rockford, Ill.) using BSA as a standard (Sigma). Cell extracts were heat denatured in loading buffer containing 5% β-mercaptoethanol and separated by gradient (4-20%) polyacrylamide gel electrophoresis (Cambrex).

Proteins were transferred onto Hybond-P memebranes (GE Healthcare Bio, Piscataway, N.J.). Membranes were probed with mouse monoclonal antibodies against human β-casein (Santa Cruz Biotechnology, Cat #SC-53189), or mouse anti-β-actin (Sigma, Cat #AC-15), followed by a horseradish peroxidase-conjugated goat anti-mouse antibody (Biomeda Corp., Foster City, Calif.). β-actin was used as a normalization loading control. Staining was developed with the SuperSignal West Pico chemiluminescence detection kit (Pierce).

Animal Model

NOD/SCID mice were used to assess the in vivo stem cell properties of sorted R1-R4 epithelial subpopulations from three disease-free breast tissue samples. The animal model used for xenotransplantation of normal mammary epithelial cells has been previously described by D. A. Proia, et al., *Nat Protoc* 1, 206 (2006); the disclosure of which is incorporated herein by reference. The fat pads were cleared pre-puberty and humanized by injecting 35 ul of a 1:1 mixture of irradiated (4Gy) and nonirradiated immortalized primary human mammary fibroblasts (500,000 cells total/fat pad). Fibroblasts, immortalized with human telomere and GFP (RMF/EG), were a generous gift from Dr. Charlotte Kuperwasser (Tufts University School of Medicine, Boston, Mass.). Sorted epithelial cells were mixed with 500,000 RMF/EG fibroblasts in 35 ul of a 1:3 mixture of Matrigel-Collagen I (BD Biosciences) and implanted in the fat pads 2-4 weeks after clearing and humanization. Ductal outgrowths were analyzed in euthanized animals 12 weeks after cell injection. Human-beta casein production was monitored in animals injected with sorted cells, mated and euthanized at day 18 of pregnancy. Fat pads were fixed in formalin and embedded in paraffin for histological analysis. Evaluation of the outgrowth potential of each cell population was analyzed by H&E staining. The animal studies were conducted in accordance with an institutionally approved animal protocol.

Immunohistochemistry and Immunofluorescence

Immunohistochemistry was performed on formalin-fixed paraffin-embedded tissues. Five micron thick sections were deparaffinized, rehydrated through graded alcohols, and subjected to antigen retrieval for Immunohistochemistry. Sections were incubated with mouse monoclonal antibodies against anti-human smooth muscle actin (α-SMA) diluted 1:80 (Dako, Cat #M0851) and anti-human CK8/18 (Leica Microsystems, Cat #RTU-5D3), and a rabbit polyclonal antibody against anti-human 3 casein (a generous gift from Dr. Charles Streuli, University of Manchester, Manchester, U K) Immunocomplexes were visualized by the ABC peroxidase method and sections were counterstained with hematoxylin. For fluorescent double staining, samples were incubated for 2 h at room temperature with Alexa Fluor 594 (Invitrogen, Cat #A11020) and Alexa Fluor 488 (Invitrogen, Cat #A21121) labeled secondary antibodies diluted 1/500. Nuclei were counterstained with Vectashield-DAPI and coverslipped. Sections were examined with a fluorescent microscope (Zeiss LSM 510 NLO).

Ectodermal Lineage Differentiation: Neurogenic:

The following describes materials and protocols used in Examples 1-8 below.

Sorted R1-R4 subsets and their respective ALDEFLUOR-positive and ALDEFLUOR-negative subpopulations were cultured in suspension at a density of 20,000 cells/well in a 24-well low-attachment plate (Corning) for three weeks in neural precursor medium (NPM) containing 20 ng/ml bFGF (R&D Systems, Cat #233-FB-025/CF) and 500 ng/ml noggin (R&D Systems, Cat #3344-NG-050). After 3 weeks of culture, the media were changed to NPM supplemented with 20 ng/ml bFGF and cultured for another week. Phenotypic analysis of the resulting differentiated neurallineage cells (neurospheres) was performed after seeding of neurospheres resuspended in NPM (without mitogens) on poly-D-lysine (Sigma, Cat #P7886) and laminin (Sigma, Cat #L2020)-coated coverslips for either 24 h (to immunostain for Nestin expression) or for 21 days (to allow complete differentiation). Immunofluorescence analysis was performed with primary antibodies including a rabbit anti-human nestin antibody (Millipore, Cat #AB5922), a mouse anti-human β-III-tubulin antibody coupled to Alexa Fluor 555 (BD Biosciences, Cat #560339) and a mouse anti-human GFAP antibody coupled to Alexa Fluor 488 (BD Biosciences, Cat #560297). A secondary anti-rabbit antibody coupled to Alexa Fluor 546 (Invitrogen, Cat #A10040) was used to label the primary anti-nestin antibody. In order to trigger a two-stage induction leading to differentiation into dopaminergic cells, the R1-ALDEFLUOR-positive cells were first cultured as neurospheres in neural basal medium consisting of DMEM/F12 supplemented with N2 and B27 additives, 10 ng/ml bFGF and Penicillin/Streptomycin for 8 days. Fresh bFGF was added every other day. After 8 days, the neurospheres were transferred to glass coverslips coated with poly-D-lysine (100 ug/ml, Sigma) and laminin (20 ug/ml, Sigma) and cultured in the neural basal medium in the presence of SDF-1 (100 ng/ml), PTN (100 ng/ml), IGF-II (100 ng/ml) and EFNB1 (200 ng/ml) (R&D Systems, Cat #s 350-NS/CF, 252-PL, 292-G2 and 473-EB respectively) to induce specific differentiation towards dopaminergic neurons (27). Half of the medium was replaced with fresh medium containing growth factors on day 4 and every 2-3 days afterwards up to 21 days of differentiation. Immunofluorescence analysis was performed with mouse anti-tyrosine hydroxylase (TH) (Sigma, Cat #T1299) and rabbit anti-vesicular monoamine transporter 2 (VMAT2) (Millipore, Cat #AB 1598P) primary antibodies followed by goat-anti rabbit coupled to Alexa Fluor 488 (Invitrogen, Cat #A11008) and goat-anti-mouse coupled to Alexa Fluor 555 (Invitrogen, Cat #A21127) secondary antibodies to ascertain differentiation into dopaminergic neurons.

Whole-cell current-clamp recordings were obtained using a Multiclamp 700B amplifier (Molecular Devices, Sunnyvale, Calif.). Signals were filtered at 1 kHz and sampled at 10 kHz using a digidata 1440A analog-to-digital converter (Molecular Devices). The liquid junction potential was measured with 3M KCl and adjusted. Cells grown on coverslips were placed in a bath solution containing 135 mM NaCl, 5 mM KCl, 2 mM CaCl2, 1.2 mM MgCl2, 10 mM HEPES and 10 mM Glucose at ~300 mOsm (pH 7.4), and visualized at 40× magnification using an Olympus IX71 microscope with differential interface contrast optics (Olympus, Tokyo, Japan). Patch electrodes (3-4 MΩ) contained 115 mM K-gluconate, 20 mM KCl, 10 mM Na2phosphate, 10 mM HEPES, 2 mM Mg3ATP, 0.3 mM Na2GTP at ~290 mOsm (pH 7.4). Currents were manually injected to hold the membrane potential around −70 mV to record voltage responses. Tetrodotoxin (TTX) was obtained from Tocis (Missouri, MO) and applied through a gravity-fed perfusion system. All data were recorded and analyzed with the pClamp 10 software (Molecular Devices).

In vitro Ectodermal Lineage Differentiation for Neurogenic Derivatives

The following describes materials and protocols used in Examples 9-14 below.

Figure 31:
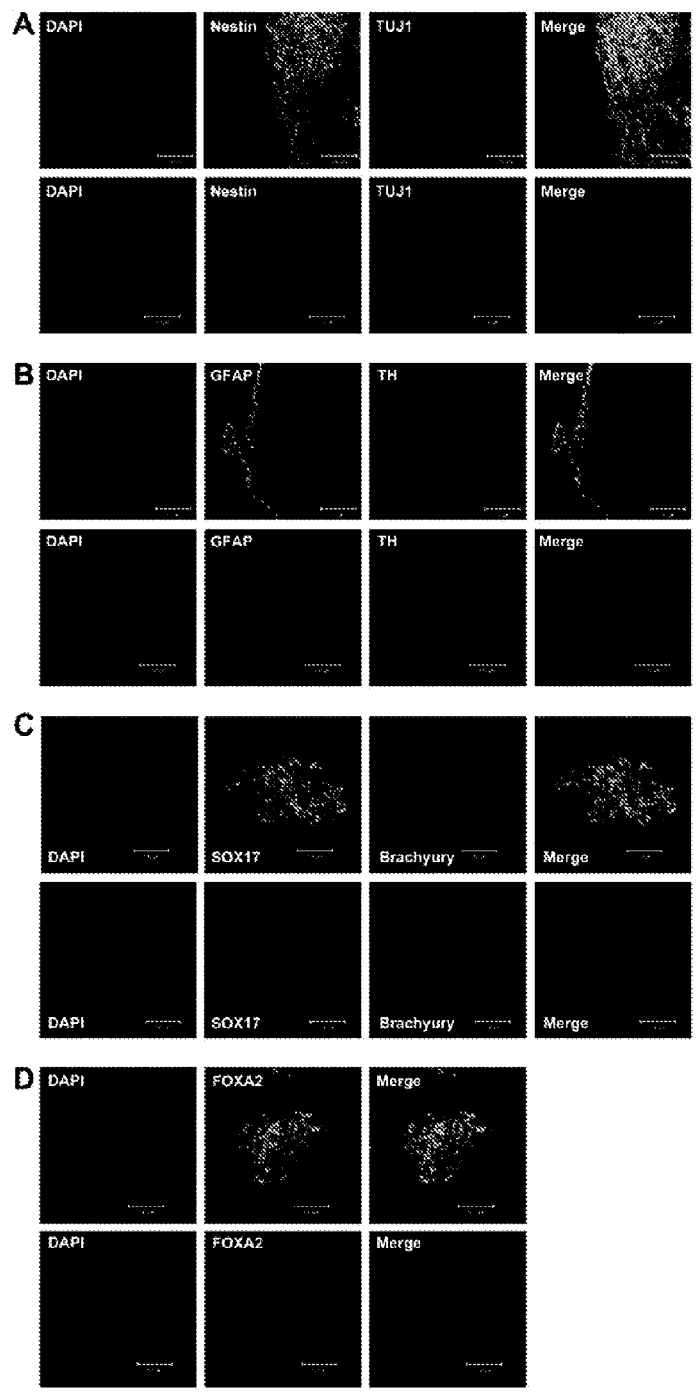
FIG. 31, Panels A-D: Specificity of antibodies used to stain ectodermal and endodermal derivatives. Antibodies selected for immunofluorescence staining of ectodermal derivatives (A-B) and endodermal derivatives (C-D) were tested on H7-derived neuronal and definitive endoderm derivatives (A-D, top rows) used as biological positive controls. Human primary fibroblasts (A-D, rows) were used as biological negative controls. Scale=100 μm.

Sorted R1-R4 subpopulations and H7 hESCs were cultured in suspension at a density of 20,000 cells/well in a 24-well low-attachment plate (Corning) for three weeks in neural precursor medium (NPM) containing 20 ng/ml bFGF (R&D Systems, Cat #233-FB-025/CF) and 500 ng/ml noggin (R&D Systems, Cat #3344-NG-050). After 3 weeks of culture, media were changed to NPM supplemented with 20 ng/ml bFGF and cultured for another week. Phenotypic analysis of the resulting differentiated neural-lineage cells (neurospheres) was performed after seeding of neurospheres resuspended in NPM (without mitogens) on poly-D-lysine (Sigma, Cat #P7886) and laminin (Sigma, Cat #L2020)-coated coverslips for either 24 h (to immunostain for Nestin expression) or for 21 days (to allow for further differentiation). Immunofluorescence analysis was performed with primary antibodies including a rabbit anti-human nestin antibody (Millipore, Cat #AB5922), a mouse anti-human TUJ1/β-III-tubulin antibody coupled to Alexa Fluor 555 (BD Biosciences, Cat #560339) and a mouse anti-human GFAP antibody coupled to Alexa Fluor 488 (BD Biosciences, Cat #560297). A secondary anti-rabbit antibody coupled to Alexa Fluor 546 (Invitrogen, Cat #A10040) was used to label the primary anti-nestin antibody. Staining controls are shown in FIG. 31, Panels A-D (top rows).

Endodermal Lineage Differentiation: Definitive Endoderm:

The following describes materials and protocols used in Examples 1-8 below.

Sorted R1-R4 subsets, and their respective ALDEFLUOR-positive and ALDEFLUOR-negative subpopulations were cultured under conditions previously reported to induce differentiation towards definitive endoderm (E. Kroon et al., *Nat Biotechnol* 26, 443 (2008); the disclosure of which is incorporated herein by reference). Briefly, sorted cells seeded on coverslips were subjected to 3 days of differentiation as follows: Day 1: culture in RPMI supplemented with glucose, Glutamax Penicillin/Streptomycin, 100 ng/ml Activin A and 25 ng/ml Wnt3a (R&D Systems, Cat #s 338-AC-025 and 5036-WN-010/CF respectively); Day 2 and Day3: culture in the same medium except Wnt3a was replaced by 0.2% FBS. Immunofluorescence analysis was performed with rabbit-anti human Sox17 (Santa Cruz Biotechnology, Cat #SC-20099), goat-anti human HNF-3β/Foxa2 (R&D Systems, Cat #AF2400) and goat-anti human Brachyury (R&D Systems, Cat #AF2085) primary antibodies followed by donkey anti-rabbit coupled to Alexa Fluor 546 (Invitrogen, Cat #A10040) and donkey anti-goat coupled to Alexa Fluor 488 (Invitrogen, Cat #A11055) secondary antibodies to ascertain differentiation towards definitive endoderm.

In vitro Endodermal Lineage Differentiation for Definitive Endoderm and Pancreatic Derivatives The following describes materials and protocols used in Examples 9-14 below.

Sorted R1-R4 subpopulations were cultured under conditions previously reported by Kroon et al. to induce pancreatic lineage in human ESCs (E. Kroon et al., *Nat Biotechnol* 26, 443 (2008)). Sorted cells seeded on coverslips or feeder layer were subjected to either 3 days (definitive endoderm) or 12 days (pancreatic lineage) of differentiation. Immunofluorescence analysis was performed with rabbit-anti human SOX17 (Santa Cruz Biotechnology, Cat #SC-20099), goat-anti human HNF-3β/FOXA2 (R&D Systems, Cat #AF2400), goat-anti human Brachyury (R&D Systems, Cat #AF2085), goat-anti human PDX1 (Santa Cruz Biotechnology, Cat #SC14662) and goat-anti human NKX6.1 (Santa Cruz Biotechnology, Cat #SC15030) primary antibodies followed by donkey anti-rabbit coupled to Alexa Fluor 546 (Invitrogen, Cat #A10040) and donkey anti-goat coupled to Alexa Fluor 488 (Invitrogen, Cat #A11055) secondary antibodies to ascertain differentiation towards endodermal lineage. Staining controls are shown in FIG. 31, Panels A-D (top rows).

Mesodermal Lineage Differentiation: Cardiomyogenic:

The following describes materials and protocols used in Examples 1-8 below.

Sorted R1-R4 subsets, and their respective ALDEFLUOR-positive and ALDEFLUOR-negative subpopulations were cultured under conditions previously described to induce cardiomyogenic differentiation by J. Bartunek et al., *Am J Physiol Heart Circ Physiol* 292, H1095 (2007); the disclosure of which is incorporated herein by reference. Sorted cells (12,000 cells/population) were expanded for 3 weeks in DMEM supplemented with 20% FBS, 100 μM L-ascorbic acid (Sigma, Cat #A5960) and 20 nM dexamethasone (Sigma, Cat #D4902). Cells were then plated onto collagen-coated four well chamber slides and cultured in cardiac differentiation medium containing 2% FBS, 50 ng/ml bFGF, 25 ng/ml BMP-2 (R&D Systems, Cat #355-BM-010) and 2 ng/ml insulin-like growth factor 1 (IGF-I) (R&D Systems, Cat #291-G1-050) for 6 days. Differentiated cells were fixed in ice-cold methanol and analyzed by immunofluorescence with primary antibodies obtained from Santa Cruz Biotechnologies Inc. including mouse monoclonal IgG2a anti-human GATA-4 (Cat #SC-25310) diluted 1/200, goat polyclonal anti-human MEF-2 (Cat #SC-13917) diluted 1/200, rabbit polyclonal anti-human Nkx2.5 (Cat #SC-14033) diluted 1/100 and goat polyclonal anti-human Troponin I (Cat #SC-8118) diluted 1/100. Staining was completed with secondary antibodies including goat-anti mouse IgG2a coupled to Alexa Fluor 488 (Invitrogen, Cat #A21131), donkey anti-goat IgG coupled to Alexa Fluor 488 (Invitrogen, Cat #A11055) and goat anti-rabbit IgG coupled to Alexa Fluor 488 (Invitrogen, Cat #A11008).

In order to differentiate the sorted R1 subset into spontaneously beating cardiomyocytes, sorted cells were first grown on human placental fibroblast feeders (a generous gift from Dr. Susan Fisher, University of California San Francisco, Calif.) in serum free mammary basal medium as described above. After 14 days, colonies appearing on the placental feeders were manually dissected and allowed to form embroid bodies (EB) in suspension in cardiac differentiation medium containing Knockout DMEM (Invitrogen), 20% FBS, non-essential amino acids, Glutamine and β-mercaptoethanol. After 4 days in suspension, EBs were plated on gelatin-coated 24 well plates and fed fresh medium every day. Monitoring of beating EBs was carried out using time-lapse video microscopy in an environmental chamber controlled by Improvision's Open lab software in real time. 5-10% of EBs began beating after 12-14 days of culture.

In vitro Mesodermal Lineage Differentiation for Cardiomyocyte, Adipocyte and Endothelial Cell Derivatives The following describes materials and protocols used in Examples 9-14 below.

Sorted R1-R4 subpopulations were cultured under conditions previously described to induce cardiomyogenic differentiation by J. Bartunek et al., *Am J Physiol Heart Circ Physiol* 292, H1095 (2007); the disclosure of which is incorporated herein by reference. Sorted cells (12,000 cells/population) were expanded for 3 weeks in DMEM supplemented with 20% FBS, 100 μM L-ascorbic acid (Sigma, Cat #A5960) and 20 nM dexamethasone (Sigma, Cat #D4902). Cells were then plated onto collagen-coated four well chamber slides and cultured in cardiac differentiation medium containing 2% FBS, 50 ng/ml bFGF, 25 ng/ml BMP-2 (R&D Systems, Cat #355-BM-010) and 2 ng/ml insulin-like growth factor 1 (IGF-I) (R&D Systems, Cat #291-G1-050) for 6 days. Differentiated cells were fixed in ice-cold methanol and analyzed by immunofluorescence with primary antibodies obtained from Santa Cruz Biotechnologies Inc. including mouse monoclonal IgG2a anti-human GATA-4 (Cat #SC-25310), goat polyclonal anti-human MEF-2 (Cat #SC-13917), rabbit polyclonal anti-human Nkx2.5 (Cat #SC-14033) and goat polyclonal anti-human Troponin I (Cat #SC-8118). Staining was completed with secondary antibodies including goat-anti mouse IgG2a coupled to Alexa Fluor 488 (Invitrogen, Cat #A21131), donkey anti-goat IgG coupled to Alexa Fluor 488 (Invitrogen, Cat #A11055) and goat anti-rabbit IgG coupled to Alexa Fluor 488 (Invitrogen, Cat #A11008).

In order to differentiate the sorted R1 subpopulation into spontaneously beating cardiomyocytes, sorted cells were first grown on human placental fibroblast feeders (a generous gift from Dr. Susan Fisher, UCSF) in serum free mammary basal medium (as described above). After 14 days, colonies appearing on the feeder layer were manually dissected and allowed to form embryoid bodies (EB) in suspension in cardiac differentiation medium containing Knockout DMEM (Invitrogen), 20% FBS, non-essential amino acids, glutamine and β-mercaptoethanol. After 4 days in suspension, EBs were plated onto gelatin-coated 24 well plates and fed fresh media every day. Monitoring of beating EB-derived cells was carried out using time-lapse video microscopy in an environmental chamber controlled with the Improvision's Open lab software in real time. 5-10% of EB-derived cells began beating after 12-14 days of culture.

Adipocyte differentiation: sorted cells were expanded for 2 weeks in α-MEM medium with glutamine supplemented with 15% ES-FBS (Omega Scientific Inc., Cat #FB-05), 18% Chang B and 2% Chang C (Irvine Scientific, Cat #s C-100 and C-106, respectively) and 1× penicillin/streptomycin. Cells were then seeded into 24-well chamber slides and placed under growth conditions (expansion medium) or differentiation conditions (Gibco StemPro Adipogenesis Differentiation Kit, Cat #A10070-01) for 9 days (for Oil Red 0 staining, quantitative Real Time PCR analysis) or 18 days (for immunofluorescence analysis of FABP4). Media was changed every 3-4 days. Cells were fixed with 2% PFA prior to staining. Immunofluorescence analysis was performed with rabbit-anti human FABP4 primary antibody (Cayman Chemical, Cat #10004944) followed by goat anti-rabbit IgG coupled to Alexa Fluor 488 (Invitrogen, Cat #A11008). Human MSCs were used as differentiation control.

Quantitative Real Time PCR was performed using standard methods. Primer probe sets for FABP4 (Hs01086177_m1), Leptin (Hs00174877_m1) and PPARγ (Hs01115511_m1) were obtained from ABI. Glucuronidase B (GusB; IDT) expression was used to normalize for variances in input cDNA.

Sorted R1-R4 subpopulations were cultured under conditions previously described by Levenberg, et al. to induce endothelial cell differentiation (S. Levenberg, J. S. Golub, M. Amit, J. Itskovitz-Eldor, R. Langer, Endothelial cells derived from human embryonic stem cells. *Proceedings of the National Academy of Sciences of the United States of America* 99, 4391 (2002); the disclosure of which is incorporated herein by reference). Briefly, cells were cultured in endothelial medium as previously described and analyzed for expression of the CD31/PECAM1 cell surface marker by flow cytometry after 2 weeks. R1 cells yielded 2% CD31/PECAM1+ cells when cultured under these conditions. The CD31/PECAM1+ cells were isolated by flow cytometry and seeded at 50,000 cells per 500 μl of culture medium in a Matrigel differentiation assay. Cord formation was evaluated by phase-contrast microscopy 24 h after cell seeding. HUVECs and primary mammary epithelial cells were used as positive and negative differentiation controls, respectively.

Human Embryonic Stem Cell (hESC) Culture

H7 and H9 hESCs, routinely maintained in culture with replacement of frozen stocks every 10 passages (a generous gift from Dr. Susan Fisher, UCSF), were expanded on mouse embryonic fibroblasts (MEFs; Millipore, cat PMEF-CFL) used as a feeder layer. MEFs were grown in DMEM, M199 (Invitrogen, Cat #11150-059) and 10% FBS. Feeders were gamma irradiated at 5,100 rads and frozen for long-term storage. Prior to use, feeders were thawed at 37° C., washed and plated on gelatin-coated 6-well tissue culture plates. H7 and H9 cells were thawed, washed and plated onto confluent feeder cells and grown for up to a week before sub-culturing. The hESC culture medium consisted of Knockout DMEM, 20% Knockout Serum Replacement (Gibco, Cat #10828-028), 10 ng/ml bFGF non-essential amino acids, Glutamine, 3-mercaptoethanol and Penicillin/Streptomycin. Cultures were monitored daily to confirm that clusters of hESCs were adhering to the feeders and forming typical hESC colonies. When colonies reached an average size of 300-400 cells, colonies were manually dissected and passaged.

Teratoma Formation Assay

Six to seven week old female SCID/BEIGE mice (Charles Rivers) were used to test teratoma forming capability of directly sorted R1 cells, culture expanded R1 subclones and H7 human ESCs under institutionally approved animal protocol AN079997/AN086757. Briefly, cells were grafted under the renal capsule according to a published protocol of T. A. Prokhorova et al., *Stem cells and development* 18, 47 (2009); the disclosure of which is incorporated herein by reference. Mice were euthanized 8 weeks (H7 cells) or 12 weeks (R1 cells) after injection. Teratomas were surgically removed, fixed in formalin, embedded in paraffin and processed for immunohistochemistry as described below.

Histochemistry and Immunohistochemistry for Teratoma Analysis

Figure 32:
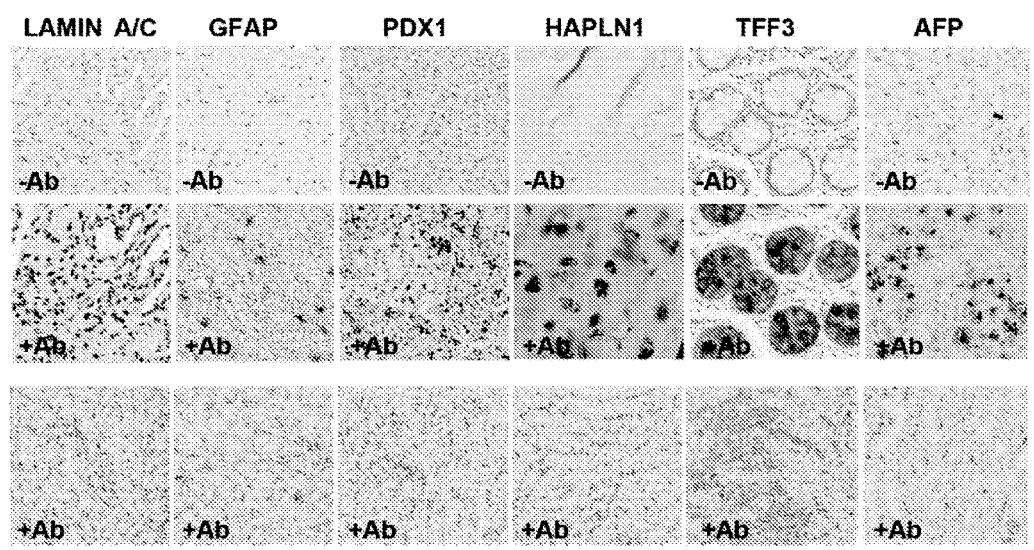
FIG. 32: Specificity of antibodies used to stain lineage derivatives within teratomas. Antibodies selected for teratoma analysis were tested on various human tissues used as antibody-specific positive controls (testis for anti-LAMIN A/C, brain for anti-GFAP, pancreas for anti-PDX1, cartilage for anti-HAPLN1, colon for anti-TFF3 and liver tumor for anti-AFP). Teratoma sections were stained in the absence (−Ab; upper row) or in the presence (+Ab; middle row) of the primary antibody as described in the Examples section. Antibodies were also tested on mouse kidney sections (lower row) to demonstrate that the antibodies failed to demonstrate a lack of cross-reactivity with murine tissues. Only the anti-TFF3 antibody showed minimal reactivity with mouse kidney but the human origin of TFF3-expressing structures in R1-derived and H7-derived teratomas was documented with the highly human-specific anti lamin A/C antibody (FIG. 27, Panel B). Magnification: 120×.

Tissues included teratomas, mammary tumors, various human tissues used as positive controls or mouse kidney used as a negative control. Paraffin-embedded tissues were cut into 4 μm serial sections, deparaffinized and rehydrated using standard procedures. All steps were carried out at room temperature except when noted. Following antigen retrieval by microwaving in citrate buffer, pH 6.0, for 10 min, sections were incubated with primary antibodies against human lamin A/C (Epitomics Inc., cat#2966-1, clone EPR4100), GFAP (Dako Inc., cat#M0761), HAPLN1 (Sigma-Aldrich Inc., cat#HPA019105), PDX1 (Epitomics Inc., cat#3470-1, clone EPR3358), AFP (Dako Inc., cat#IR500) and TFF3 (Epitomics Inc., cat#3178-1, clone EPR3973) for 1 h. Staining was visualized after incubation with HRP polymer kit (Ultravision LP kit, Thermo Scientific Inc.) for 15 minutes and with diaminobenzidine substrate (Genemed, cat#520017) for 5 minutes. For mouse kidney sections stained with the mouse monoclonal anti-GFAP antibody, an additional peroxidase blocking step (3% H202 for 10 min) was added prior to antigen retrieval and the Mouse on Mouse kit (Vector Laboratories Inc., cat#BMK2202) was used instead of the Ultravision LP kit. Stained sections were scanned at 20× on a digital slide scanner (Aperio Inc.). Image acquisition and processing were carried out using the Imagescope software (Aperio Inc.). Staining controls are shown in FIG. 32.

Single Cell-derived R1 Clone Cell Culture Conditions

Single R1 cells and H7 hESCs were expanded on human placental fibroblasts used as a feeder layer (a generous gift from Dr. Susan Fisher, UCSF). Fibroblasts from human placenta (at week 6.4 of gestation) were grown in media containing DMEM, M199 (Invitrogen, Cat #11150-059) and 10% FBS, gamma irradiated at 5,100 rads and frozen for long-term storage. Prior to use, feeders were thawed at 37° C., washed and plated on gelatin-coated 24-well tissue culture plates. Single R1 cells and H7 cells were plated on feeders 24-48 h after feeder seeding and cultured for up to 14 days for R1 cells or 7 days for H7 cells. The hESC culture medium contained Knockout DMEM, 20% Knockout Serum Replacement (Gibco, Cat #10828-028), 10 ng/ml bFGF, non-essential amino acids, glutamine, β-mercaptoethanol and penicillin/streptomycin. The R1 cell culture medium contained serum-free mammary epithelial basal medium (MEBM) (Lonza), supplemented with B27 (Invitrogen, Cat #17504044), 20 ng/ml EGF (Lonza), 20 ng/ml bFGF (Sigma, Cat #F0291-25UG), and 4 μg/ml heparin (Sigma, Cat #H1027). Cultures were monitored daily to confirm that colonies came from a single R1 cell and that clusters of hESCs were adhering to the feeders and spreading out into typical hESC colonies and to determine passaging. Single colonies and H7 cells were probed for pluripotency markers by PCR (see section below) flow cytometry analysis, immunofluorescence and Western blot analysis using anti-human OCT3/4 (Santa Cruz Biotech., Cat# SC-9081), anti-human NANOG (R&D Systems, Cat# AF1997), anti-human SOX2 (R&D Systems, Cat# MAB2018), anti-epithelial cell surface marker EPCAM (Stem Cell Technologies, Cat #10109) and anti-gamma-tubulin (Sigma, Cat# T6557) primary antibodies and respective secondary antibodies according to the manufacturer's instructions. Corresponding single colonies obtained from individual R1 cells were manually dissociated, trypsinized and split into three parts to probe for the differentiation potential of the sub-clones towards each lineage according to the procedures mentioned above.

Quantitative Real Time PCR for Pluripotency Associated Genes

Total RNA was extracted from sorted R1-R4 subpopulations, R1 colonies grown on feeder layers, R1 colonies grown in expansion media, undifferentiated H7 and H9 hESCs, or human MSCs using the PicoPure RNA Isolation Kit (Molecular Devices, Cat #KIT0204). RNA purity and concentration was determined using a 2100 Bioanalyzer (Agilent Technologies). Quantitative real time PCR was performed using 1 ng input RNA on a Custom Human $RT^2$ Profiler PCR Array (Qiagen, Md. USA) following the manufacturer's instructions. p values were generated using student's t-test with the software provided by $RT^2$ Profiler PCR Array (Qiagen) online support.

Human Mesenchymal Stem Cell Culture Conditions Human mesenchymal stem cells (Lonza; cat #PT-2501) were seeded at a recommended density of 5,000-6,000 cells per $cm^2$ and fed 3-4 days after seeding with MSCGM medium (Lonza, Cat #PT-3001) and sub-cultured according to the manufacturer's instructions.

Plasmids and Retroviral Gene Transfer

Lentiviral suspensions for short hairpin $p16^{INK4a}$ and non-targeting control were collected from transfected 293T cells as previously published by J. Zhang, C. R. Pickering, C. R. Hoist, M. L. Gauthier, T. D. Tlsty, p16INK4a modulates p53 in primary human mammary epithelial cells. *Cancer Res* 66, 10325 (2006); the disclosure of which is incorporated herein by reference. Mammary cells were transduced by exposing them to lentiviral suspensions in the presence of 4 μg/mL Polybrene (Sigma-Aldrich, Milwaukee, Wis.) for 5 hours. This step was repeated 24 h later to increase transduction efficiency. Cells were maintained in the appropriate medium for 72 hours after initial transduction, then selected in the presence of 2 μg/mL puromycin (Sigma). Cells were expanded in primary mammary epithelial medium for an additional 72 hours, trypsinized and both total RNA and cell pellet were isolated for q-PCR and flow cytometry analysis, respectively. q-PCR was performed using a primer probe set for $p16^{INK4a}$ (custom probe ID: 4331348) obtained from ABI. Glucuronidase B (GusB; IDT) expression was used to normalize for variances in input cDNA. The cell pellet was analyzed for expression of CD73 and CD90 cell surface markers by flow cytometry using antibodies as described above.

Expansion of a Single Cell-derived R1 Clone and Cell Cycle Analysis

Figure 20:
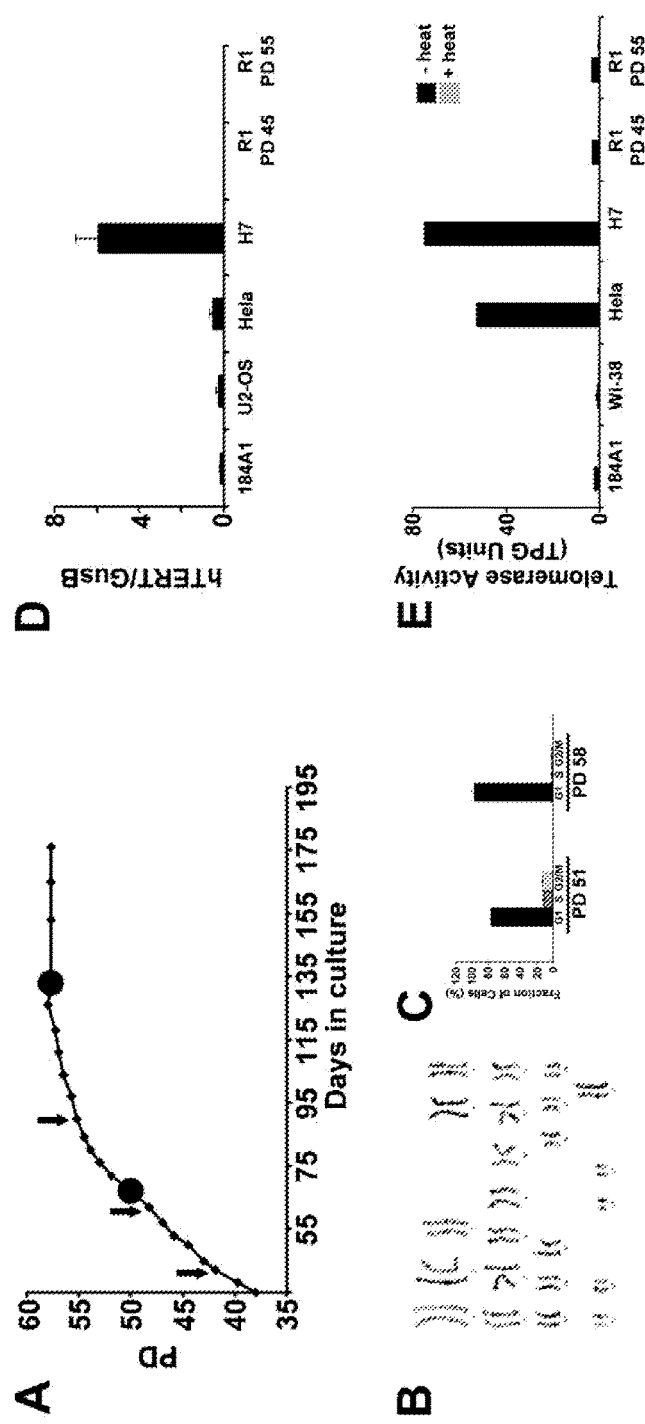
FIG. 20, Panels A-E: R1-derived clones are mortal. (A) R1 cells expanded in culture from a single cell enter senescence. Black arrows: PDs (43, 50 and 56) at which karyotypes were confirmed to be diploid 46,XX (normal); (B) Karyotypic analysis at PD 50. (C) Flow cytometry of early (PD 51) and late (PD 58) passage cells (red circles) showing DNA content after Propidium Iodide (PI) staining and demonstrating G1 arrest at late passage. (D-E) Expression of hTERT normalized to GUSB and telomerase activity evaluated using the TRAPeze XL Telomerase Detection Kit in the indicated cell lines. TPG: total products generated.

R1 sorted cells were expanded for 2 weeks in α-MEM medium with glutamine supplemented with 15% ES-FBS (Omega Scientific Inc., Cat #FB-05), 18% Chang B and 2% Chang C (Irvine Scientific, Cat #s C-100 and C-106, respectively) and 1× penicillin/streptomycin. Cells were then trypsinized and plated at limiting dilution to generate single cell-derived subclones. Single cell-derived colonies obtained after 2 weeks in culture were trypsinized using cloning rings and expanded to generate a growth curve (FIG. 20, Panel A). Population doublings were calculated using the equation: PD=log(A/B)/log 2, where A is the number of cells collected and B is the number of cells plated initially.

Cells were metabolically labeled with 10 mmol/L bromodeoxyuridine (BrdU) for 4 hours before harvest. Cells were isolated by standard trypsinization, resuspended in PBS, and fixed by addition of ice-cold 70% ethanol. Nuclei were isolated and stained with propidium iodide and FITC-conjugated anti-BrdU antibodies (BD Biosciences). Flow cytometry was carried out on a LSRII cytometer (BD Biosciences) and analyzed using the FlowJo software. All analyzed events were gated to remove debris and aggregates. A minimum of 20,000 events were collected for each analysis.

Telomerase Reverse Transcriptase Expression Measurement and Telomerase Activity Assay Human telomerase reverse transcriptase (hTERT) expression levels were assessed by q-PCR using a primer probe set for hTERT (Hs00162669_m1) obtained from ABI. Glucuronidase B (GusB; IDT) expression was used to normalize for variances in input cDNA. Telomerase activity was assayed using a highly sensitive and non-isotopic version of the Telomeric Repeat Amplification Protocol (TRAP) assay, i.e. the fluorescence-based TRAPeze XL Telomerase detection kit (Millipore). Lysates (1000 cell-equivalents) from 184A1 (human mammary cell line), Wi-38 (human fibroblast line), Hela, H7 hESCs and single cell-derived R1 subclones from PDs 44.5 and 55.2 were mixed with TRAPeze XL reaction mix containing Amplifuor primers and incubated at 30° C. for 30 minutes. Amplified fluorescently-labeled telomerase products were quantitated with a fluorescence plate reader. Telomerase activity, expressed as TPG units (total products generated), was calculated by comparing the ratio of telomerase products to an internal standard for each lysate, as described by the manufacturer.

DNA Fingerprinting

DNA fingerprinting (STR analysis) was carried out at Molecular Diagnostic Services Inc. (San Diego, Calif.). Three nanograms of genomic DNA isolated from each cell population was amplified using the PowerPlex 1.2 or CellID short tandem repeat genotyping system (Promega) according to the manufacturer's instructions. DNA amplification was performed on an Applied Biosystems 2720 thermocycler. Following amplification, reactions were denatured with Hi-Di formamide and resulting fragments were separated and detected on an ABI Prism 3130 capillary electrophoresis platform with POP7 polymer (Applied Biosystems). Analysis and allelic assignment of the respective loci was performed using the GeneScan and Genotyper (Applied Biosystems) and the PowerTyper 12 macro (Promega) software packages.

Karyotypic Analysis

Karyotyping was carried out at Molecular Diagnostic Services Inc. (San Diego, Calif.). Briefly, primary breast cells were allowed to grow to 80% confluency. Mitotic division was arrested by treating cells with 75 ng/mL Colcemid for 18.5 hours. Following treatment, cells were harvested with Trypsin-EDTA, treated with a hypotonic solution, and fixed in methanol/acetic acid. Metaphase spreads were prepared from fixed cells and stained to observe chromosomal G bands. For each tissue sample, 20 metaphase spreads were counted, 5 of which were analyzed and karyotyped. A representative karyotypic analysis is shown for several breast tissue samples.

Quantitative Real Time PCR

The following describes materials and protocols used in Examples 1-8 below.

Total RNA was extracted from sorted R1-R4 subsets and the corresponding R1 and R3 ALDEFLUOR-positive and ALDEFLUOR-negative subpopulations, undifferentiated H7 and H9 human ESCs, or human mesenchymal stem cells using the PicoPure RNA Isolation Kit (Molecular Devices, Cat #KIT0204). RNA purity and concentration was determined using the 2100 Bioanalyzer (Agilent Technologies). Quantitative real time PCR was performed using 1 ng input RNA on a Custom Human $RT^2$ Profiler PCR Array (Qiagen, Md., U.S.A.) following the manufacturer's instructions. P value was generated using student's t-test with software provided by $RT^2$ Profiler PCR Array (Qiagen, Md., U.S.A.) support online.

Example 1

Figure 7:
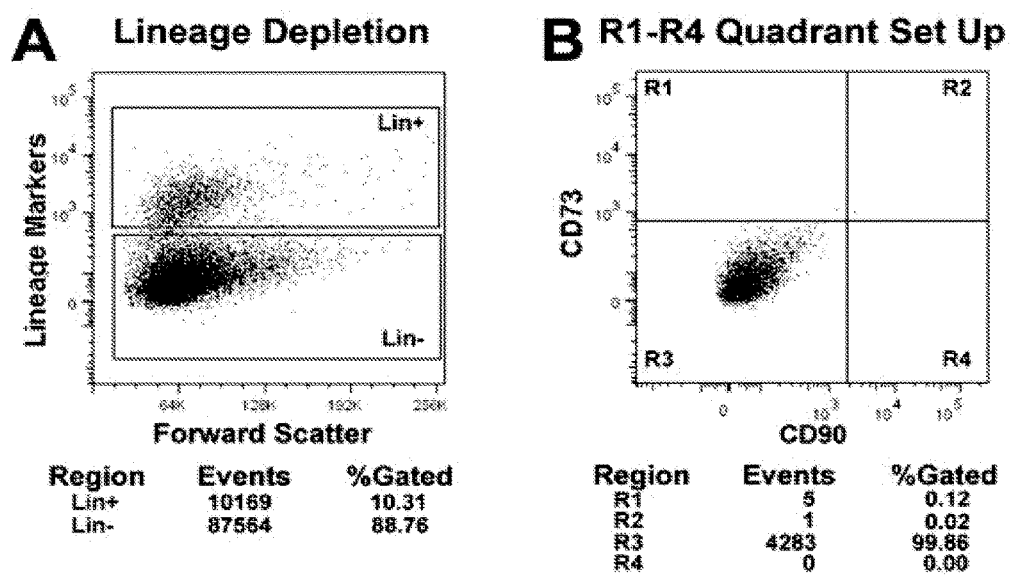
FIG. 7, Panels A-B: Isolation and fractionation of human mammary epithelial subpopulations using cell surface marker-based FACS sorting. (A) FACS analysis of lineage cell surface markers CD2, CD3, CD16, CD31, CD45, CD64 and CD140b expression in human mammary tissue on single-cell gated populations. Cells negative or positive for the above markers were defined as the Lineage-negative (Lin−) and the Lineage-positive (Lin+) population. (B) Representative FACS analysis of Lin− unstained single cells to establish the gates for CD73 and CD90 (R1-R4).

Identification and Characterization of Human Epithelial Cells that Bypass Negative Growth Signals An important phenotype of somatic stem cells is the ability to bypass negative growth signals and participate in wound healing. Based on this premise, a small subpopulation of cells within the human mammary gland was identified that continues to proliferate when the majority of cells arrest in culture. Using comparative gene expression profiling, a dramatic differential expression of genes in cells that bypassed the proliferation barrier was identified, the most prominent being an over-expression and a downregulation of the cell surface markers CD73/NT5E and CD90/THY1, respectively. Using this CD73/CD90 combination of cell surface markers, FACS was used to isolate epithelial subpopulations from freshly isolated single cell suspensions derived from reduction mammoplasties after depletion of lineage-positive (Lin+) cells, removing hematopoietic, endothelial and leukocyte lineage cells (FIG. 7, Panel A). The resultant lineage-negative (Lin−) population was fractionated (FIG. 7, Panel A) into four distinct subpopulations, CD73+CD90− (R1), CD73+CD90+ (R2), CD73−CD90− (R3) and CD73−CD90+ (R4) (FIGS. 7, Panel B and 1, Panel A), which accounted for 5.3%, 1.9%, 84.6% and 8.2% of the total Lin− population, respectively (FIG. 1, Panels A, C).

To validate the generality of these findings, these subpopulations were analyzed from ten disease-free women who underwent reduction mammoplasty. All values with standard errors from mean are provided in figure legends. The tissue donors were 24 to 49 years of age and of either Caucasian or African-American descent. All cell populations exhibited a normal (46XX) karyotype.

Figure 8:
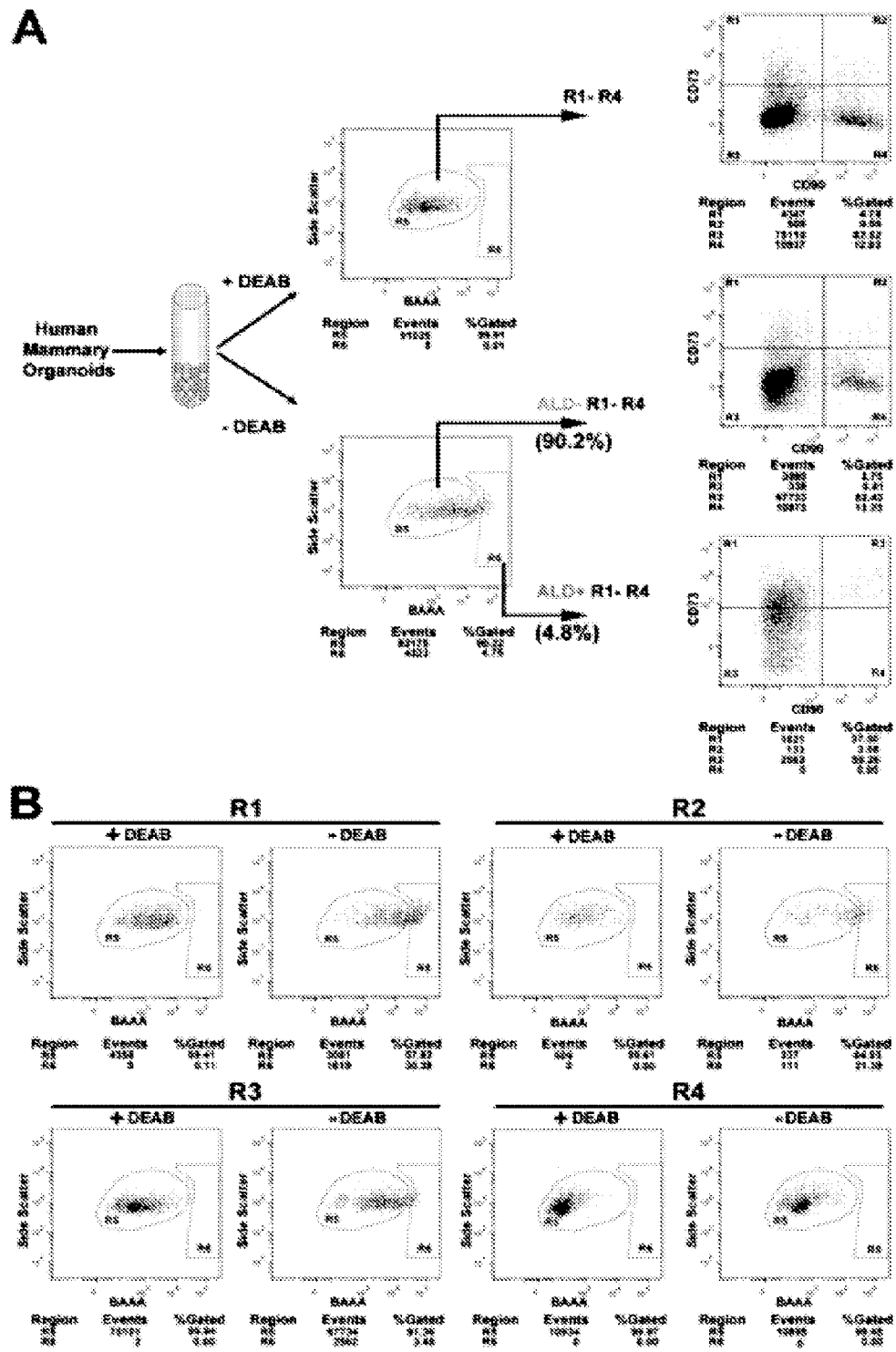
FIG. 8, Panels A-B: Experimental Design for FACS distribution of R1-R4 subsets with and without ALDEFLUOR expression. (A) Outline of FACS-based isolation of R1-R4 subsets and their corresponding ALDEFLUOR expressing counterparts. Representative FACS analysis of Lin− cells using the ALDEFLUOR assay. Cells incubated with ALDEFLUOR substrate (BAAA) and the specific ALDH inhibitor, DEAB, were used to establish the baseline fluorescence of these cells (R5) and to define the ALDEFLUOR-positive region (R6). Incubation of cells with ALDEFLUOR substrate in the absence of DEAB identifies a cell subpopulation that undergoes a shift in BAAA fluorescence and which corresponds to the ALD+ population. Distribution of R1-R4 in the absence of DEAB within the ALD− (R5) and ALD+ (R6) region. (B) Representative FACS analyses of baseline fluorescence (R5) and ALD+ region (R6) in the Lin− R1, R2, R3 and R4 populations in the presence and absence of DEAB. Data are representative of ten reduction mammoplasties.

Since aldehyde dehydrogenase (ALDH1) is a marker of normal human mammary stem cells, the ALDEFLUOR assay was used to assess the presence and size of a population with ALDH enzymatic activity in the above four epithelial subsets. ALDEFLUOR-positive (ALD+) cells were rare, accounting for only 4% of total mammary epithelial cells (FIG. 13 and FIG. 8, Panel A). No ALD+ cells were detected in R4. The large pool of ALD+ cells in R1 (40%) represents 31% of the R1 compartment. In contrast, while R3 accounts for about half of all ALD+ cells (52%), this ALD+ pool represents a very small fraction of the total R3 cell population (2.4%). Finally, the small pool of ALD+ cells in R2 (8%) accounts for 16% of the R2 compartment (FIG. 13 and FIG. 8, Panel B).

Hence, ALD+ cells are most highly enriched in the R1 and R2 sub-populations but, as will be documented below, R1 contains all of the stem cell activities.

Example 2

R1 ALDEFLUOR-Positive Cells Exhibit Sustained Mammosphere Self-Renewal Capacity

Figure 2:
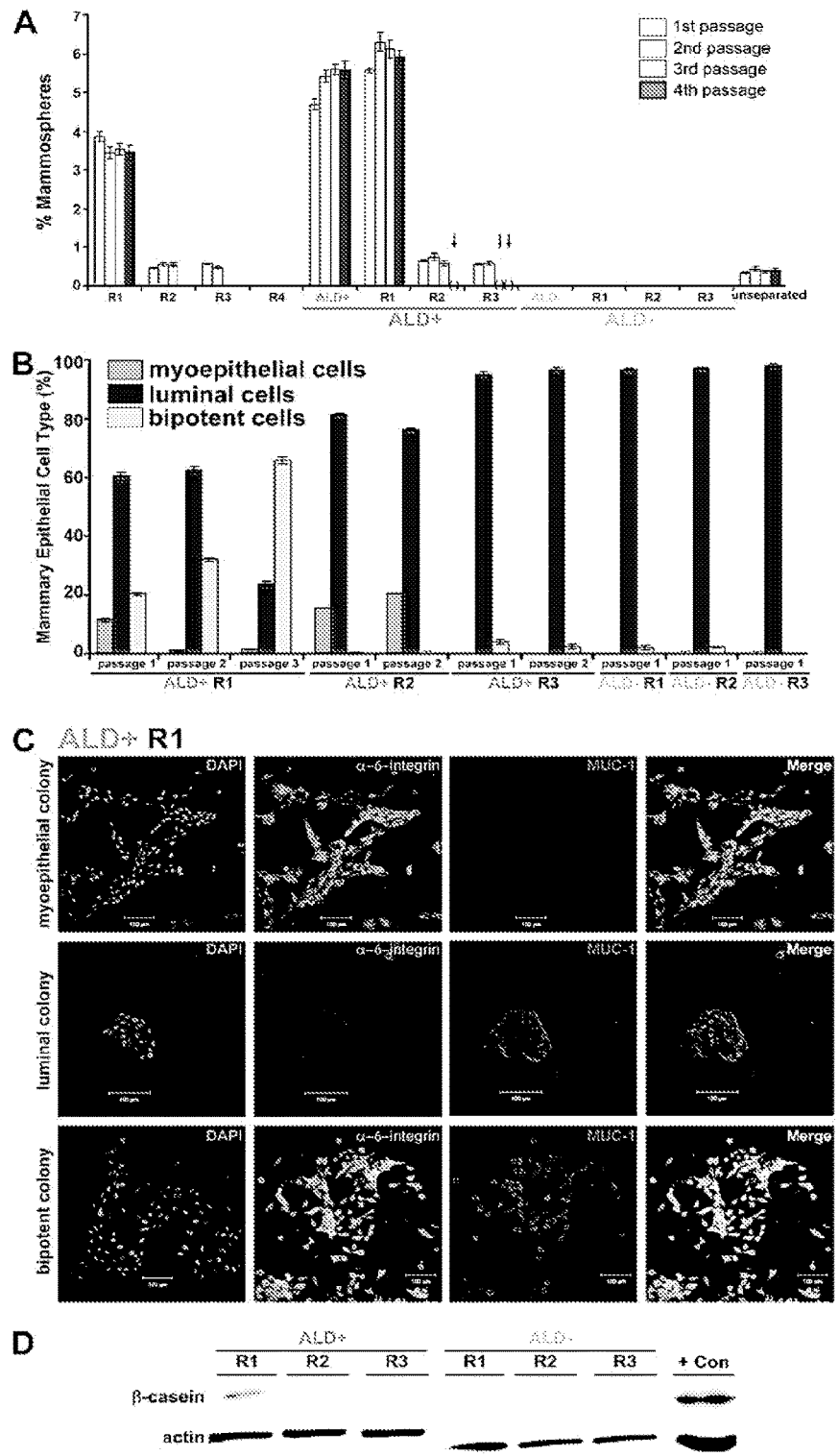
FIG. 2, Panels A-D: R1 subset enriches for ALD+ cells and has in vitro self-renewal and mammary lineage differentiation capacity for multiple passages. (A) Mammosphere forming ability (% mammospheres) for R1-R4 subsets, and for ALDEFLUOR-positive (ALD+) or ALDEFLUOR-negative (ALD−) total population and sorted R1, R2 and R3 subsets. Mammosphere initiating capacity was assessed using 10,000 plated live cells for the first passage and 1000 plated live cells in subsequent passages. Data expressed as Mean±SEM (n=5) are presented in the legend of FIG. 9, Panel A. (B) FACS analysis of cells dissociated from three passages of R1-R3 ALD+ mammospheres and grown in differentiating conditions. Cells were stained for lineage-specific markers α-6-integrin/CD49f (myoepithelial) and MUC-1 (luminal). (C) Representative images of first passage R1-ALD+ mammospheres dissociated and grown in differentiating conditions for 14 days and immuno-stained for α-6-integrin/CD49f and MUC-1. R1-ALD+ mammosphere-derived cells generate monolineage myoepithelial colonies immunostained for α-6-integrin, monolineage luminal epithelial colonies immunostained for MUC-1 and bipotent colonies with cells immunostained for both α-6-integrin and MUC-1. (D) Western blot analysis for anti-human β-casein in R1-R3 ALD+ and R1-R3 ALD− mammosphere-derived cells. Loading control: actin. Positive control: BT-20 cell line.

To test whether the R1-R4 mammary epithelial subsets with or without ALD expression had mammosphere-forming abilities, previously established in vitro assays were used. Cell self-renewal capacity was assessed by evaluating the sphere initiation efficiency of single cells cultured as mammospheres and subjected to serial passages (FIG. 1, Panel B). Consistent with the lack of ALD+ cells in the R4 population, this subset failed to generate mammospheres in suspension (FIGS. 2, Panel A; and 9, Panel A, d). In contrast, the R1-R3 populations were capable of doing so (1st passage) even when plated at 1 cell/well in 96-well plates. R1 exhibited the maximum frequency of mammosphere formation (3.9%), while R2 and R3 exhibited frequencies of 0.47% and 0.58%, respectively (FIGS. 2, Panel A; 9, Panel A, a-c). Similar results were obtained when cells were cultured at 1000 cells/ml for up to three passages.

Consistent with previous mammary cell studies, in vitro self-renewal capacity was restricted to ALD+ cells in R1-R3

(FIGS. 2, Panel A; 9, Panel A, e-g versus h-j). Robust and sustained mammosphere generation was observed for R1-ALD+(5-6% over 4 passages), this phenotype being minimal for R2-ALD+ and R3-ALD+ (FIG. 2, Panel A). Hence, the in vitro self-renewal capacity was fully defined by the CD73/CD90 expression profiles, where R1 was enriched 10-fold (4% vs. 0.4%) in colony forming ability in suspension assays compared to unsorted cells (FIG. 2, Panel A).

Example 3

R1 ALDEFLUOR-Positive Cells are Capable of In Vitro Differentiation Along all Three Mammary Lineages The ability to differentiate into multiple lineages is a functional hallmark of stem cells. To test which cells had stem or progenitor cell properties, mammosphere-derived cells from R1-R3 ALD+, were assessed using three in vitro mammary lineage assays (MLA a-c; FIG. 1, Panel B) and an in vivo mammary gland regeneration assay (FIG. 1, Panel B).

To assess in vitro lineage differentiation potential, parallel assays were conducted on serial passages of cells. Mammospheres derived from R1-R3 ALD+ were dissociated to single cells and plated on collagen-coated coverslips at colonogenic densities (MLA a; FIG. 1, Panel B) and an aliquot was placed in suspension culture to test for self-renewal capacity (FIG. 1, Panel B). Differentiation potential of each R1-R3 ALD+ (and ALD−) serial populations was assessed by flow cytometry and colony morphology analysis.

Expression of lineage-specific markers was monitored in the progeny of cells generated after colonogenic culture conditions that promote differentiation. The commitment to luminal epithelial or myoepithelial lineage was determined by immunostaining for the two mammary epithelium lineage-specific markers MUC-1 and CD49f ($\alpha$-6-integrin), respectively. As expected, R1-R3 ALD− failed to exhibit multi-lineage potential (FIG. 2, Panel B) and were highly enriched (96-97%) in luminal epithelial cells (MUC-1+/CD49f−).

The only ALD+ population to exhibit multi-lineage potential was R1. In the first passage, all three lineages were generated. With subsequent passages, the bipotent progenitors were enriched at the expense of the differentiated progeny (FIG. 2, Panel B). Indeed, the percentage of R1-ALD+ cells with bipotent (MUC-1+/CD49f+) differentiation potential increased over passages 1-3: 20%, 32% and 66%, respectively (FIG. 2, Panel B). In contrast, R2-ALD+ and R3-ALD+ contained a negligible fraction of bipotent progenitors: 0.3-0.1% and 4-2% in passages 1 and 2, respectively (FIG. 2, Panel B). In addition, whereas R2 generated both luminal and myoepithelial cells, R3 was predominantly restricted to luminal cells.

In the morphologic colonogenic assay that assesses the lineage differentiation potential of single cells, R1-ALD+ mammosphere-derived cells differentiated into three types of colonies: colonies containing exclusively myoepithelial cells (FIG. 2, Panel C, top panel), or exclusively luminal epithelial cells (FIG. 2, Panel C, middle panel) or cells of both lineages as well as bipotent cells with co-expression of both lineage markers (FIG. 2, Panel C, bottom panel). This differentiation potential was maintained in subsequent passages (data not shown). As expected from the flow cytometry results above, R2-ALD+ mammosphere-derived cells differentiated only into myoepithelial and luminal epithelial colonies, whereas R3-ALD+ mammosphere-derived cells differentiated predominantly into luminal epithelial colonies (data not shown). Of particular note, the luminal epithelial colonies generated from R3-ALD+ mammosphere derived cells were morphologically different (bigger) from those derived from R1-ALD+, even though both expressed MUC-1 (data not shown).

To test the potential to differentiate along the alveolar epithelial cell lineage (MLA b), cells derived from R1-R3 ALD+ mammospheres were allowed to differentiate on a collagen substratum for 7 days then overlaid with reconstituted basement membrane gel devoid of growth factors (Matrigel) supplemented with prolactin and further cultured for 7 days. Acquisition of alveolar differentiation was assessed by cellular production of $\beta$-casein (FIG. 2, Panel D). Under these conditions, R1-ALD+ mammosphere-derived cells were the only ones able to differentiate along the luminal, myoepithelial and alveolar lineage, representing therefore the only truly multipotent population.

Figure 9:
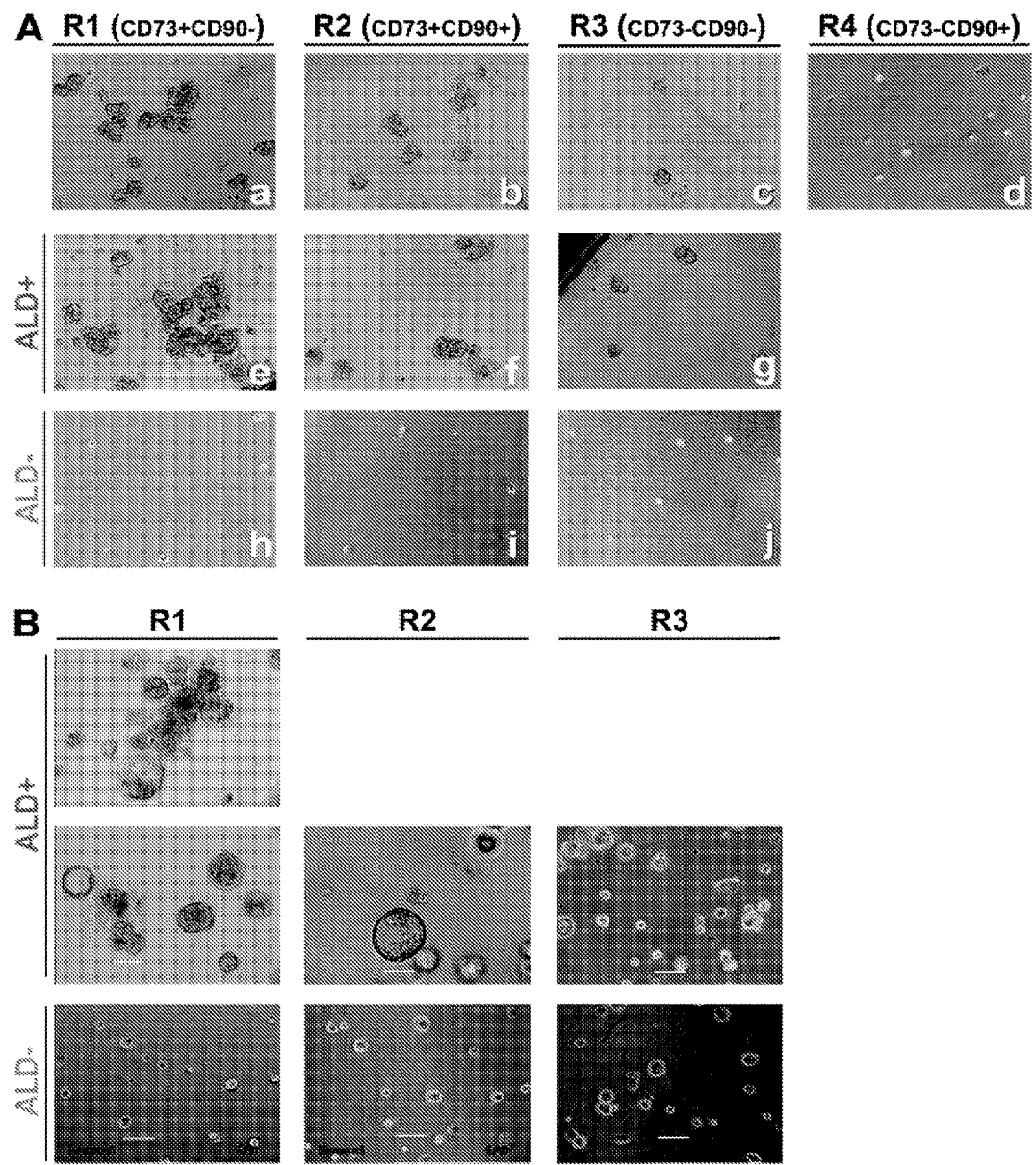
FIG. 9, Panels A-B: Self-renewal capacity and ability to recapitulate human mammary ductal-alveolar structures in vitro for R1-R4 human mammary epithelial subsets. (A) Representative images of mammosphere forming ability for: R1-R4 subsets (a-d); R1-R3 ALD+ subsets (e-g); and R1-R3 ALDsubsets (h-j) that failed to grow in suspension. Mammosphere frequency was: 3.86±0.13, 3.44±0.16, 3.54±0.14 and 3.46±0.19, for R1 at passages 1-4; 0.47±0.01, 0.56±0.05 and 0.54±0.05 for R2 at passages 1-3; 0.58±0.01 and 0.48±0.04 for R3 at passages 1-2; 5.56±0.07, 6.3±0.26, 6.12±0.24 and 5.9±0.18 for R1-ALD+ at passages 1-4; 0.64±0.02, 0.74±0.09 and 0.58±0.07 for R2-ALD+ at passages 1-3; 0.56±0.03 and 0.58±0.04 for R3-ALD+ at passages 1-2; 0.35±0.02, 0.44±0.05, 0.38±0.04 and 0.4±0.05 for unsorted cells at passages 1-4. Data are expressed as Mean±SEM (n=5). (B) Ductal-acinar and acinar structures generated from R1-ALD+ and R2-ALD+ mammosphere derived cells in colonogenic 3D Matrigel culture. R3-ALD+ and R1-R3 ALD− fail to generate ductal-acinar or acinar structures in these conditions.

Finally, in vitro differentiation potential was assessed by comparing the ability of R1-R3 ALD+ mammospheres-derived cells to form functional ductal-alveolar structures using a previously described 3D Matrigel cell culture system (MLA c) (FIG. 1, Panel B). This system tests the ability to recapitulate in vitro the spatial orientation and the complex architecture of the mammary tree observed in vivo. Primary human mammary epithelial cells organize in two types of multi-cellular structures: small acinus-like structures of luminal epithelial origin and solid spherical colonies of myoepithelial origin. To test the ability of R1-R3 ALD+ mammospheres-derived cells to develop branched, ductal-acinar structures and functional alveolar cells, single cells from dissociated mammospheres were plated at colonogenic densities in 3D Matrigel culture and cultivated for 3 weeks. Their growth was monitored daily to ensure that each structure was generated from a single cell and that individual structures did not merge. R1-ALD+ mammosphere-derived cells generated colonies with two morphologically distinct structures: 26% with branched, ductal-acinar structures, with the remaining ones forming acinus-like structures (FIG. 9, Panel B). In contrast, R2-ALD+ mammosphere-derived cells generated only acinus-like structures (FIG. 9, Panel B). R3-ALD+ mammosphere-derived cells as well as ALD− cells failed to generate any structure (FIG. 9, Panel B). When prolactin was added to the differentiation medium, R1-ALD+ but not R2-ALD+ mammosphere-derived cell cultures produced $\beta$-casein which was secreted in the central lumen of the acinar structures (data not shown). These data demonstrate once again that the R1-ALD+ population had true multi-lineage differentiation potential in vitro, whereas the R2-ALD+ and R3-ALD+ populations were significantly restricted in their differentiation potential.

Example 4

Figure 10:
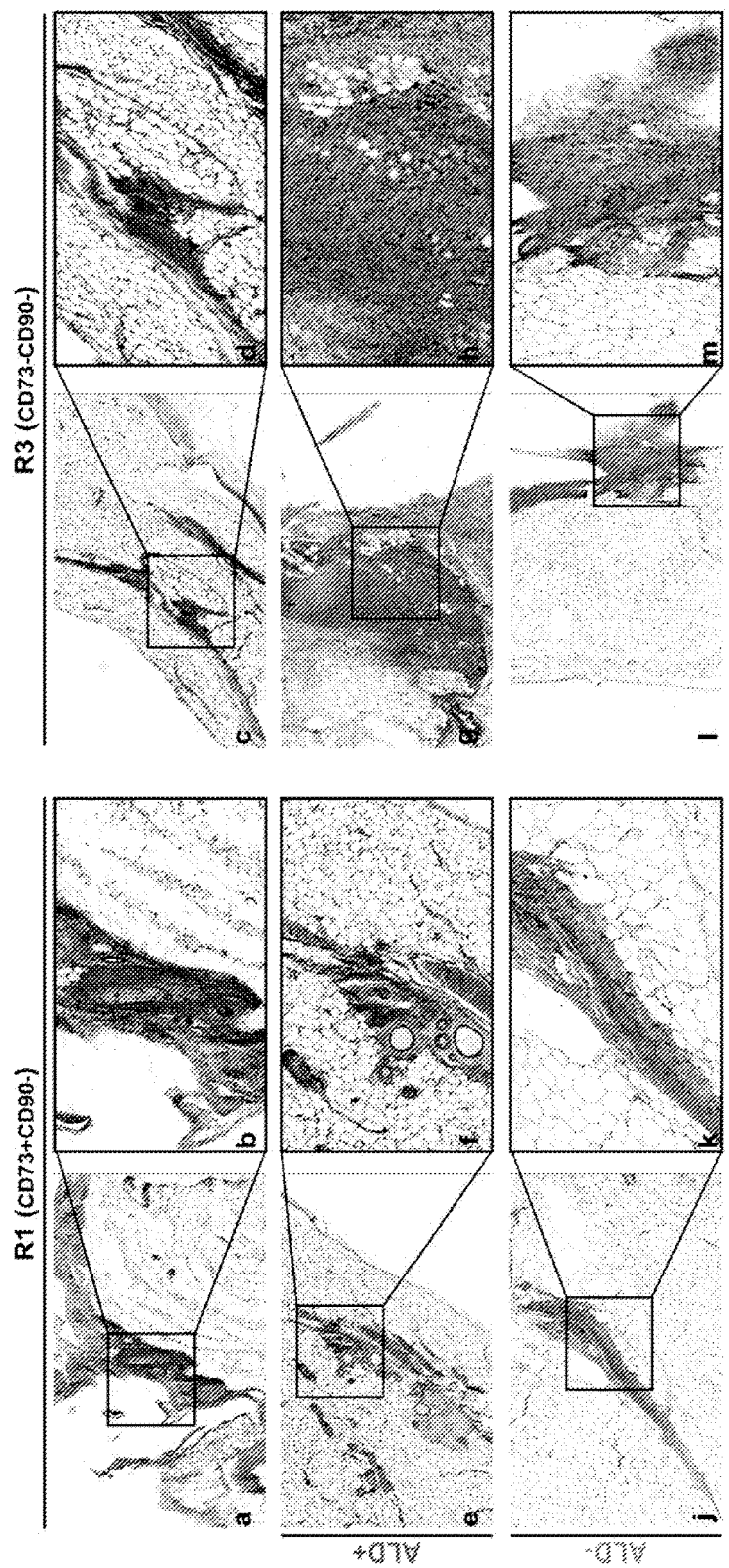
FIG. 10, Panels A-M: In vivo outgrowth potential of human mammary epithelial subsets transplanted into cleared and humanized mouse mammary fat pads. Hematoxylin and eosin staining of ducts generated by R1 ALD+/ALD− and R3 ALD+/ALD− subsets. The number of cells injected for each subset were as follows: R1: 15,000; R1-ALD+: 5,000; R1-ALD−: 30,000; R3: 300,000; R3-ALD+: 30,000; and R3-ALD−: 200,000. R2 and R4 subsets did not generate any outgrowth when transplanted into mouse mammary fat pads (data not shown). Data are representative of experiments performed on R1-R4, and R1 and R3 ALD+/ALD− subsets isolated from three reduction mammoplasties.

R1 ALDEFLUOR-Positive Cells are Capable of In Vivo Differentiation Along all Three Mammary Lineages To assess in vivo differentiation potential, the mouse model described by Kuperwasser et al. was utilized to evaluate the ability of R1-R4 to enrich for mammary gland regenerating activity in vivo. R1-R4 were transplanted into humanized cleared mammary fat pads of NOD/SCID mice (FIG. 10, Panels A-M). Only R1 had outgrowth potential, as shown by duct formation upon implantation of 15,000 cells (FIG. 10, Panels A-B). Importantly, this potential resided within its ALD+ fraction and was exhibited by transplanting as few as 5,000 cells (FIG. 10, Panels E-F). The R1-ALD− fraction was unable to generate any ducts even after transplanting 30,000 cells (FIG. 10, Panels J-K). R3, which also has ALDEFLUOR activity, failed to repopulate the mammary gland even after transplanting 300,000 cells (FIG. 10, Panels C-D). Thus, ALDEFLUOR activity alone does not dictate outgrowth potential.

Figure 3:
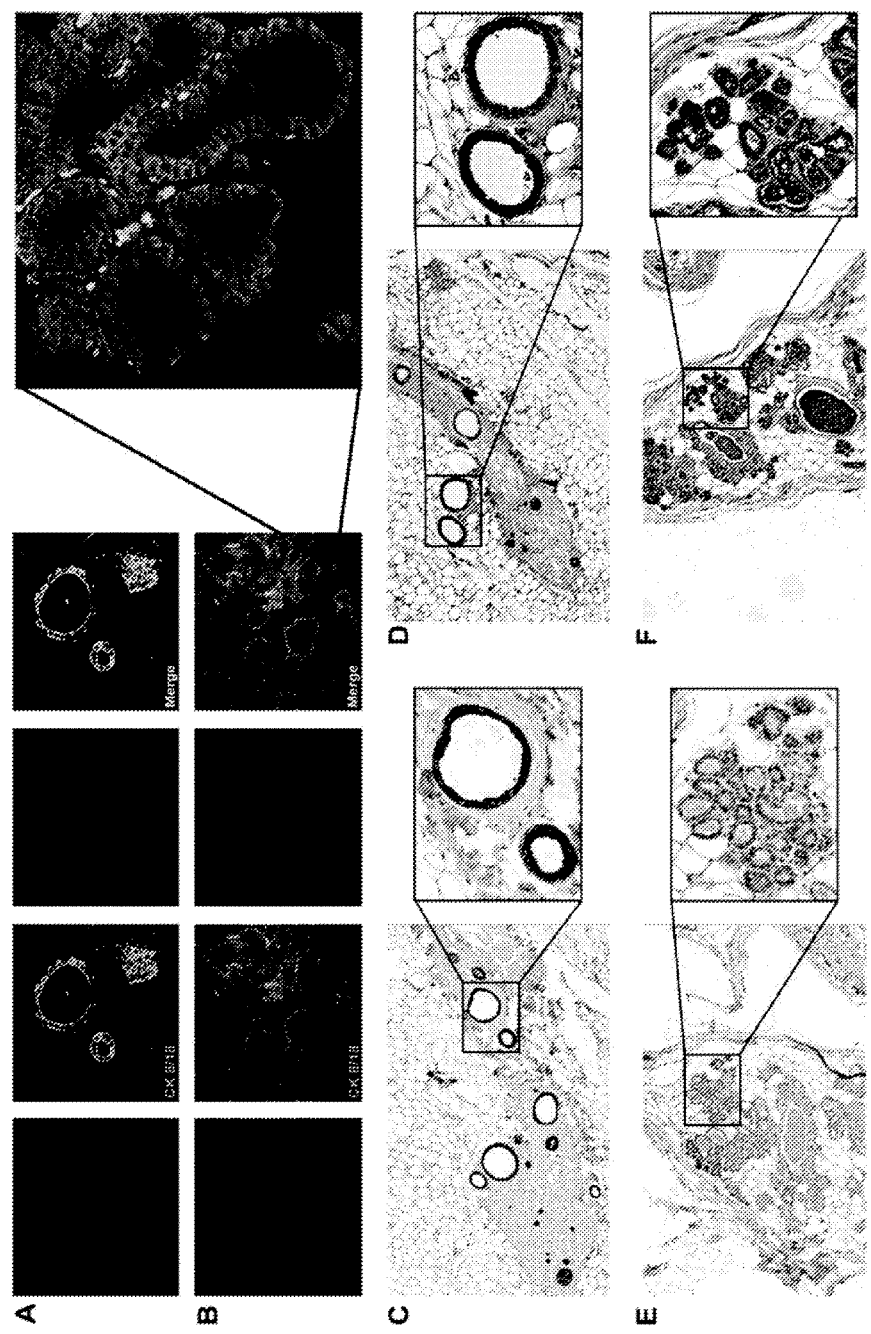
FIG. 3, Panels A-F: Characterization of the ductal outgrowths generated from the R1-ALD+ epithelial subset in humanized NOD/SCID mouse cleared fat pads. (A-B) Positive staining with human specific anti-CK8/18 and anti-αSMA antibodies documenting the human origin of acinar and ductal-acinar structures formed in mouse fat pads. Ducts consist of a luminal layer expressing CK8/18 and a myoepithelial layer expressing αSMA. (C and E) Specific staining for human CK8/18 showing human origin of the acinar and ducts. (D and F) Specific staining for human β-casein milk protein detected in secretory epithelial cells and alveoli lumen.

The human origins of the epithelial outgrowths were validated by immunostaining with human-specific antibodies for CK8/18 (luminal epithelial cells) and α-smooth muscle actin (α-SMA) (myoepithelial cells). As is the case in the human mammary tree, two kinds of ductal structures were generated in the animal host: acini and elaborate ductal-lobular outgrowths. Both were composed of a luminal epithelial layer, and an outer myoepithelial cell layer (FIG. 3, Panels A-B). To test whether the ductal structures from the transplantation had undergone complete functional differentiation, mice bearing the transplanted cells were mated and allowed to develop until day 18 of pregnancy. Human β-casein expression was observed within the luminal cells lining the acini and secretion in the lumina of the human ductal structures only in R1-ALD+ outgrowths (FIG. 3, Panels D and F). These observations further demonstrate the multipotent capacity of the R1 ALD+ cells both in vitro and in vivo.

Example 5

Figure 11:
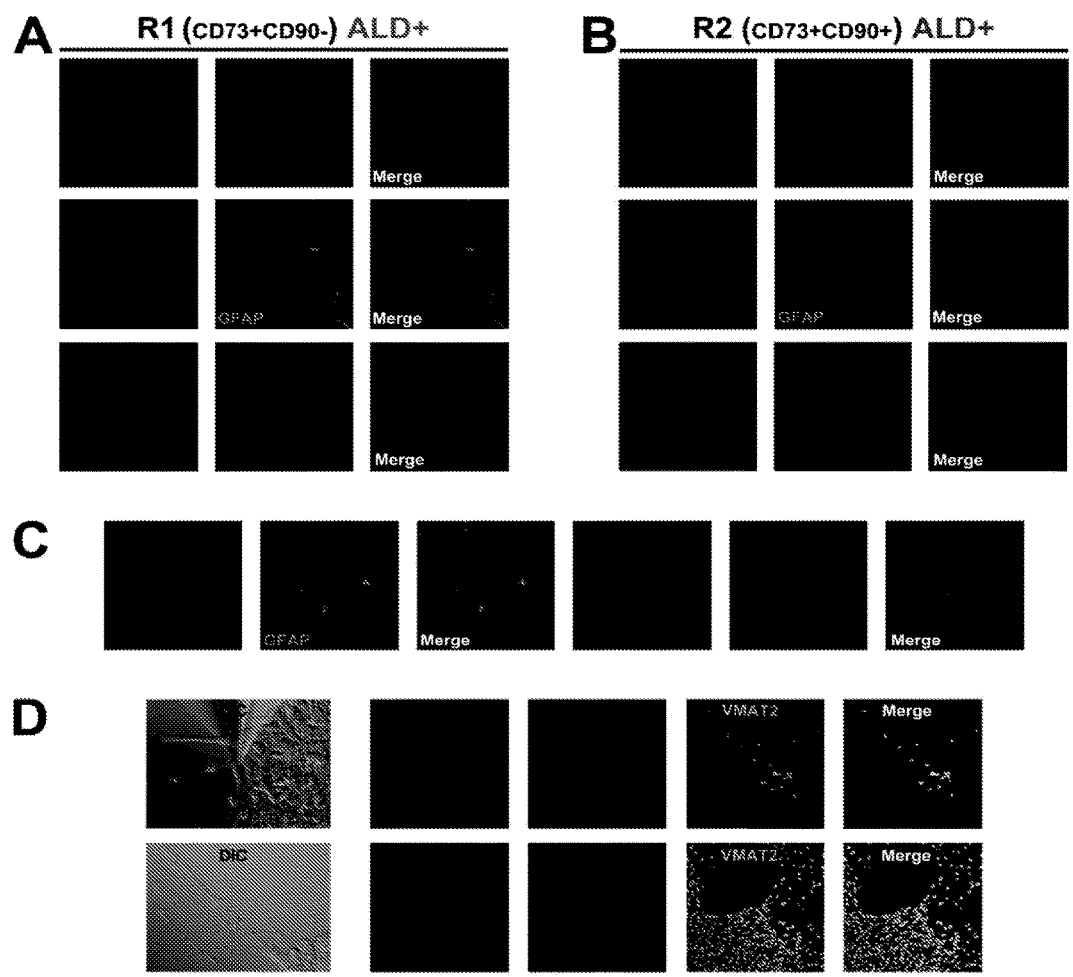
FIG. 11, Panels A-D: Neural differentiation potential of R1 and R2 subsets. Immunofluorescence analysis of R1-ALD+ (A) and R2-ALD+ (B) cells for nestin, GFAP and TUJ1/β-III-tubulin after neural differentiation. (C) Immunofluorescence analysis of hESC, H7 cells stained for GFAP and TUJ1/β-III-tubulin after neural differentiation. (D) Representative images of DIC showing R1-ALD+ (top panel) and hESC, H7 (bottom panel) differentiation into dopaminergic (DA) neurons. Corresponding immunofluorescence images are shown: DAPI (blue); tyrosine hydroxylase (TH, red); vesicular monoamine transporter 2 (VMAT2, green); merge (yellow).

R1 ALDEFLUOR-Positive Multipotent Cells are Capable of In Vitro Differentiation into Additional Ectodermal Lineages Since CD73 and CD90 are expressed on other stem cell populations, the capacity of R1-R4 subsets to differentiate into ectodermal lineages other than that of the mammary lineage, i.e. neural lineage, was determined. Neurosphere formation was restricted to R1 and R2 ALD+ fractions and maintained up to 3 passages. The phenotype of the spontaneously differentiated neural-lineage cells from the neurospheres was analyzed as described above. Although cells from both R1-ALD+ and R2-ALD+ neurospheres stained positive for the neural-specific marker, Nestin, they differed significantly in their potential to give rise to mature neurons (β-III-tubulin/TUJ-1-positive cells) or glial cells (GFAP-positive cells). R2-ALD+ neurosphere-derived cells differentiated only into the glial lineages, particularly astrocytes. In contrast, R1-ALD+ neurosphere-derived cells differentiated into both neurons and astrocytes, the percentage of differentiated neurons being much higher than astrocytes (89% vs. 11%, respectively) (FIG. 11, Panels A-B). This was also the case for human H7, ESCs (FIG. 11, Panel C).

Figure 4:
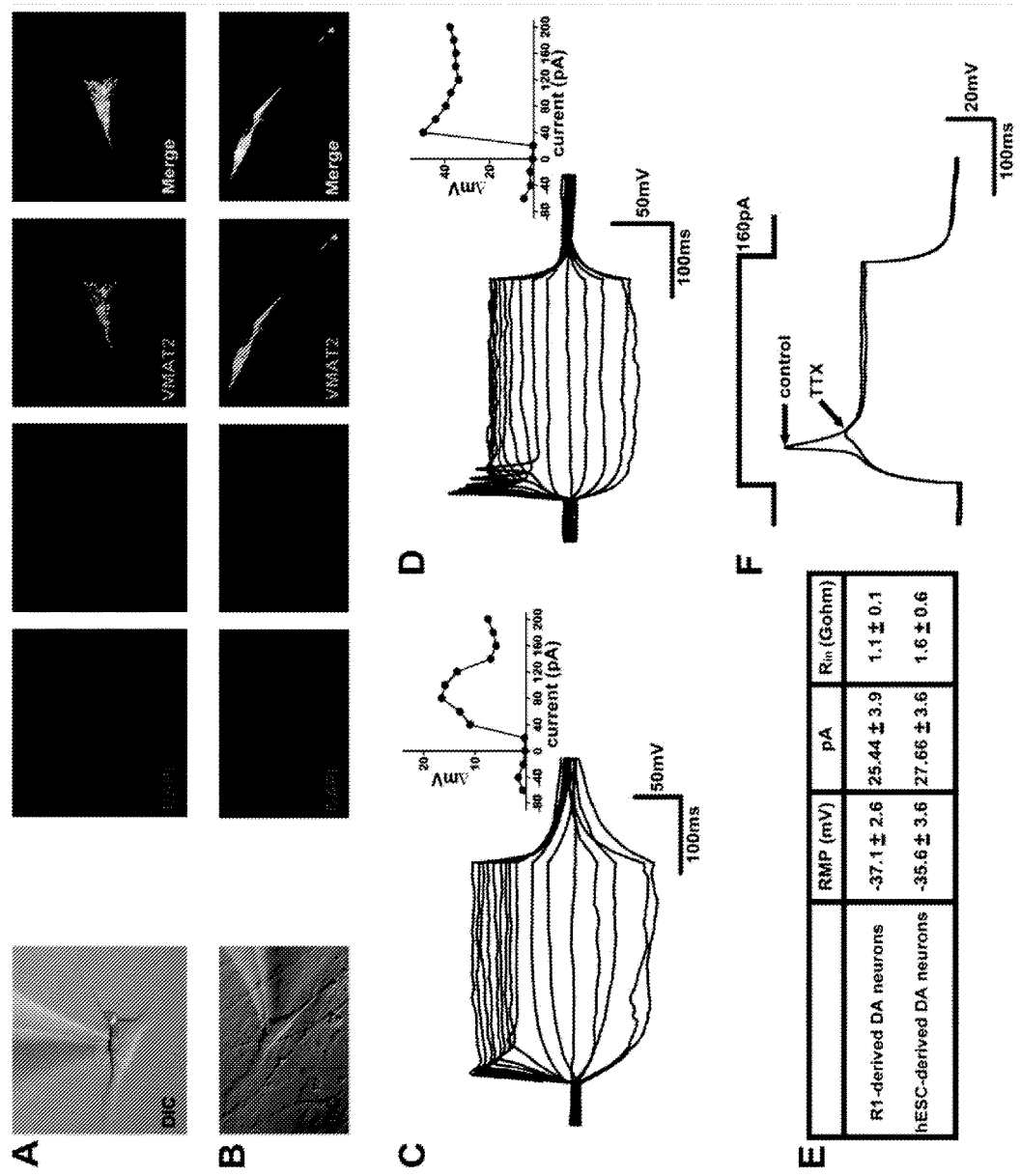
FIG. 4, Panels A-F: R1 epithelial cells can differentiate into dopaminergic neurons (DA-neurons) along the ectoderm lineage. DIC and corresponding immunofluorescence image of a single R1-ALD+-derived DA-neuron (A) and a single hESC-derived DA-neuron (B) used for electrophysiology. DAPI (blue); tyrosine hydroxylase (TH, red); vesicular monoamine transporter 2 (VMAT2, green); merge (yellow). (C) Voltage responses in R1-ALD+-derived DA-neuron shown in panel A and (D) hESC-derived DA-neurons in panel B. Insets: Peak amplitudes of voltage deflections as a function of current injection. (E) Table summarizing R1-ALD+-derived and hESC-derived DA-neurons membrane properties. No parameter showed significant difference between the two groups (p>0.05 with unpaired t-test, n=5 respectively). (F) Tetrodotoxin (TTX)-mediated blockage of single transient action potentials in R1-derived DA-neurons.

The ability of R1-ALD+ cells to differentiate into functional dopaminergic (DA) neurons was further assessed. After 21 days of differentiation, 80% of R1 ALD+ cells assumed a distinct pyramidal morphology with positive staining for the DA-specific markers tyrosine hydroxylase (TH) and vesicular monoamine transporter 2 (VMAT2) (FIG. 11, Panel D, top panel). It was then investigated whether these cells exhibited electrical membrane properties characteristic of neurons, including negative resting membrane potential (RMP) and action potential firing. To test this, whole-cell patch clamp recordings in R1-ALD+-derived and hESC-derived DA-neurons were performed (FIG. 4, Panels A-B). Both neuron populations showed similar negative RMPs (−37 and −36 mV, respectively), the values being comparable to those previously reported in immature hESC-derived neurons but higher than the ones typically observed in vivo (−58 mV). This reflects the expression of bona fide neuronal ion channels and the efficient regulation of ionic gradients across the cellular membrane.

To test whether R1-ALD+-derived and hESC-derived DA neurons could fire action potentials, both groups of cells were depolarized by injecting a series of depolarizing current steps. As expected, at depolarized membrane potentials, all five hESC-derived DA-neurons tested fired action potentials after a threshold membrane potential was reached in an all-or-none fashion (FIG. 4, Panel D). Similar all-or-none voltage deflections were observed in R1-ALD+-derived DA-neurons upon depolarization (FIG. 4, Panel C). The threshold at which action potentials were fired was similar in both cases, 52±12 pA and 84±27.9 pA, respectively. Importantly, unlike mature neurons that display spontaneous repetitive firing of action potentials, only one action potential was fired during each current step above threshold in both hESC- and R1 ALD+-derived DA-neurons, the latency becoming shorter at higher potentials. This observation once again supports the immature state of these DA-neurons, as indicated by their high input resistance, 1.6 and 1.1 GΩ, respectively (FIG. 4, Panel E). Importantly, the voltage deflection could be ablated by tetrodotoxin (TTX; FIG. 4, Panel F), indicating that this voltage deflection was mediated by Na+ channels, as expected for neurons. These results provide physiological evidence that hESCs and R1 ALD+ cells can differentiate into functional neurons that share very similar properties.

Example 6

R1 Multipotent Cells are Capable of in vitro Differentiation Along the Endoderm and Mesoderm Lineages Independent of ALDEFLUOR Expression Having established that R1-ALD+ could differentiate into various cell types along the ectoderm lineage, the differentiation potential of R1 along other somatic lineages, including endoderm and mesoderm, was investigated.

Figure 5:
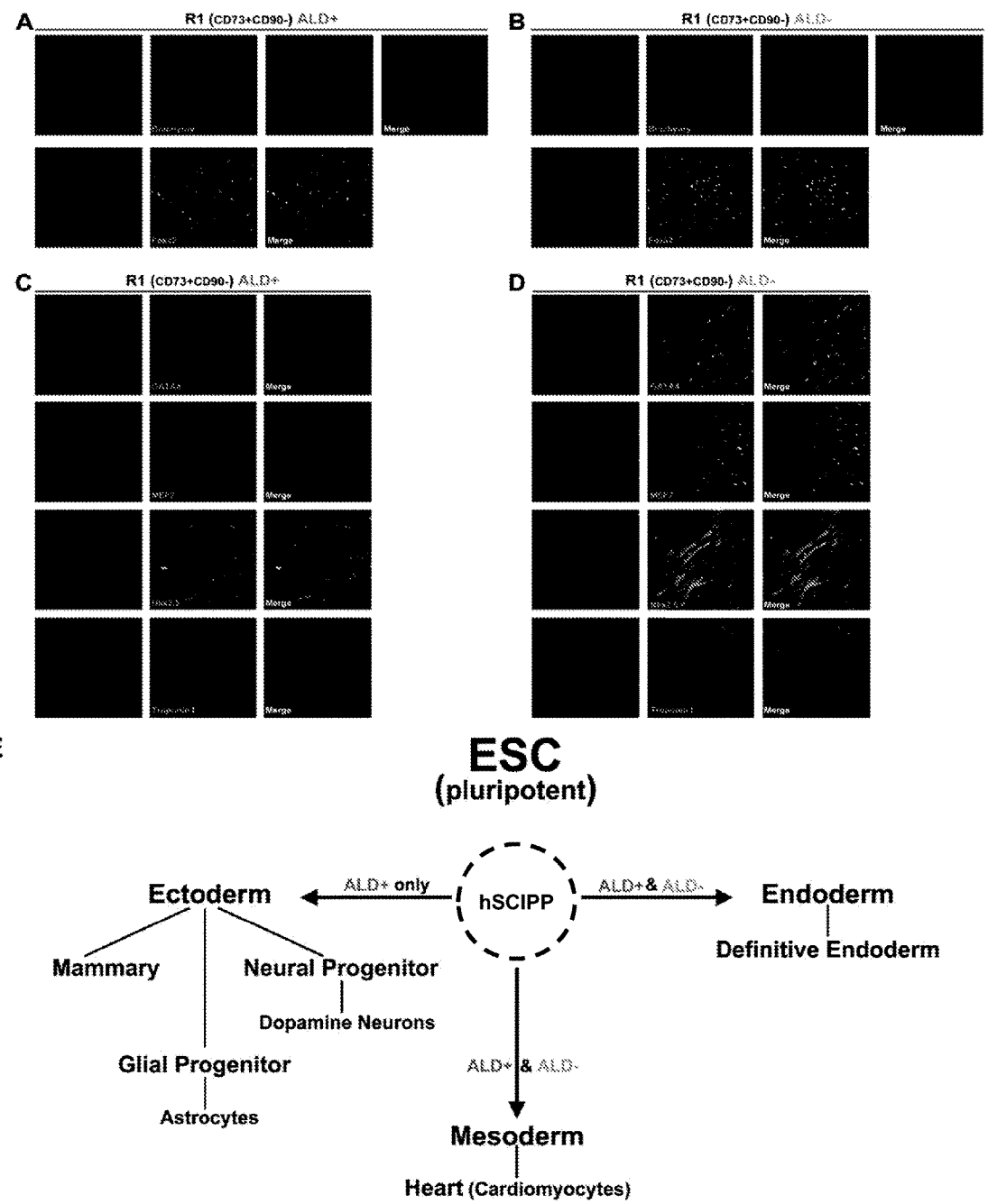
FIG. 5, Panels A-E: R1 epithelial cells are multipotent and can differentiate into definitive endoderm and mesoderm lineages. Immunofluorescence analysis of R1-ALD+ and R1-ALD− cells for (A-B) Sox17, Foxa2 and Brachyury after 3 days of differentiation towards definitive endoderm and (C-D) GATA4, MEF-2, Nkx2.5 and Troponin I after 6 days of cardiomyogenic differentiation. (E) Schematic representation of the differentiation potential of R1 cells towards the three germ layers, ectoderm, endoderm and mesoderm. SCIPP: human Somatic Cells with an Innate Potential for Pluripotency corresponding to the R1 multipotent epithelial subset.

To determine the potential for endodermal differentiation, R1-R4 were cultured under conditions that allow human ESCs to differentiate into definitive endoderm. After 3 days of differentiation, markers indicative of definitive endoderm (transcription factors SOX17 and FOXA2) were assessed by immunostaining. R3 and R4 failed to survive under these differentiation conditions. R2 survived but failed to proliferate, and showed very weak expression of SOX17 in the cytoplasm but did not express FOXA2 (data not shown). The only population that underwent differentiation towards definitive endoderm was R1, 40% of R1 cells expressing both SOX17 and FOXA2 in their nucleus (FIG. 5, Panels A-B). No cells expressed the mesoendoderm marker Brachyury, demonstrating a complete differentiation towards the definitive endoderm without contributions from a contaminating mesoendoderm lineage. Surprisingly, the differentiation potential was independent of ALDEFLUOR expression, both R1-ALD+ and R1-ALD− cells generating definitive endoderm (FIG. 5, Panels A-B).

To determine the potential for mesodermal differentiation, R1-R4 were exposed to growth factors previously reported to induce adult mesenchymal stem cells (MSCs) towards a cardiomyogenic cell lineage. Under these conditions, R1 and R2, irrespective of their ALDEFLUOR activity, survived, whereas R3 and R4 died. After differentiation, markers indicative of cardiomyogenic differentiation (transcription factors GATA4, MEF-2 and Nkx2.5, and Troponin I) were assessed by immunostaining. R1-ALD– cells uniformly expressed all the cardiomyogenic markers (FIG. 5, Panel D). R1-ALD+ cells exhibited expression of three out of the four markers: GATA 4, Nkx2.5 and Troponin I, but not MEF-2 (FIG. 5, Panel C). Differentiation potential of R2 was even further reduced, R2 cells expressing only Nkx2.5 (data not shown). As expected from previous reports, under these conditions, contraction of cardiomyocytes was not observed. Importantly, when R1 cells, with or without ALDEFLUOR activity, were cultured on human placental fibroblast feeders and grown in conditions that promote hESCs differentiation into cardiomyocytes (17), spontaneous beating was observed (data not shown).

CD73+CD90– (R1) cells exhibit multipotency, functional differentiation into epithelial and mesenchymal lineages and thus are human Somatic Cells with an Innate Potential for Pluripotency (hSCIPP).

Example 7

Figure 6:
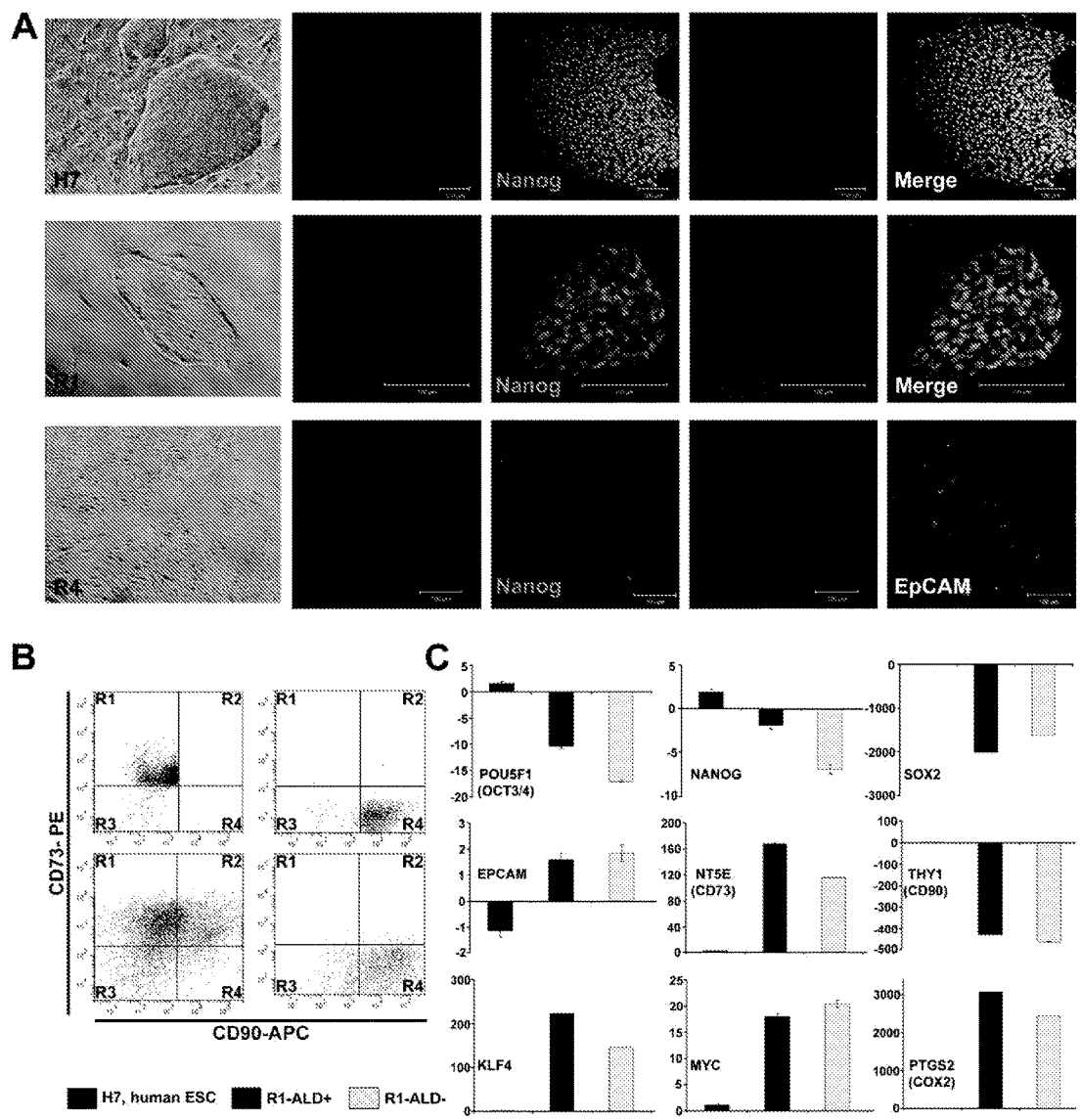
FIG. 6, Panels A-C: Individual R1 cells generate colonies that express pluripotency markers; R1 cells exhibit phenotypic fluidity. (A) Top and middle panels: phase contrast and immunofluorescence images of representative H7 and R1-derived colonies on irradiated fibroblast feeders showing expression of pluripotency markers Oct3/4 and Nanog. Bottom panels: phase contrast and immunofluorescence images of R4 cells on irradiated fibroblast feeders documenting lack of expression of Nanog and Oct3/4 but expression of the epithelial marker EpCAM. Sox2 protein is uniformly expressed in H7 cells and R1-derived colonies but not in R4 cells (data not shown). (B) Top panels: post-sort analysis of R1 and R4 epithelial cell subsets isolated from breast tissue (95.6% and 95.5% pure, respectively). Bottom panels: dynamic redistribution of R1 into all four epithelial subsets R1-R4 (R1=55%, R2=26%, R3=15% and R4=4%) after 4 weeks in culture allowing expansion of cells in an undifferentiated state. The R4 subset, even after 8 weeks of extended culture, is mostly limited to its initial distribution (R1=0.14%, R2=1.99%, R3=10.70% and R4=88.07%). (C) Quantitative real time PCR analysis for pluripotent, reprogramming and stress associated markers in H7 hESCs, R1-ALD+ and R1-ALD− epithelial subsets, using endogenous transcriptspecific primers. Transcript expression levels, normalized to GAPDH expression, are relative to H9 human ES cells. Error bars indicate standard deviations (n=4).
Figure 12:
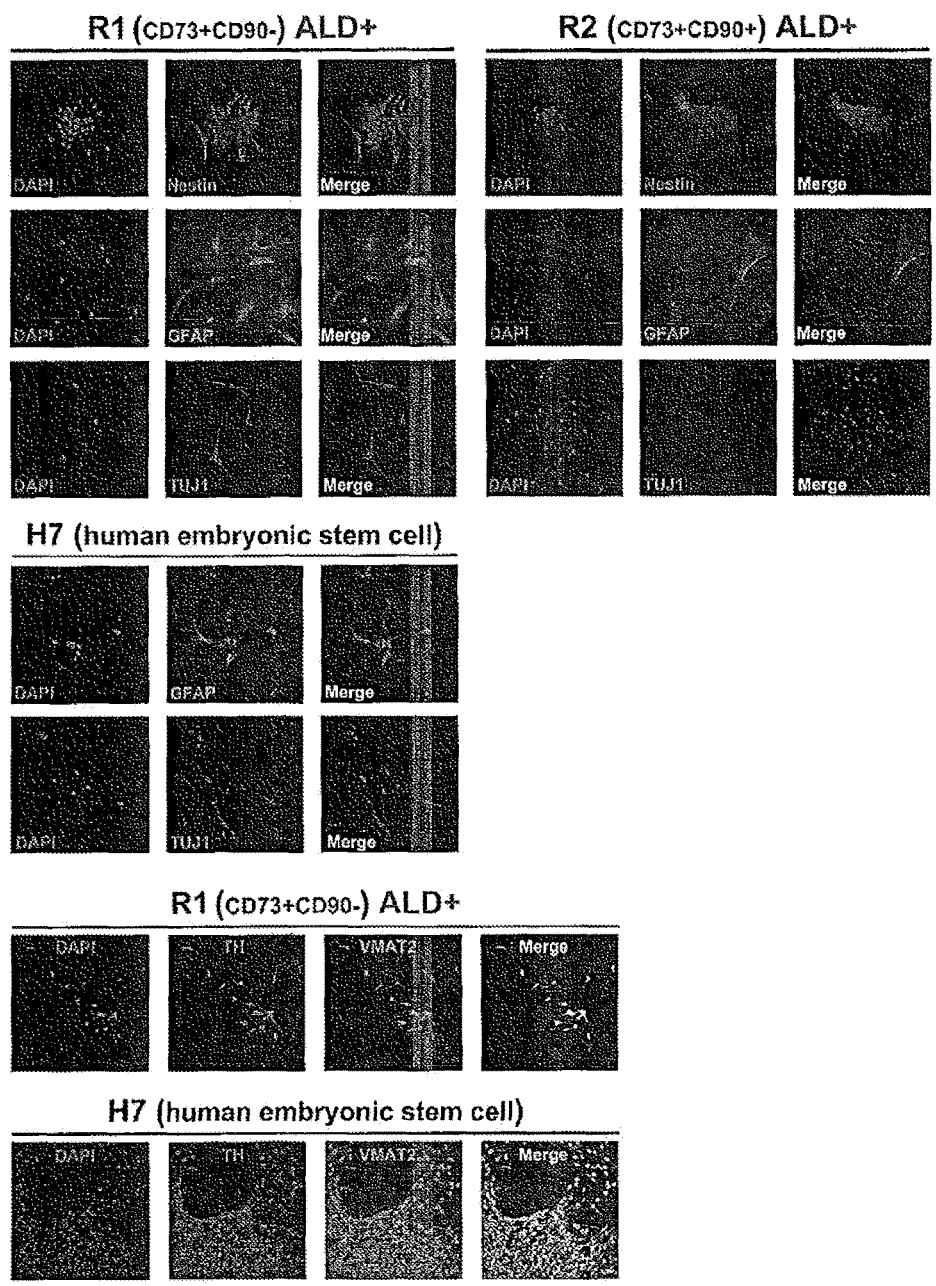
FIG. 12: Full lineage potential of subclones derived from a single R1 cell. Immunoflurescence analysis for (A) ectodermal lineage: nestin, Pax6, TUJ1/β-III-tubulin, TH and NCAM after neural differentiation; (B) endodermal lineage: Foxa2, Sox17 and Brachyury after definitive endodermal differentiation and (C) mesodermal lineage: GATA4, MEF2 and Nkx2.5 after cardiomyocyte differentiation.

Individual R1 Cells Express Certain Phenotypes Characteristic of Embryonic Stem Cells A single R1 cell, when isolated from primary tissue and placed in conditions that allow expansion of pluripotent human ES cells (23), forms a colony that, by 14 days, robustly expresses pluripotency genes previously documented in ES cells, Nanog, Oct3/4 and Sox2 (FIG. 6, Panel A). This is not observed for R2-R4. Progeny of these single cell-derived subclones were divided into three parts, placed in differentiation conditions described above and shown to generate neurons, cardiomyocytes and definitive endoderm (FIG. 12). Short Tandem Repeat analysis was used to confirm the origin and individual identity of the parental breast cell population and its mesodermally-differentiated R1 derivative (FIG. 14). Thus, these Somatic Cells display an Innate Potential for Pluripotency (SCIPP) when placed in the proper conditions.

Current studies have demonstrated that a general feature of a stem cell phenotype includes the generation of robust dynamic heterogeneity. This phenotypic fluidity can be measured using flow cytometry and monitoring the distribution of a myriad of expression changes. In ES cells this is exhibited by fluctuations in Nanog expression which correlate with a distribution of probabilities of differentiation. In haematopoietic progenitors, ScaI expression serves this function. Expression of the cell surface markers CD73 and CD90 were used to document the dramatic plasticity of the R1 population (FIG. 6, Panel B). Indeed, the R1 population exhibits a dynamic redistribution towards the four initial states of R1-R4. Associated with the redistribution of the original R1 population is the acquisition in restrictions in differentiation potential (data not shown).

Example 8 hSCIPP Display a Gene Expression Signature that Distinguishes them from hESCs

Since hSCIPPs can exhibit pluripotency phenotypes along the three germ lineages, the molecular commonalities and distinctions between this newly characterized hSCIPP population and a well-characterized hESC population were assessed. To this end, transcript expression levels of 43 genes were measured, including key pluripotency marker genes and known reprogramming factors, in R1 and R4 populations sorted from four reduction mammoplasties using quantitative RT-PCR (qRT-PCR). This analysis revealed that RI-ALD+ and R1-ALD– exhibited a similar expression profile and that this profile, although sharing some commonalities with hESCs, also clearly distinguishes them from hESCs. One shared characteristic between hSCIPPs and hESCs is the high expression of pluripotency genes, such as Oct3/4 and Nanog, compared to differentiated cells (FIG. 6, Panels A-C and FIG. 15). Unlike hESCs, hSCIPP express much reduced levels of certain epigenetic plasticity markers, such as Dnmt3b, while robustly expressing the critical reprogramming factors, Klf4 and Myc, and the stress marker Ptgs21Cox2 (FIG. 6, Panels A-C and FIG. 15). Thus, hSCIPPs exhibit a unique expression profile that supports their potential for pluripotency and clearly distinguishes them from hESCs.

Example 9

Cell Surface Markers Controlled by P16$^{INK4a}$

Figure 21:
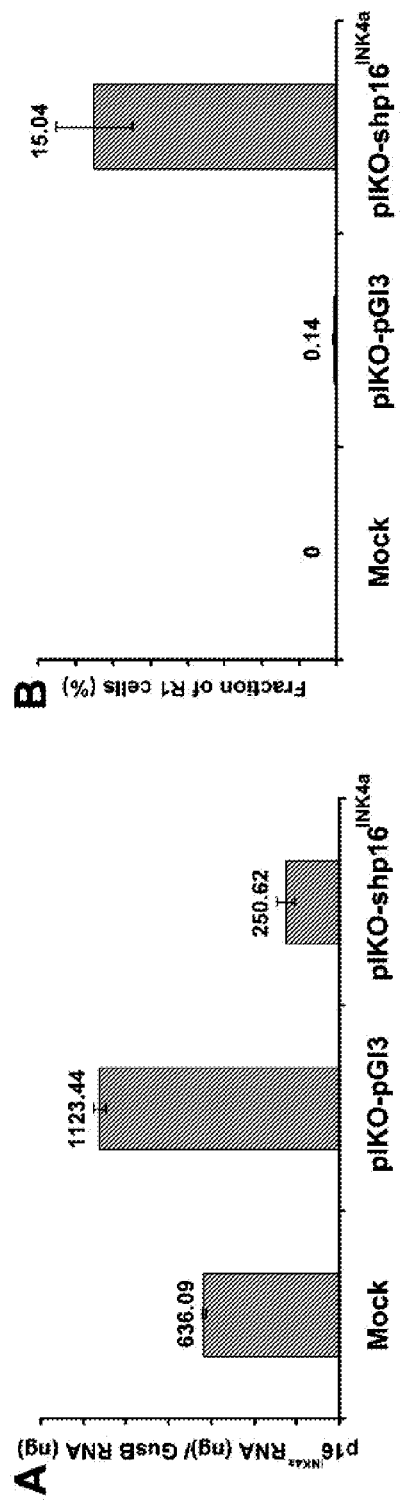
FIG. 21, Panels A-B: Repression of $p16^{INK4a}$ and modulation of expression of cell surface markers CD73 and CD90. (A) Transcript levels of $p16^{INK4a}$ (CDKN2A) in Mock (primary mammary epithelial cells), p1KO-pG13 (cells transduced with control vector) and p1KO-shp16$^{INK4a}$ (cells transduced with short hairpin to $p16^{INK4a}$) normalized to the housekeeping gene Glucuronidase B (GusB). (B) Graph of the average percentage of CD73$^+$CD90$^-$ (R1) cells in the populations measured by FACS analysis in (A) from three independent transductions. Error bars indicate standard deviations (n=3).

Repression of p16$^{INK4a}$ is a key stem cell phenotype. Mice engineered for knock-out of BMI-1, a polycomb repressor protein that inhibits p16$^{INK4a}$ transcription and activity, fail to generate hematopoietic and neural stem cells. Functionally, repression of p16$^{INK4a}$ in stem cells not only inactivates cell cycle arrest in response to stress but, additionally, enables epigenetic plasticity for differentiation. Repression of p16$^{INK4a}$ might also modulate expression of cell surface markers that could be used for the prospective isolation of cells with stem cell properties. Comparative gene expression profiling of human mammary epithelial cells with or without naturally repressed p16$^{INK4a}$ identified a dramatic co-incident over-expression and downregulation of CD73 and CD90, respectively. To confirm the causal role of p16$^{INK4a}$ in modulating these proteins, human mammary epithelial cells with shp16 were assayed for expression of CD73 and CD90 using flow activated cell sorting (FACS). A 61-77% reduction in basal p16$^{INK4a}$ protein expression was accompanied by a dramatic shift from the CD73$^-$CD90$^+$ to the CD73$^+$CD90$^-$ fraction, resulting, on average, in >100-fold increase in CD73$^+$CD90$^-$ cells (FIG. 21).

Having identified CD73$^+$CD90$^-$ as a potential signature for mammary stem cells, nineteen disease-free human breast tissues (reduction mammoplasties) were analyzed for the presence of CD73$^+$CD90$^-$ cells. All tissues were devoid of visible disease, bacterial, fungal or viral contamination and exhibited a normal diploid 46, XX karyotype (Examples, and FIG. 22). Freshly isolated single cells were first depleted of the lineage-positive (Lin$^+$) fraction (hematopoietic, endothelial and leukocytic cells) (FIG. 7, Panel A). The resultant lineage-negative (Lin$^-$) population, which expresses the epithelial cell surface marker EPCAM, was fractionated into four subpopulations, CD73$^+$CD90$^-$ (R1) (5.3%), CD73$^+$CD90$^+$ (R2) (1.9%), CD73$^-$CD90$^-$ (R3) (84.6%) and CD73$^-$CD90$^+$ (R4) (8.2%) (FIG. 1, Panels A and C, and FIG. 33), using the gating shown in FIG. 7, Panel B. Fractions R1-R4 were subsequently tested in standard assays for mammary stem cell self-renewal and multi-lineage potential as described below.

Example 10

Rare Cells Exhibit Breast Multipotency

Figure 16:
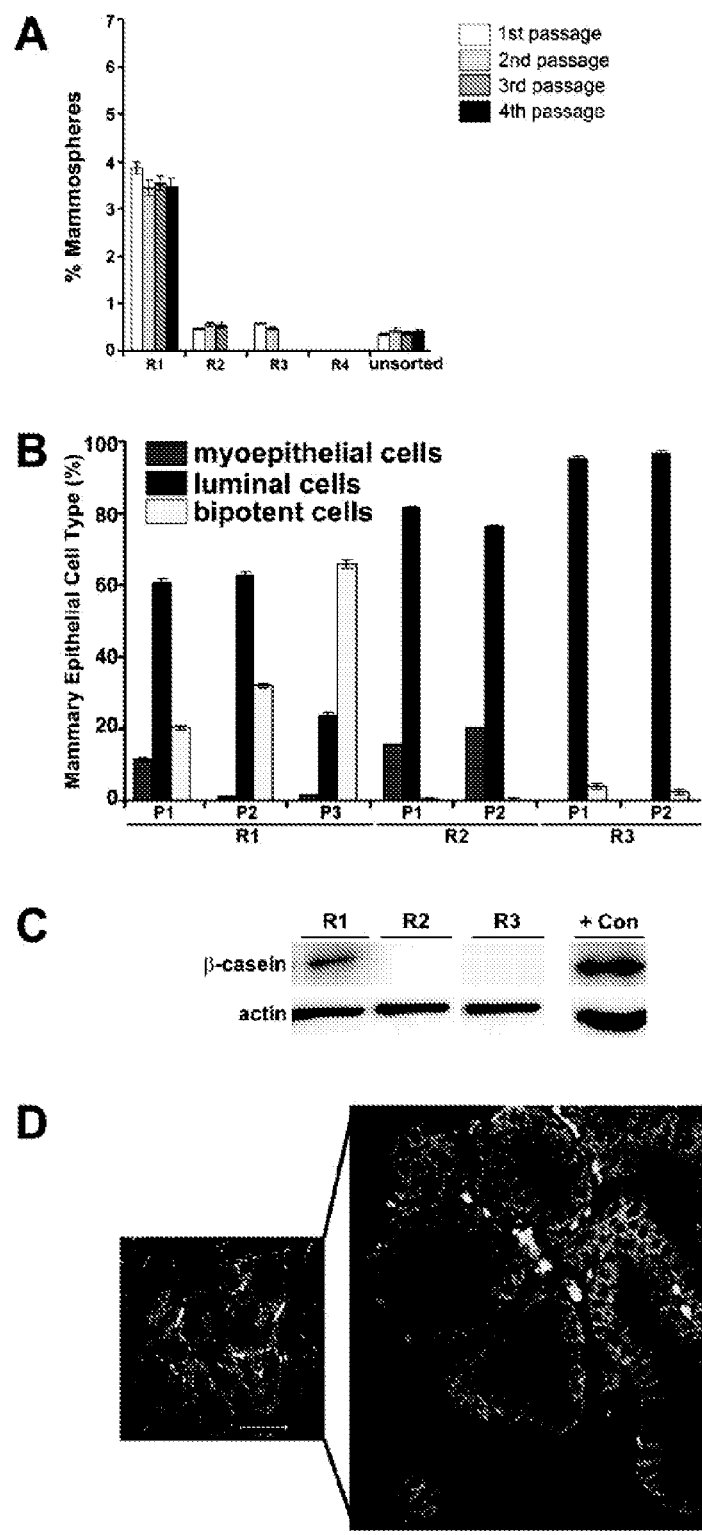
FIG. 16, Panels A-D: R1 cells have self-renewal and mammary multilineage capacity. (A) Mammosphere initiating capacity for R1-R4 subpopulations was assessed using 10,000 cells (first passage) and 1,000 cells (subsequent passages). See FIG. 23, Panel A for % mammospheres expressed as average±SEM (n=5). (B) FACS analysis of cells dissociated from successive passages of mammospheres and stained for α-6-integrin/CD49f (myoepithelial) and MUC-1 (luminal) markers. P=passage. (C) Western blot analysis for anti-human β-casein in R1-R3 mammosphere-derived cells. Loading control: actin. Positive control: BT-20 cell line. (D) Ducts consisting of a luminal layer expressing CK8/18 (green) and a myoepithelial layer expressing αSMA (red) stained with human specific antibodies documenting the human origin of structures formed in mouse fat pads. Scale=100 μm.

Self-renewal capacity was assessed by evaluating sphere initiation efficiency of single cells, cultured as mammospheres and subjected to serial passages (FIG. 1, Panel B). While many cell populations could produce initial mammospheres, even when plated at 1 cell/well in 96-well plates, only cells that demonstrated serial mammosphere formation possessed stem cell properties. Robust and sustained mammosphere generation was observed only for cells within R1 and extended to 8 passages (FIG. 1, Panel C; FIG. 16, Panel A; and FIG. 23, Panel A). Importantly, as expected for a rare stem cell population, only a small fraction (~3%) of CD73$^+$ CD90$^-$ cells (R1 cells), accounting for only 0.16% of total epithelial cells, exhibited this complete and sustained clonogenic mammary self-renewal capacity in vitro.

To test further which mammary cells had stem or progenitor cell properties, mammosphere-derived cells from R1-R3 were assessed using three in vitro Mammary Lineage Assays (MLA a-c; FIG. 1, Panel B) and one in vivo mammary gland regeneration assay (FIG. 1, Panel B).

Figure 18:
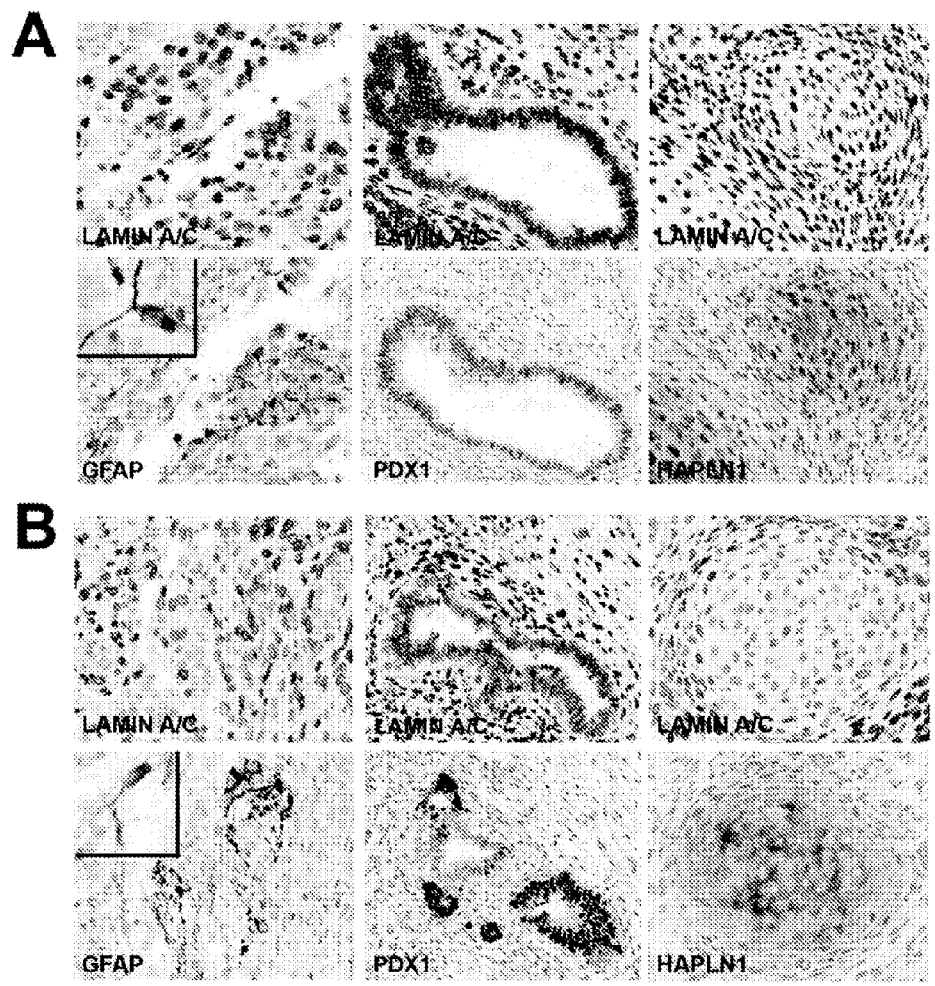
FIG. 18, Panels A-B: R1 cells form teratomas. R1 cells directly isolated from reduction mammoplasty (A) or R1 clones expanded from single cells in culture (B) were grafted under the renal capsule of SCID/BEIGE mice. Teratomas, harvested 16 weeks after injection, were paraffin-embedded, sectioned and stained for the pan-human-specific marker lamin A/C to document the human origin of these structures (upper panels) and for lineage-specific markers (lower panels): glial (ectodermal) marker, GFAP (250×); pancreatic (endodermal) marker, PDX1 (150×); or cartilage (mesodermal) marker, HAPLN1 (250×). Insets: 500× views of GFAP-positive cells.
Figure 23:
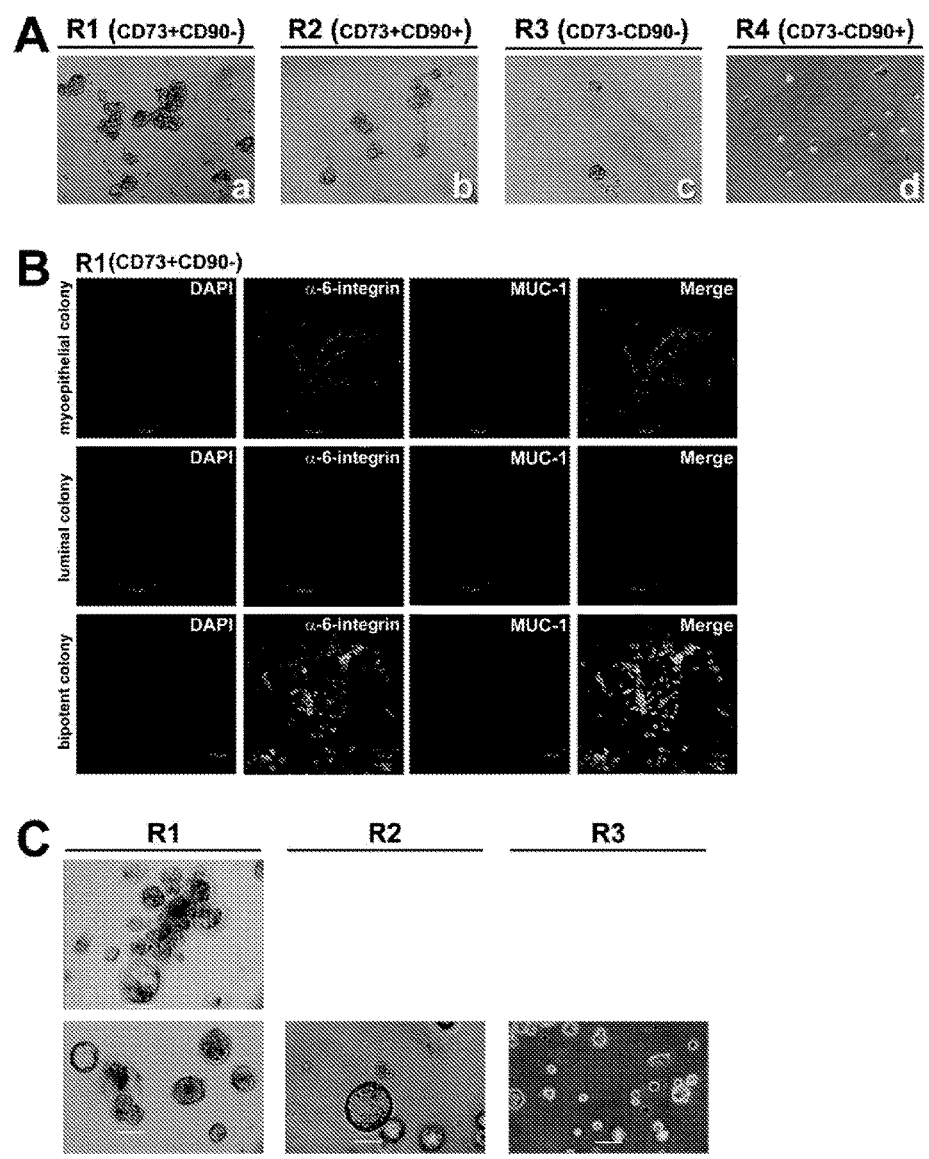
FIG. 23, Panels A-C: Self-renewal capacity and ability to recapitulate luminal, myoepithelial and ductal-alveolar structures in vitro for R1-R4 human mammary epithelial subpopulations. (A) Representative images of mammosphere forming ability for R1-R4 subpopulations (a-d). Mammosphere frequency was: 3.86±0.13, 3.44±0.16, 3.54±0.14 and 3.46±0.19, for R1 at passages 1-4; 0.47±0.01, 0.56±0.05 and 0.54±0.05 for R2 at passages 1-3; 0.58±0.01 and 0.48±0.04 for R3 at passages 1-2; 0.35±0.02, 0.44±0.05, 0.38±0.04 and 0.4±0.05 for unsorted cells at passages 1-4. Data are expressed as average±SEM from five tissue samples (n=5). (B) Representative images of first passage dissociated R1-mammospheres grown in differentiating conditions for 14 days and immuno-stained for α-6-integrin/CD49f and MUC-1. R1-mammosphere-derived cells generated monolineage myoepithelial colonies immunostained for α-6-integrin, monolineage luminal colonies immunostained for MUC-1 and bipotent colonies immunostained for both α-6-integrin and MUC-1. (C) Ductal-acinar and acinar structures generated from R1 and R2 mammosphere derived cells in colonogenic 3D Matrigel culture. R3 failed to generate ductal-acinar or acinar structures under these conditions. Scale=100 μm.

In the first assay, in vitro lineage differentiation potential was assessed on serial passages of mammosphere-derived cells by flow cytometry and colony morphology analysis. Mammospheres derived from R1-R3 were dissociated into single cells, cultured in suspension to test for self-renewal capacity and multi-lineage potential and an aliquot was plated on collagen-coated coverslips at colony-producing densities (MLA a; FIG. 1, Panel B). Differentiation was monitored by staining cells for expression of mammary luminal and myoepithelial markers, MUC-1 and CD49f (α-6-integrin), respectively (FIG. 23, Panel B). Flow cytometry identified R1 as the only population with multi-lineage potential. The first mammosphere passage generated all three lineages. With subsequent passages, the bipotent progenitors (MUC-1$^+$/CD49f$^+$) increased over passages 1-3: 20%, 32% and 66%, respectively (FIG. 16, Panel B) at the expense of the differentiated progeny. Using the complementary morphologic colony-producing assay, R1 mammosphere-derived (single) cells differentiated into three types of colonies: colonies containing exclusively myoepithelial cells (FIG. 16, Panel B and FIG. 23, Panel B: top), exclusively luminal epithelial cells (FIG. 16, Panel B; and FIG. 23, Panel B: middle) or cells of both lineages as well as bipotent cells with co-expression of both lineage markers (FIG. 16, Panel B and FIG. 18, Panel B; bottom). This differentiation potential was maintained in subsequent passages (data not shown). In contrast, both flow cytometry (FIG. 16, Panel B) and morphological analysis (data not shown) demonstrated that R2 and R3 mammosphere-derived cells differentiated predominantly into myoepithelial and luminal colonies, or only into luminal colonies, respectively Acquisition of functional alveolar differentiation was assessed by cellular production of β-casein in the second assay (MLA b; FIG. 1, Panel B and FIG. 16, Panel C). Cells derived from R1-R3 mammospheres were allowed to differentiate on a collagen substratum, overlaid with reconstituted basement membrane gel devoid of growth factors (Matrigel), supplemented with prolactin and further cultured. Under these conditions, only R1 mammosphere-derived cells produced 3-casein, consistent with alveolar differentiation. R2-R3 produced luminal cells that failed to differentiate in the presence of prolactin. These cells may be like the mature luminal cells reported by Lim et. al. that fail to respond to lactogenic cues, as well as fail to form ducts/lobules in 3D Matrigel culture.

The third in vitro differentiation assay (MLA c; FIG. 1, Panel B) compared the ability of R1-R3 mammosphere-derived cells to organize into two types of multi-cellular structures observed in vivo: small acinus-like structures of luminal origin and solid spherical colonies of myoepithelial origin. Single cells from dissociated mammospheres (R1-R3) were cultured at colony-producing densities in 3D Matrigel. Only R1 mammosphere-derived cells generated both structures: 26% branched, ductal-acinar structures and 74% acinus-like structures (FIG. 23, Panel C). When prolactin was added to the differentiation medium, R1 but not R2 mammosphere-derived cell cultures produced β-casein (data not shown). Thus, the R1 population exhibited true multi-lineage differentiation potential in vitro, whereas the R2 and R3 populations were significantly restricted in potential.

Figure 24:
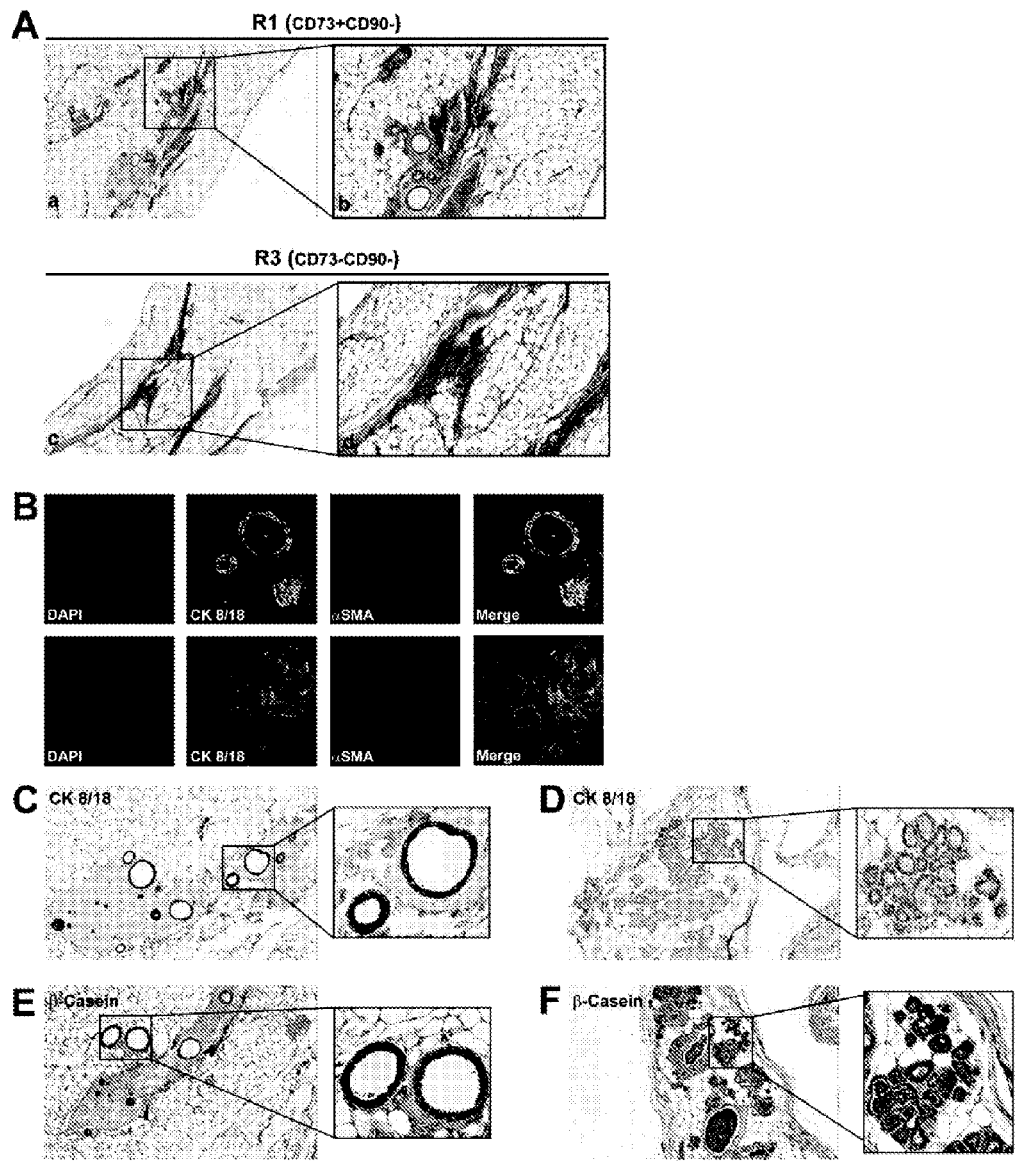
FIG. 24, Panels A-F: In vivo outgrowth potential of human mammary epithelial subpopulations transplanted into cleared and humanized mouse mammary fat pads. (A) Hematoxylin and eosin staining of ducts generated after injection of 5,000 and 300,000 cells from the R1 and R3 subpopulations, respectively. R2 and R4 subpopulations did not generate any outgrowth when transplanted into mouse mammary fat pads (data not shown). (B) Immunofluorescence staining of luminal layers with human-specific anti-CK8/18 and myoepithelial layers with anti-αSMA antibodies documenting the human origin of acinar and ductal-acinar structures formed in mouse fat pads. (C and D) Specific staining for human CK8/18 showing human origin of the acini and ducts. (E and F) Specific staining for human β-casein milk protein detected in secretory epithelial cells and alveolar lumen. Data are representative of experiments performed on R1-R4 subpopulations isolated from three reduction mammoplasties.

Finally, the ability of R1-R4 to enrich for mammary gland regenerating potential in vivo was evaluated as described above. R1-R4 were sorted and directly transplanted into cleared, humanized mammary fat pads of NOD/SCID mice. Only R1 had outgrowth potential, as shown by duct formation upon implantation of as few as 5,000 cells (FIG. 24, Panels A-B). R2, R3 (FIG. 24, Panel A) and R4 failed to repopulate the mammary gland even after transplantation of up to 300,000 cells. As observed in the human mammary tree, the acini and ductal-lobular outgrowths generated in the host were composed of a luminal layer and an outer myoepithelial cell layer (FIG. 16, Panel D). The human origin of these epithelial outgrowths was validated with human-specific antibodies for CK8/18 (luminal cells) and α-smooth muscle actin (α-SMA) (myoepithelial cells). To test whether these human ductal structures had undergone complete functional differentiation, mice were mated and mammary glands were harvested at day 18 of pregnancy. Human β-casein was expressed within luminal cells lining the acini and secreted into the lumina of human ductal structures only in R1 outgrowths (FIG. 24, Panels C-F). These results established the mammary gland multipotent capacity of the R1 cells both in vitro and in vivo.

Example 11

Differentiation into Additional Lineages

Figure 19:
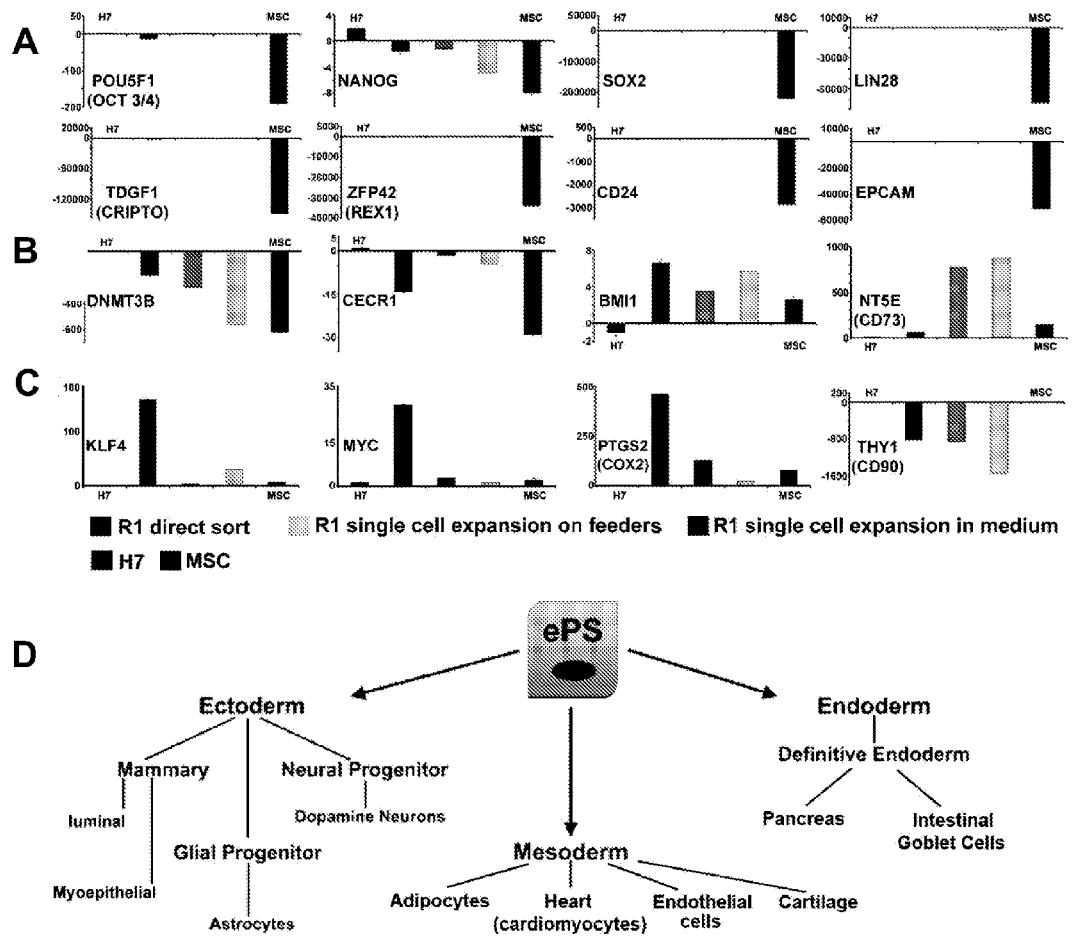
FIG. 19, Panels A-D: Single cell-derived R1 colonies express pluripotency markers. (A-C) Quantitative real-time PCR analysis for pluripotent, stress and reprogramming markers in H7 hESCs, freshly sorted R1 epithelial subpopulations, individual R1 single cell-derived colony on feeder layer, R1 subclone in expansion medium and human MSCs. Transcript levels, normalized to GAPDH expression, relative to H9 hESCs. Error bars indicate standard deviations (n=3). (D) Schematic representation of the differentiation potential of ePS cells, human endogenous Pluripotent Somatic cells, towards ectoderm, endoderm and mesoderm.

Analysis of the R1-R4 subpopulations by qPCR array revealed distinctive expression of genes in the R1 population that confer multi- and pluripotency (FIG. 19, Panel A). Thus, the capacity of R1-R4 subpopulations to differentiate into other ectodermal and mesoendodermal lineages was examined.

Figure 25:
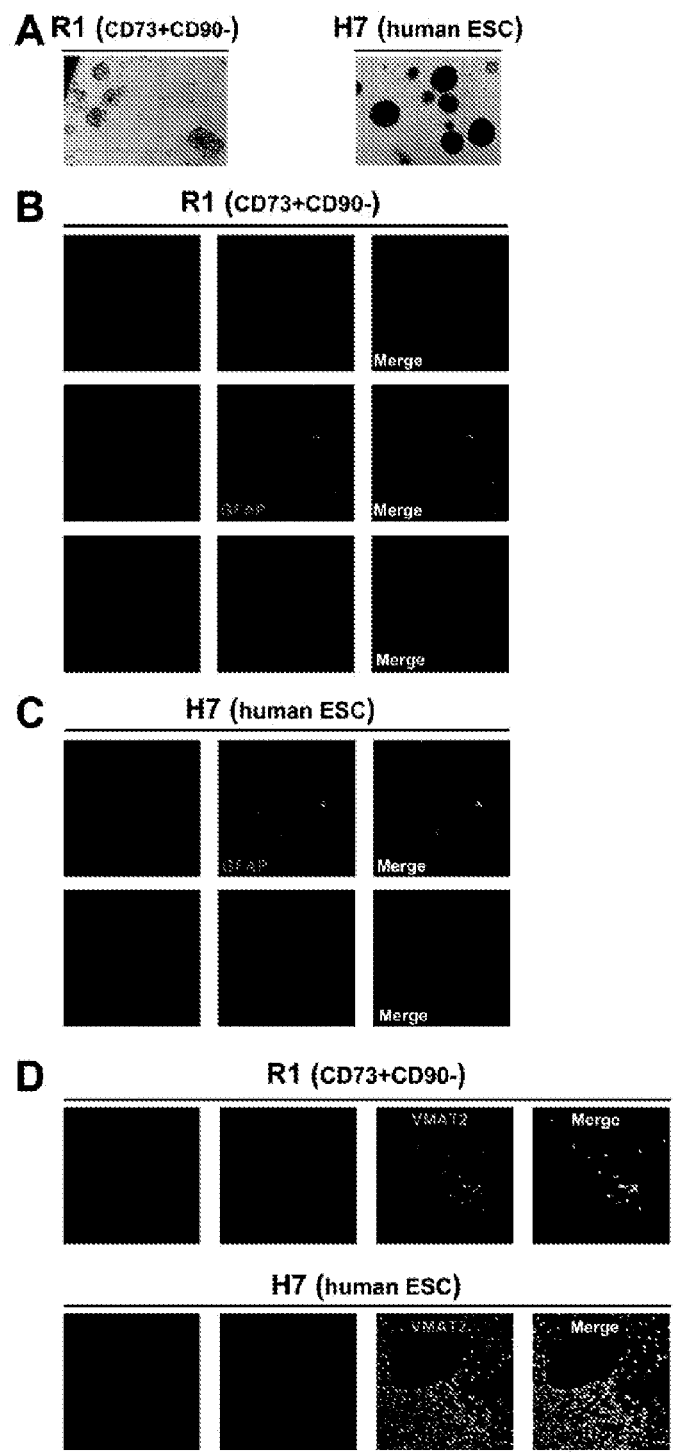
FIG. 25, Panels A-D: Neural differentiation potential of R1 cells. (A): Phase contrast images of R1 (CD73$^+$CD90$^-$)- or H7-derived neurospheres in culture; (B): immunofluorescence analysis of R1 cells stained for nestin, GFAP and TUJ1/β-III-tubulin after neural differentiation; (C): Immunofluorescence analysis of H7 hESCs stained for GFAP and TUJ1/β-III-tubulin after neural differentiation; (D): Immunofluorescence analysis of R1 and H7 hESC stained for tyrosine hydroxylase (TH, red) and vesicular monoamine transporter 2 (VMAT2, green) after differentiation into putative dopaminergic (DA) neurons. DAPI (blue); merge (yellow).

Sustained neurosphere self-renewal capacity was assessed using previously established in vitro assays[22]. Neurosphere formation was restricted to R1 (up to 7 serial passages; FIG. 25, Panels A-D) and R2 fractions (up to 2 serial passages) and exhibited a frequency similar to that for mammosphere formation (~4% of R1 or ~0.2% of the total Lin– population). Expression of the neural progenitor marker nestin was confirmed in the spontaneously differentiated neural lineage cells from R1 and R2 neurospheres. However, whereas 89% and 11% of R1 neurosphere-derived cells expressed neuronal (β-III-tubulin/TUJ-1) and glial (GFAP) differentiation markers, respectively (FIG. 25, Panels A-D), R2 neurosphere-derived cells expressed only GFAP.

Figure 17:
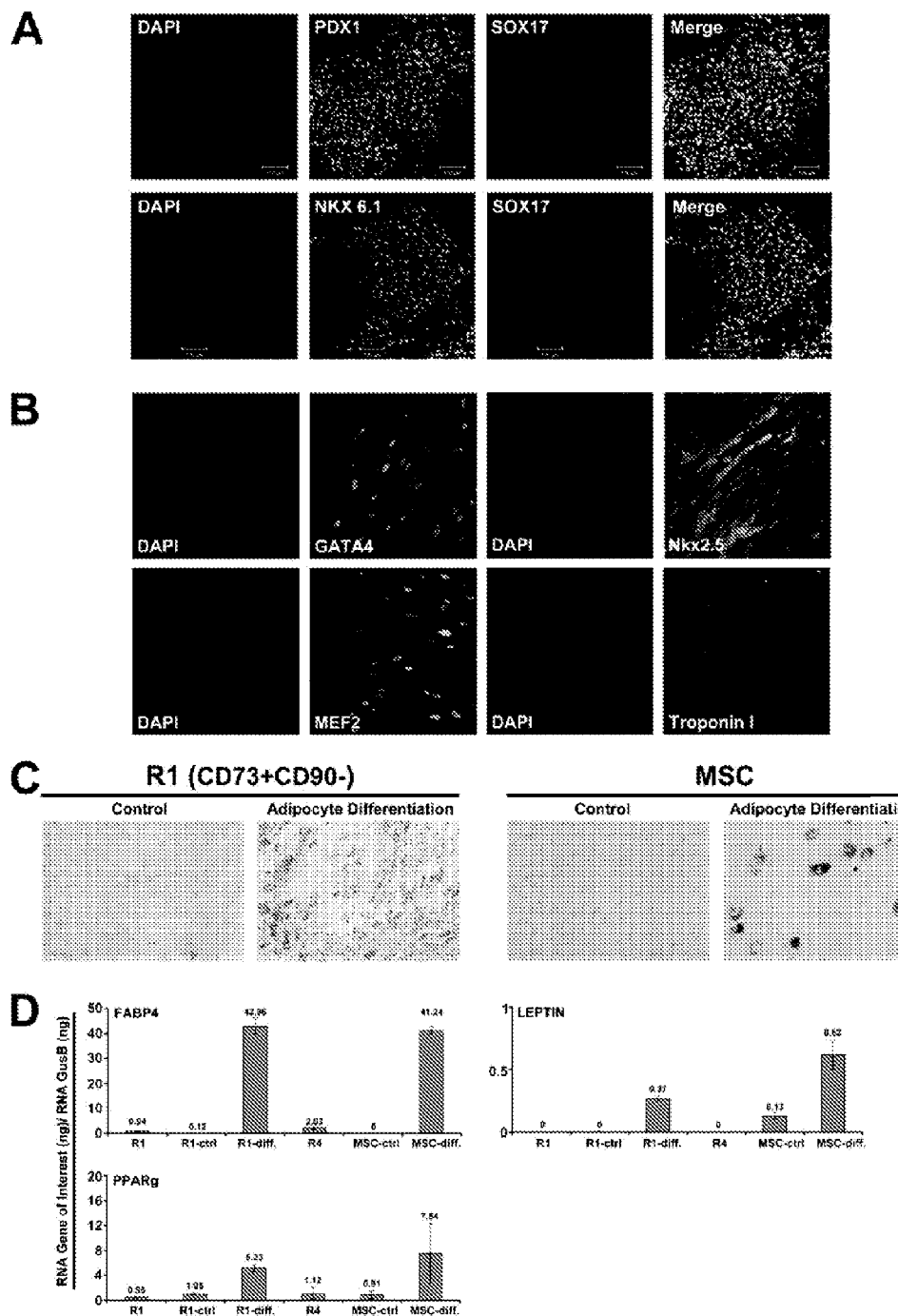
FIG. 17, Panels A-D: R1 epithelial cells differentiate into mesoendodermal lineages. Immunostaining of R1 cells for (A) PDX1, SOX17 and NKX6.1 after 12 days of pancreatic differentiation and (B) GATA4, NKX2.5, MEF2 and Troponin I after 6 days of cardiomyogenic differentiation. Scale=100 μm. (C) Oil Red 0 staining of R1 and human MSC after 9 days of adipogenic differentiation. (D) Transcript levels of fatty acid binding protein 4 (FABP4), LEPTIN and PPARγ (normalized to Glucuronidase B (GUSB)) in directly sorted R1, R1 in expansion medium (R1-ctrl), R1 in adipogenic differentiation medium (R1-diff), MSC in expansion medium (MSC-ctrl), MSC in adipogenic differentiation medium (MSC-diff) and R4.
Figure 26:
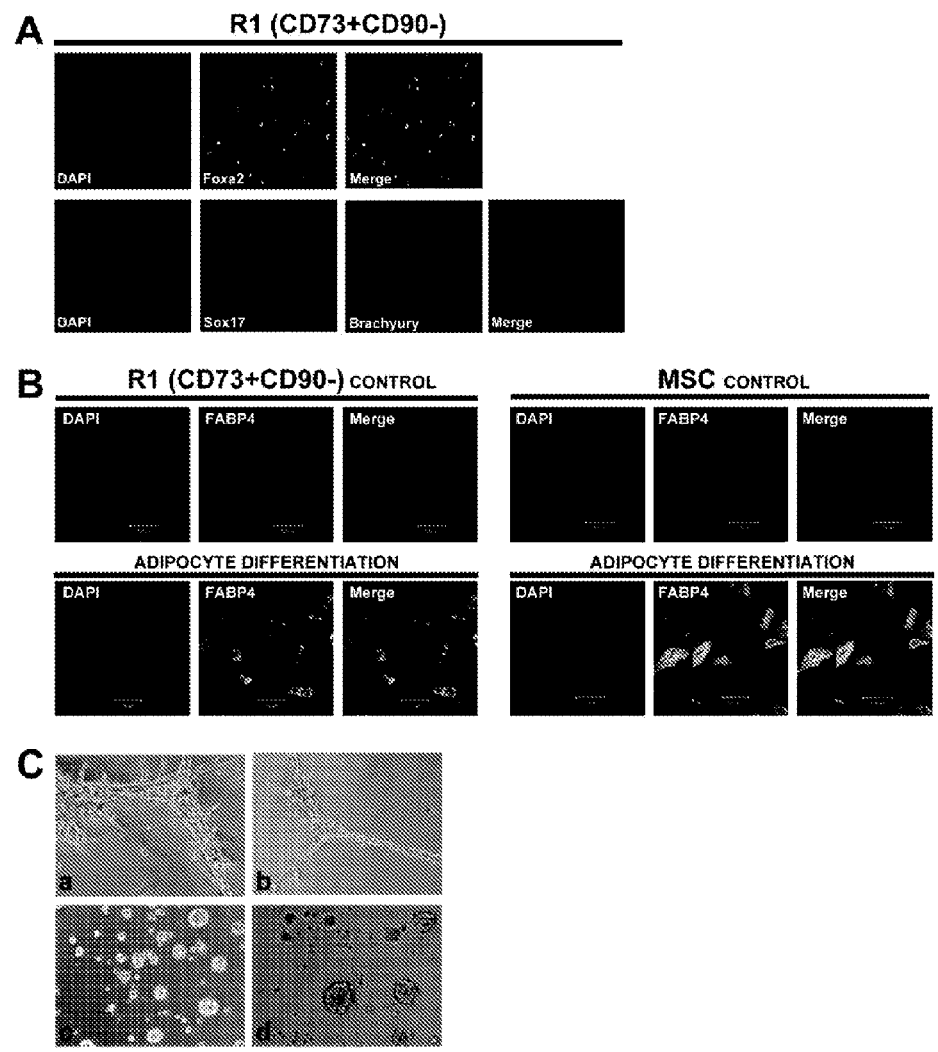
FIG. 26, Panels A-C: Mesoendodermal differentiation potential of R1 cells. Immunoflurescence analysis of R1 cells for (A) endodermal lineage: FOXA2, SOX17 and Brachyury expression after 3 days of differentiation towards definitive endoderm and (B) mesodermal (adipogenic) lineage: FABP4 expression after 19 days of adipogenic differentiation. Human MSCs were used as a positive control. Scale=100 μm. (C) Cord formation capacity evaluated after 24 h in endothelial Matrigel differentiation assay by phase-contrast microscopy for (a) R1, (b) HUVEC, (c) primary human mammary epithelial cells or after 24 h in basal growth medium for (d) primary mammary epithelial cells as a negative control.
Figure 27:
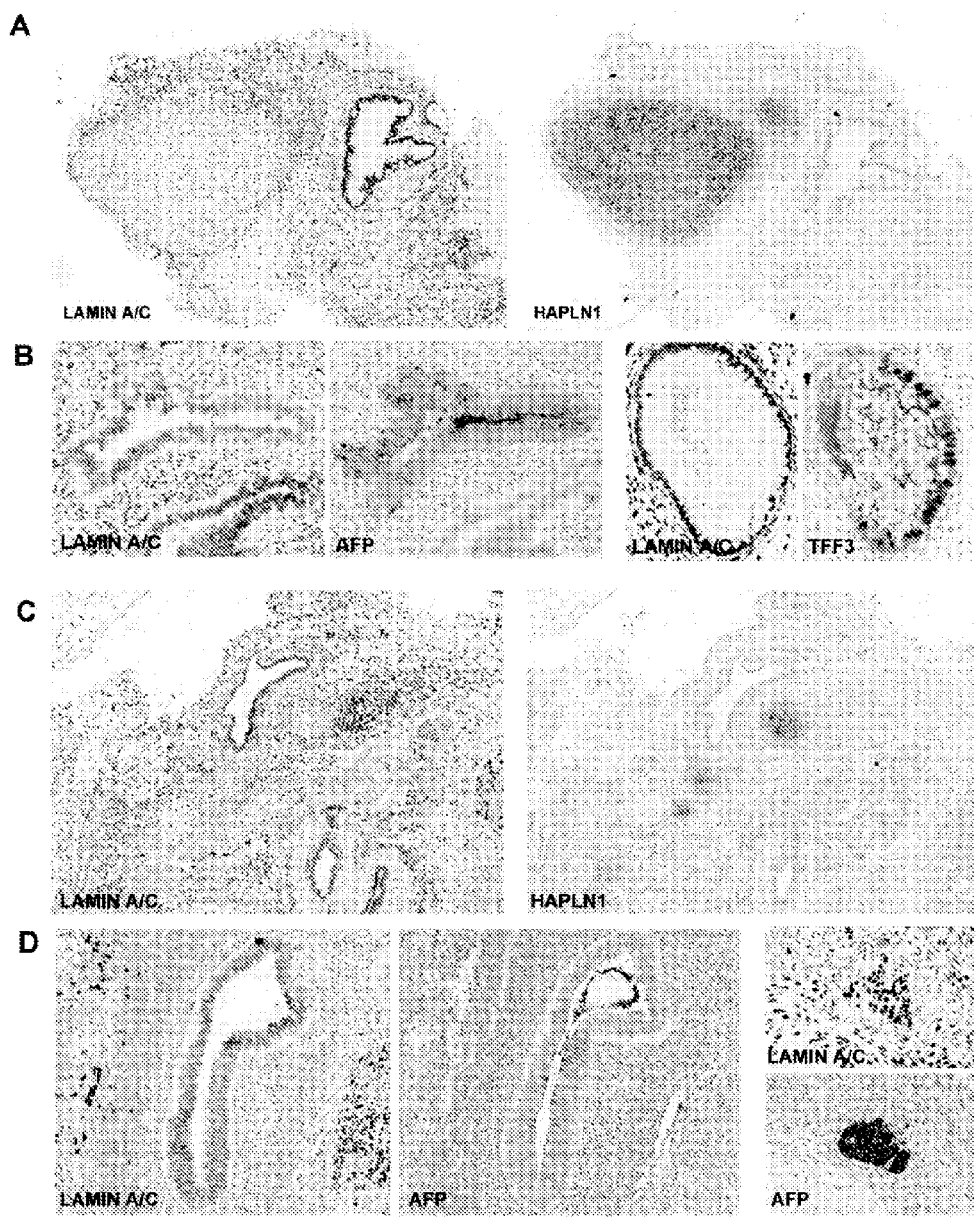
FIG. 27, Panels A-D: Formation of teratomas from directly sorted R1 cell populations or from a single cell-derived R1 subclone. R1 cells directly isolated from reduction mammoplasty tissues (A-B) or a single cell-derived R1 subclone (C-D) were grafted under the renal capsule of SCID/BEIGE mice. Teratomas were harvested 16 weeks after injection. Serial sections from the paraffin-embedded teratomas were stained for the pan-human-specific marker lamin A/C to document the human origin of these structures (A-C, left panel) and for the lineage-specific marker HAPLN1 (A-C, right panel). Representative 40× views of whole teratoma are shown. (B-D) Additional 80× views of structures expressing the endodermal markers AFP and TFF3 and corresponding staining for human lamin A/C. Cells expressing TFF3 document the generation of intestinal goblet cells.

To examine the capacity of R1-R4 subpopulations to differentiate into endodermal lineages, R1-R4 were cultured under conditions that allow human ESCs (hESCs) to differentiate into definitive endoderm and assessed by immunostaining for expression of transcription factors SOX17 and FOXA2. R3 and R4 failed to survive under these conditions. R2 survived but failed to proliferate, and showed very weak cytoplasmic expression of SOX17 and no expression of FOXA2 (data not shown). Only R1 cells displayed definitive endoderm phenotypes, 40% of cells exhibiting SOX17 and FOXA2 nuclear expression (FIG. 26, Panel A). No cells expressed the mesoendodermal marker Brachyury, demonstrating a complete commitment towards definitive endoderm without contribution from a mesoendoderm lineage (FIG. 26, Panel A). Under proper conditions, R1 cells, could further differentiate towards the pancreatic lineage, as demonstrated by the expression of the pancreatic differentiation markers PDX1 and NKX6.1 (FIG. 17, Panel A).

To determine mesodermal potential, R1-R4 were exposed to differentiation media previously reported to induce adult human mesenchymal stem cells (MSCs) and hESCs towards adipocyte, endothelial or cardiomyocyte cell lineages. Under adipogenic conditions, only R1 cells attached and grew. Under endotheliogenic and cardiomyogenic conditions, R1 and R2 survived, whereas R3 and R4 died. Only R1 cells uniformly co-expressed cell type-specific markers such as leptin, PPARγ and FABP4 for adipocytes, CD31 and CD34 for endothelial cells and GATA4, MEF-2, NKX2.5, and Troponin I for cardiomyocytes (FIGS. 17, and 25, Panels A-D). R2 cells expressed only NKX2.5 (data not shown). Functional assays demonstrated the production of lipid-filled adipocytes and tubule-forming endothelial cells from R1 (FIGS. 17, Panel C and 25, Panels A-D). As expected from previous reports, spontaneous beating of cardiomyocytes was only observed when R1 cells were cultured on human placental fibroblast feeders and grown under conditions that promote hESC differentiation into cardiomyocytes. Thus, a small fraction (3%) of $CD73^+$ $CD90^-$ cells from a human somatic cell population exhibits functional expression of markers and phenotypes of ectodermal, endodermal and mesodermal lineages.

Example 12

Formation of Teratomas

Figure 28:
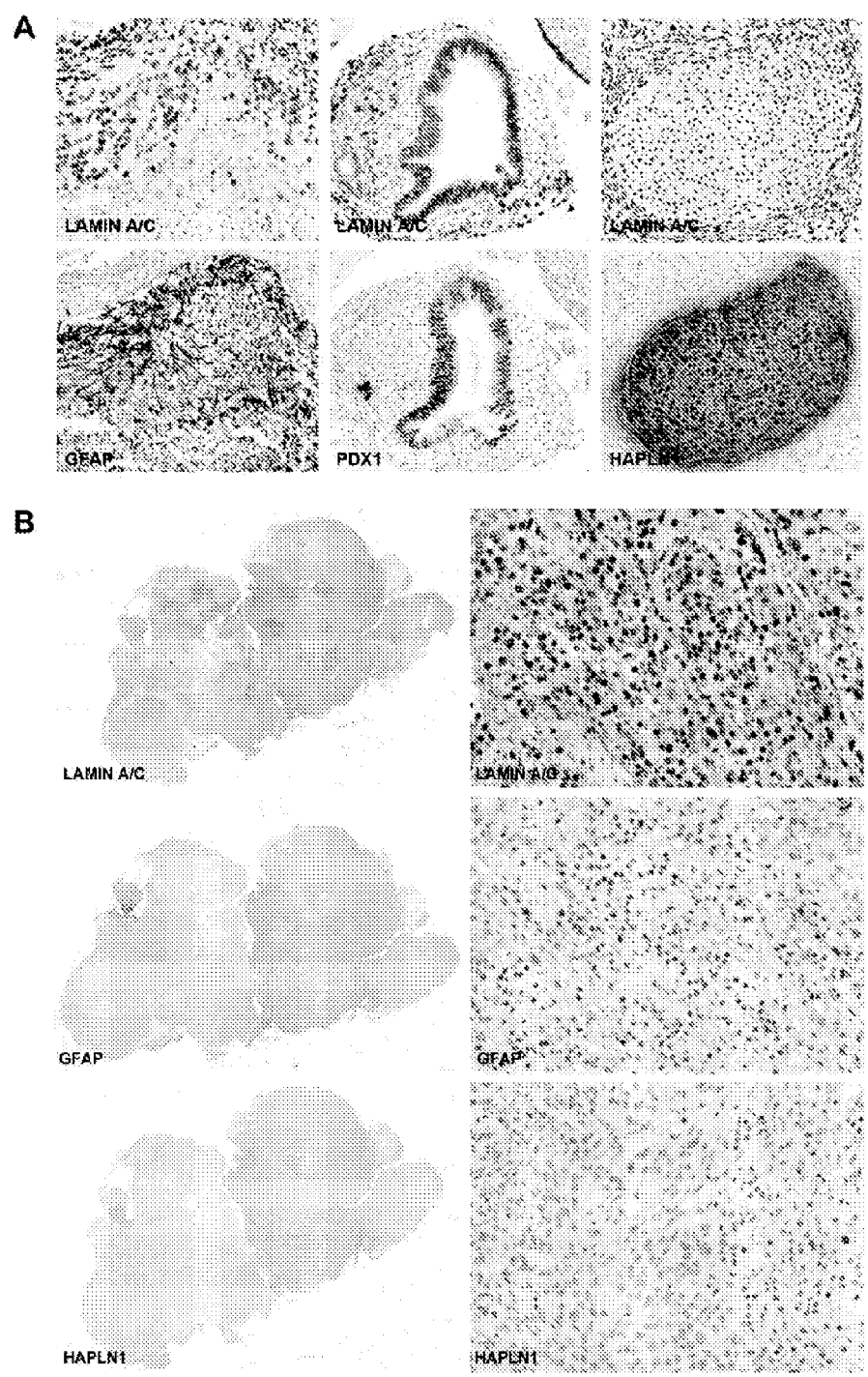
FIG. 28, Panels A-B: Formation of H7 ESCs-derived teratomas and MDA-MB231 mammary tumors. (A) H7 ESCs or (B) MDA-MB231 breast cancer cells were grafted under the renal capsule of SCID/BEIGE mice. H7 ESCs-derived teratomas and MDA-MB231 mammary tumors were harvested 8 weeks after injection. Serial sections from the paraffin-embedded H7 ESCs-derived teratomas or MDA-MB231 mammary tumors were stained for the pan-human-specific marker lamin A/C to document the human origin of these structures (upper panels) and for lineage-specific markers (lower panels). These markers included the glial (ectodermal) marker GFAP, the pancreatic (endodermal) marker PDX1 or the cartilage (mesodermal) marker HAPLN1. (A) 80× views of representative fields of H7 ESCs-derived teratomas (B) 3× views (left column) and 120× views (right column) of representative fields of a MDA-MB231 mammary tumor.

To test the potential for teratoma formation, R1-R4 cells were grafted under the renal capsule of immuno-compromised mice. Both the R1 population sorted directly from mammary tissue (FIGS. 18, Panel A and 27, Panels A-C) and the positive control hESC H7 (FIG. 28, Panel A) generated teratomas with representation of all three germ layers. Populations of R2-R4, as well as pre-malignant mammary cells (184A1), failed to form any cell mass while injection of metastatic mammary cells (MDA-MB-231) formed a malignant tumor with no differentiated structures (FIG. 28, Panel B). Together these data demonstrate that a fraction of the R1 population can generate derivatives of all three developmental lineages and that it is not malignant.

Example 13

Clonal Evidence of Pluripotency

The power of assessing uncultured R1 cells, isolated directly from human tissue, for differentiation potential in a teratoma assay is that the differentiation potential cannot be attributed to cell expansion in culture. However, with this approach, one cannot ascertain that the R1 subfraction consists of single cells each of which has the ability to generate all three germ lineages, i.e. pluripotent cells. Indeed, this R1 population could, alternatively, represent a collection of cells, each with restricted potency for a single germ lineage.

Figure 29:
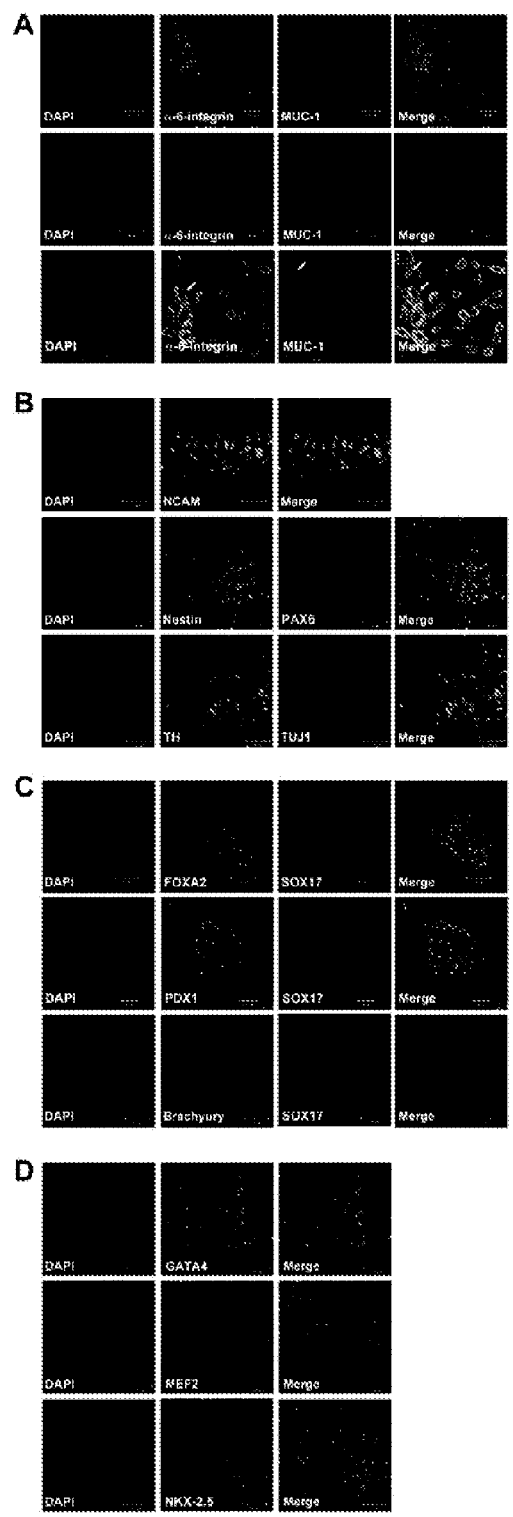
FIG. 29, Panels A-D: In vitro differentiation potential of single cell-derived R1 subclones towards ectodermal, endodermal and mesodermal lineages. Single cells were expanded in culture and assayed for differentiation potential. Immunofluorescence analysis for (A-B) ectodermal lineage: (A) α-6-integrin (myoepithelial) and MUC-1 (luminal) expression after mammary differentiation. Arrows indicate cells expressing only one marker in contrast to the majority of cells which express both markers (bi-potent progenitors); (B) NCAM, Nestin, PAX6, TH and TUJ1/β-III-tubulin expression after neural differentiation; (C) endodermal lineage: FOXA2, SOX17, PDX1 expression after pancreatic differentiation (note the lack of expression of Brachyury documenting a full commitment towards the endoderm lineage) and (D) mesodermal lineage: GATA4, MEF2 and NKX2.5 expression after cardiomyocyte differentiation. Scale=100 μm.

To distinguish between these two possibilities, progeny of R1 single cell-derived subclones, propagated under conditions that allow expansion of pluripotent human ES cells, were manually divided into three parts, placed in each of the in vitro and in vivo differentiation assays described above, and assessed for potency. These single-cell derived R1 subclones generated all previously described lineage derivatives (FIG. 29, Panels A-D). They also formed teratomas with contributions to all three germ lineages (FIGS. 18, Panel B and 27, Panels C-D). Thus, directly sorted R1 cells and single-cell derived R1 subclones are equally potent in generating all three germline derivatives in vitro and in vivo and demonstrating pluripotency.

Figure 30:
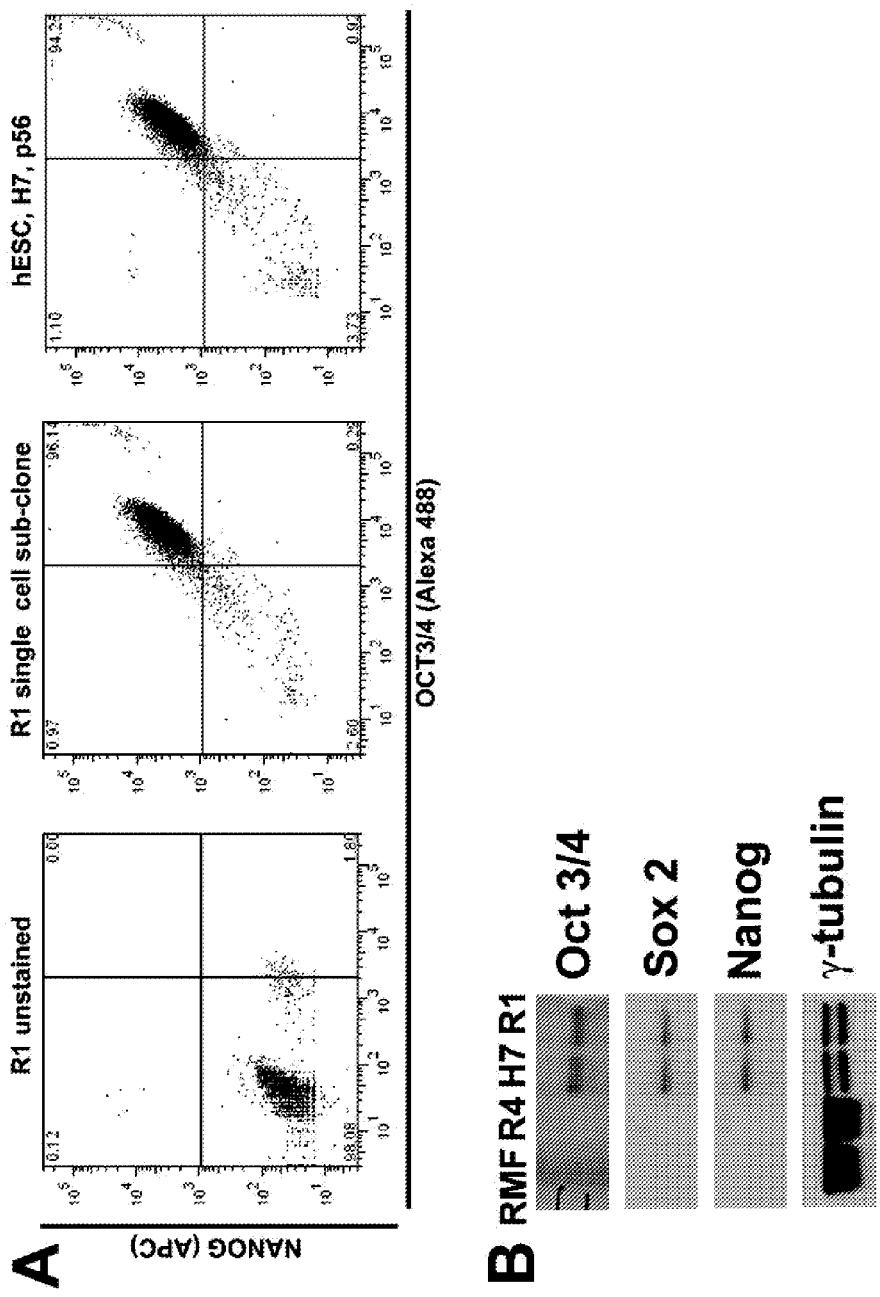
FIG. 30, Panels A-B: Expression of pluripotency markers OCT3/4, SOX2 and NANOG in single cell-derived R1-colonies. Lin-negative, EPCAM-positive epithelial cells were evaluated for expression of OCT3/4, SOX2 and NANOG. (A) Expression of pluripotency markers OCT3/4 and NANOG in individual cells assessed by flow cytometry after 14 days of culture on feeder layers. Left panel: isotype control, middle panel: R1-derived colonies; right panel: H7 hESCs. SOX-2 data are not shown. 96% of the R1 population stained positive for all three markers. (B) Western Blot analysis of pluripotency markers OCT3/4, SOX2 and NANOG in single cell-derived R1-colonies on feeders after 14 days. H7 (positive control), RMF (reduction mammary fibroblasts) and R4 cells (negative controls). Loading control: γ-tubulin.

The pluripotent potential of rare R1 cells isolated from primary tissue became evident when they were placed under conditions known to allow expansion of hESCs. Approximately 3% of the R1 population formed single cell-derived colonies by day 14 (FIG. 19, Panels A-B). The acquisition of a stem cell state could be explained by the robust induction of the canonical pluripotency genes, NANOG, OCT3/4 and SOX2 in these colonies as assayed by four methods. Flow cytometric analysis demonstrated that >95% of cells within each colony co-expressed the three pluripotency genes coincident with the epithelial cell surface marker, EPCAM (FIG. 30, Panel A). Immunocytochemical staining of the colonies provided not only expression levels but also subcellular localization and distribution within the population (FIG. 6, Panel B). Expression of the pluripotency markers was confirmed at the transcript and protein level using qPCR (FIG. 19, Panel A) and Western blot analysis (FIG. 30, Panel B), respectively. The expression of pluripotency markers was not observed within the R2-R4 sub-populations.

To confirm the origin and individual identity of R1 cells, Short Tandem Repeat (STR) was as a forensic analysis to compare markers in FACS isolated cells and a mesodermally-differentiated R1 derivative (beating cardiomyocytes) derived from two breast tissues. Each pair of parental and differentiated samples exhibited identical genetic markers for a given donor, each being distinct from markers from a representative control hESC population or a K562 control cell line (FIG. 14). Collectively, these data demonstrate that a single endogenous Pluripotent Somatic Cell (ePS cell) can exhibit pluripotent functions and generate all three germ lineages when exposed to proper conditions (FIG. 19, Panel D).

Example 14 ePS Cells are Distinct from hESC and MSC

The molecular commonalities and distinctions between the newly characterized pluripotent ePS cell population and well-characterized hESC populations was assessed. Additionally, since CD73 is a cell surface marker in MSCs, MSCs were also included in the comparison. To this end, transcript levels of 43 genes were measured in R1 populations sorted from four reduction mammoplasties using quantitative RT-PCR (qRT-PCR) and compared them with profiles from two hESC and a MSC (FIG. 34). These genes included pluripotency, stress and reprogramming genes. Analysis revealed that R1, although sharing some commonalities with hESCs (FIG. 19, Panel A), exhibited distinct other commonalities with MSCs (FIG. 19, Panel B). One shared characteristic between ePS cells and hESCs, that distinguished them from differentiated cells or MSCs, was the high expression of pluripotency genes OCT3/4, SOX2 and NANOG (FIG. 19, Panel A and FIG. 34). Unlike hESCs, and similar to MSCs, ePS cells expressed much reduced levels of the epigenetic plasticity marker DNMT3b (FIG. 19, Panel B and FIG. 34). Furthermore, R1 cells clearly displayed reduced expression of CD90, this latter phenotype distinguishing them from both hESCs and MSCs (FIG. 19, Panel C). Similar results were obtained using either single cell-derived clonal populations or directly sorted uncultured populations (FIG. 19, Panels A-C and FIG. 34). Thus, ePS cells exhibited a unique expression profile that supported their pluripotent potential and clearly distinguished them from hESCs and MSCs. Finally, also in distinction to immortal hESCs, ePS cells were mortal, grew for up to 58 population doublings and maintained a diploid karyotype before arresting in G1 (FIG. 20, Panels A-C). The ePS population exhibited very low levels of telomerase reverse transcriptase (TERT) and telomerase activity, comparable to those observed in differentiated cells and much lower than those observed in hESCs or malignant cells (FIG. 20, Panels D-E).

Example 15 ePS Cells Obtained from Pancreas and Foreskin

Pancreas: a CD73+CD90– population was isolated from ductal fraction of pancreas. Cells were harvested as single cell isolates, stained with lineage specific markers and CD73 and CD90. Lineage negative cells yield 1% R1 cells (FIG. 35, Panel A). When these cells were sorted fresh and seeded for mammosphere forming assay, R1 cells from pancreas gave rise to mammospheres that were passaged till three passages and differentiated towards myoepithelial and luminal colonies. No beta-casein production was seen in the in vitro conditions. Mammosphere assay using CD49f and MUC-1 staining showed the presence of two types of colonies from R1 cells in pancreas (FIG. 35, Panel B). Samples used: 2

Foreskin: isolation of R1 same as above. The foreskin was divided into epidermis and dermis. R1 from dermis gave rise to mammary-duct like structures in a humanized fat pad experiment. 3 foreskin samples were used for this assay. R1 from epideremis and dermis was used. R1 from dermis gave mammary glands in vivo in the humanized model. The fraction of R1 in both epidermis and dermis was approximately 1%.

DISCUSSION

A unique population of somatic cells isolated from disease-free human breast tissue that exhibits remarkable phenotypic plasticity has been described herein. These cells met benchmarks of pluripotency: (a) demonstration of pluripotency without cell culture, (b) clonal evidence of pluripotency, (c) demonstration of cell type-specific gene expression, (d) functionality of all three lineage derivatives (ectodermal: secretion of human milk in transplanted mice, mesodermal: lipid-accumulating adipocytes, tubule-forming endothelial cells and beating cardiomyocytes, and endodermal: intestinal goblet cells) and finally, (e) exclusion of cell-cell fusion or contamination events (through STR analysis and karyotyping of multiple cell populations before and after differentiation).

As detailed above, ALDEFLUOR positivity of cells was not universally associated with the cells having a full differentiation potential (or a "stem cell phenotype"). For example, ALDEFLUOR-positive cells lacking CD73 did not possess full pluripotent differentiation potential. In contrast, cells expressing CD73 did show full differentiation potential, ALDEFLUOR positivity conferring only a differentiation advantage towards the ectoderm lineage. Cells expressing CD73, regardless of their ALDEFLUOR status, differentiate equally well towards definitive endoderm and mesoderm.

Gene expression data support the conclusion that, although these ePS cells share some commonalities with hESCs and hMSCs, they display unique properties.

Isolation of this unique human somatic cell population is based on the differential expression of two glycosyl-phosphatidylinositol (GPI)-anchored cell surface proteins, the ecto 5'-nucleotidase NT5E/CD73, an extracellular, raft-associated enzyme responsible for conversion of extracellular ATP into adenosine, and the cell adhesion molecule CD90/THY-1. CD73 and CD90 have been used previously as cell surface markers for MSCs. However, lack of EPCAM expression and robust expression of CD90 in MSCs easily distinguishes them from ePS. CD73 can affect cell fate through enzymatic and non-enzymatic mechanisms that result in alterations of the micro-environment and regulation of cell-stroma interactions. CD90 expression has been linked to myofibroblast and tumor-associated fibroblast phenotypes.

The non-malignant state of the ePS cells from multiple individuals was demonstrated. The ePS cells, either directly isolated from human tissue or expanded in culture, exhibit normal diploid 46,XX karyotypes, low telomerase expression and activity and ultimately enter replicative senescence, distinguishing them from immortal, genomically unstable tumor cells. Furthermore, while pre-malignant cells do not form growths, metastatic cells generate robust malignant growths but without the expression of differentiated derivatives seen with ePS cells.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof.

Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. An isolated population of cells,
   wherein at least 8% of the cells are Somatic Cells with an Innate Potential for Pluripotency (SCIPP),
   wherein the SCIPP are CD73$^+$/CD90$^-$/CD45$^-$ cells, wherein CD45 is a Lineage marker, and
   wherein the SCIPP cells are bound by an anti-CD73 antibody,
   wherein the anti-CD73 antibody is immobilized on a solid support or is conjugated to a detectable label.

2. The isolate population of cells of claim 1, wherein the anti-CD73 antibody is immobilized on a solid support.

3. The isolate population of cells of claim 2, wherein the solid support is a bead, plate or a membrane.

4. The isolate population of cells of claim 1, wherein the anti-CD73 antibody is conjugated to a detectable label.

5. The isolate population of cells of claim 4, wherein the detectable label comprises a fluorescent label.

6. The isolate population of cells of claim 1, wherein the SCIPP cells are negative for a Lineage marker selected from the group consisting of: CD2, CD3, CD16, CD31, CD64 and CD140b.

7. The isolate population of cells of claim 1, wherein the SCIPP are derived from disease-free mammary tissue.

8. The isolate population of cells of claim 1, wherein the SCIPP are human SCIPP.

9. The isolate population of cells of claim 1, wherein at least 50% of the cells in the isolated population are SCIPP.

10. An isolated population of cells,
    wherein at least 8% of the cells are Somatic Cells with an Innate Potential for Pluripotency (SCIPP),
    wherein the genetically modified SCIPP are CD73$^+$/CD90$^-$/CD45$^-$ cells, wherein CD45 is a Lineage marker, and
    wherein the SCIPP cells are genetically modified.

11. The isolated population of cells of claim 10, wherein the SCIPP cells are negative for a Lineage marker selected from the group consisting of: CD2, CD3, CD16, CD31, CD64 and CD140b.

12. The isolated population of cells of claim 10, wherein the SCIPP are derived from disease-free mammary tissue.

13. The isolated population of cells of claim 10, wherein the SCIPP are human SCIPP.

14. The isolate population of cells of claim 10, wherein at least 50% of the cells in the isolated population are SCIPP.

* * * * *